United States Patent [19]

Levitt

[11] 4,339,267

[45] Jul. 13, 1982

[54] HERBICIDAL SULFONAMIDES

[75] Inventor: George Levitt, Wilmington, Del.

[73] Assignee: E. I. Du Pont de Nemours and Company, Wilmington, Del.

[21] Appl. No.: 197,749

[22] Filed: Oct. 16, 1980

Related U.S. Application Data

[63] Continuation-in-part of Ser. No. 109,262, Jan. 18, 1980, abandoned, which is a continuation-in-part of Ser. No. 68,658, Aug. 28, 1979, abandoned, which is a continuation-in-part of Ser. No. 14,201, Feb. 22, 1979, abandoned.

[51] Int. Cl.[3] .................... A01N 47/36; C07D 239/70; C07D 491/48; C07D 491/52

[52] U.S. Cl. ........................................ 71/92; 544/116; 544/117; 544/253; 544/278; 544/330; 546/294; 71/76; 71/88; 71/93; 71/94; 71/103

[58] Field of Search .................... 71/92; 544/253, 279, 544/278, 116, 117

[56] References Cited

U.S. PATENT DOCUMENTS

| | | | |
|---|---|---|---|
| 3,436,207 | 4/1969 | Soboczenski | 71/92 |
| 3,539,333 | 11/1970 | Dubrovin | 71/111 |
| 3,637,366 | 1/1972 | Weichmann et al. | 71/92 |
| 3,658,901 | 4/1972 | Timmons et al. | 71/92 |
| 4,116,674 | 9/1978 | Sunley et al. | 71/92 |
| 4,120,691 | 10/1978 | Levitt | 71/93 |
| 4,127,405 | 10/1978 | Levitt | 71/93 |
| 4,169,719 | 10/1979 | Levitt | 71/92 |
| 4,190,432 | 2/1980 | Levitt | 71/93 |
| 4,214,890 | 7/1980 | Levitt | 71/90 |
| 4,221,585 | 9/1980 | Levitt | 71/92 |
| 4,225,337 | 9/1980 | Levitt | 71/93 |

FOREIGN PATENT DOCUMENTS

| | | | |
|---|---|---|---|
| 1514 | 4/1979 | European Pat. Off. . | |
| 7687 | 2/1980 | European Pat. Off. . | |
| 13480 | 7/1980 | European Pat. Off. . | |
| 15683 | 9/1980 | European Pat. Off. . | |
| 17473 | 10/1980 | European Pat. Off. . | |
| 2715786 | 10/1977 | Fed. Rep. of Germany | 71/92 |
| 1468747 | 2/1967 | France . | |
| 121788 | 9/1966 | Netherlands . | |

OTHER PUBLICATIONS

Wojciechowski, J. Acta Polon. Pharm., 19, 121–5, (1962).

Logemann, et al., Farmaco Ed. Sci., 12, No. 7, pp. 586–593, (1957).

*Primary Examiner*—Glennon H. Hollrah
*Assistant Examiner*—Diana G. Rivers

[57] ABSTRACT

N-(heterocyclicaminocarbonyl)aryl and pyridylsulfonamides, useful for the regulation of plant growth and as pre-emergence and post-emergence herbicides.

28 Claims, No Drawings

HERBICIDAL SULFONAMIDES

RELATED APPLICATIONS

This application is a continuation-in-part of my copending application U.S. Ser. No. 109,262, filed Jan. 18, 1980, now abandoned, which is a continuation-in-part of U.S. Ser. No. 068,658, filed Aug. 28, 1979, now abandoned, which is a continuation-in-part of U.S. Ser. No. 014,201, filed Feb. 22, 1979, now abandoned.

BACKGROUND OF THE INVENTION

This invention relates to N-(heterocyclicaminocarbonyl)aryl and pyridylsulfonamide agricultural chemicals.

French Pat. No. 1,468,747 discloses the following para-substituted phenylsulfonamides, useful as antidiabetic agents:

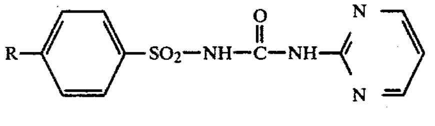

wherein R=H, halogen, $CF_3$ or alkyl.

Logemann et al. Chem. Ab., 53, 18052 g (1959), disclose a number of sulfonamides, including uracil derivatives and those having the formula:

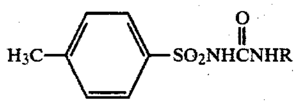

wherein R is butyl, phenyl or

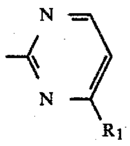

and $R_1$ is hydrogen or methyl. When tested for hypoglycemic effect in rats (oral doses of 25 mg/100 g), the compounds in which R is butyl or phenyl were most potent. The others were of low potency or inactive.

Wojciechowski, J. Acta. Polon. Pharm. 19, p. 121-5 (1962) [Chem. Ab., 59 1633 e] describes the synthesis of N-[(2,6-dimethoxypyrimidin-4-yl)aminocarbonyl]-4-methylbenzenesulfonamide:

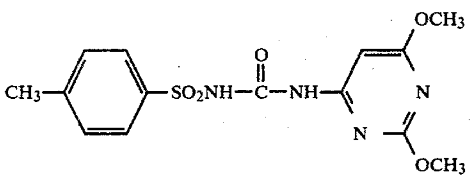

Based upon similarity to a known compound, the author predicted hypoglycemic activity for the foregoing compound.

Netherlands Pat. No. 121,788, published Sept. 15, 1966, teaches the preparation of compounds of Formula (i), and their use as general or selective herbicides,

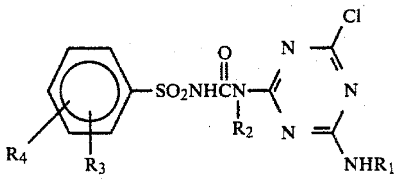

(i)

wherein $R_1$ and $R_2$ may independently be alkyl of 1-4 carbon atoms; and $R_3$ and $R_4$ may independently be hydrogen, chlorine or alkyl of 1-4 carbon atoms.

U.S. Pat. No. 3,637,366 discloses compounds having the formula:

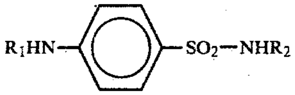

wherein $R_1$ is hydrogen or lower saturated acyl, and $R_2$ is hydrogen, 2-pyrimidinyl, pyridyl, amidino, acetyl or carbamoyl. The disclosed compounds are said to provide control of crabgrass, cress, endive, clover and *Poa annua.*

Substituted pyrimidinyl sulfonyureas of the following formula, which are also para-substituted on the phenyl ring, are disclosed in *Farmco Ed. Sci.,* 12, 586 (1957) [Chem. Ab., 53, 18052 g (1959)]:

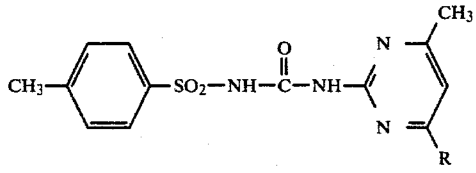

where R=H or $CH_3$.

The presence of undesired vegetation causes substantial damage to useful crops, especially agricultural products that satisfy man's basic food and fiber needs, such as cotton, rice, corn, wheat, and the like. The current population explosion and concomitant world food and fiber shortage demand improvements in the efficiency of producing these crops. Preventing or minimizing the loss of a portion of such valuable crops by killing, or inhibiting the growth of undesired vegetation is one way of improving this efficiency.

A wide variety of materials useful for killing or inhibiting (controlling) the growth of undesired vegetation is available; such materials are commonly referred to as herbicides. Some weeds, (such as nutsedge) are very difficult to control; many of the herbicides that are used to control nutsedge are so nonselective that they cause damage to the crops themselves. Thus, a need exists for active herbicides which cause minimal damage to the crops.

SUMMARY OF THE INVENTION

This invention relates to novel compounds of Formulas I and II and their agriculturally suitable salts, to agricultural compositions containing them and to their method of use as herbicides. Some of the compounds of Formulas I and II have utility for selective weed control in crops such as soybeans. In addition, compounds of Formula II and those compounds of Formula I in which W is sulfur are useful as intermediates to compounds of Formula I in which W is oxygen.

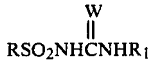
(I)

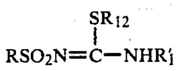
(II)

wherein

R is 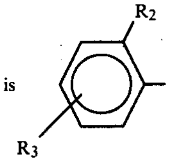 or 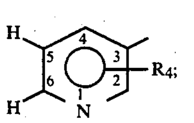

$R_1$ is 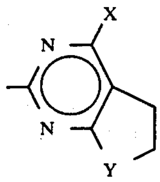 or 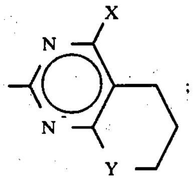;

$R_1'$ is 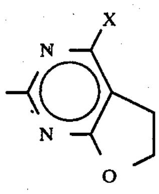 or 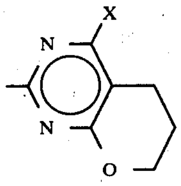;

$R_2$ is H, $CH_3$, $OCH_3$, F, Cl, Br, $NO_2$, $CF_3$, $COR_5$, $S(O)_mR_{10}$, $SO_2NR_{10}R_{11}$, $SO_2OCH_2CF_3$, $SO_2OCH_2CCl_3$ or $SO_2N(OCH_3)CH_3$;

$R_3$ is H, F, Cl, Br, alkyl $C_1$-$C_4$ or $CH_3O$;

$R_4$ is H, Cl, Br, F, alkyl $C_1$-$C_4$, alkoxy $C_1$-$C_4$, $NO_2$, $CO_2R_6$ or $R_{13}$—S—;

$R_5$ is alkoxy $C_1$-$C_6$; alkenyloxy $C_3$-$C_6$; haloalkoxy $C_2$-$C_6$ substituted with 1 to 3 halogens selected from Cl, F and Br; cycloalkoxy $C_5$-$C_6$; $O$—$CH_2CH_2O)_nR_7$; $OCH_2CH_2CH_2OR_7$; $NR_8R_9$; $N(OCH_3)CH_3$ or $C_1$-$C_4$ alkylthio;

$R_6$ is alkyl $C_1$-$C_6$;

$R_7$ is alkyl $C_1$-$C_2$;

$R_8$ and $R_9$ are independently H or alkyl $C_1$-$C_4$ or $R_8$ and $R_9$ may be taken together to be $(CH_2)_4$, $(CH_2)_5$ or $O(CH_2CH_2$—$)_2$; and $R_8$ can also be

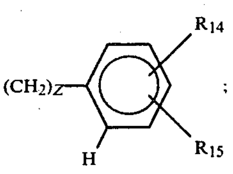;

$R_{10}$ and $R_{11}$ are independently $C_1$-$C_6$ alkyl or $C_3$-$C_4$ alkenyl or $R_{10}$ and $R_{11}$ can be taken together to be $(CH_2)_4$, $(CH_2)_5$ or $O(CH_2CH_2)_2$;

$R_{12}$ is $C_1$-$C_{12}$ alkyl; $CH_2CH_2OCH_3$; $CH_2CH_2OCH_2CH_3$; $CH_2CH_2CH_2OCH_3$; $CH_2CH_2OCH_2CH_3$; $CH_2CH_2CH_2OCH_3$; $CH_2A$ or 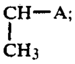;

$R_{13}$ is $C_1$-$C_3$ alkyl;

$R_{14}$ is H, F, Cl, Br, $NO_2$, CN, $CF_3$, $C_1$-$C_3$ alkyl, $OCH_3$ or $CH_3S$;

$R_{15}$ is H, F, Cl, Br, $CH_3$ or $OCH_3$;

X is H, $CH_3$, $CH_3O$, Cl or $OCH_2CH_3$;

Y is $CH_2$ or O;

A is $CO_2H$, $CO_2B$, $CONH_2$, phenyl, CN, $C_2$-$C_4$ alkenyl, $C_2$-$C_4$ alkynyl, phenyl substituted with one or two methyl groups or with one or two chlorines;

B is $C_1$-$C_4$ alkyl;

m is 0, 1 or 2;

n is 1 or 2;

Z is 0 or 1;

W is oxygen or sulfur; provided that (i) when $R_1$ is

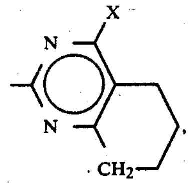, then $R_2$ is $NO_2$, $COR_5$, $SO_2NR_{10}R_{11}$, $SO_2N(CH_3)(OCH_3)$ or $SO_2R_{10}$;

$R_4$ is other than H; and

X is $CH_3$ or $OCH_3$;

(ii) when W is sulfur; then Y is oxygen and their agricuturally suitable salts.

Compounds of Formula Ia and IIa are also novel and are useful as intermediates to herbicidal compounds of Formula I in which W is oxygen.

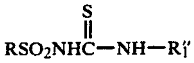 and 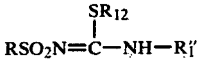

Ia IIa where $R_1''$ is 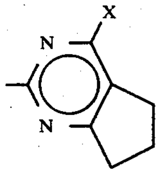 or 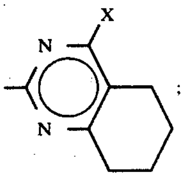; and

R, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, X, A, B, m, n and Z are as previously defined; provided that when $R_1''$ is

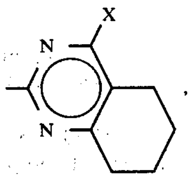, then $R_2$ is $NO_2$, $COR_5$, $SO_2NR_{10}R_{11}$, $SO_2N(CH)_3(OCH_3)$ or $SO_2R_{10}$;

$R_4$ is other than H; and

X is $CH_3$ or $OCH_3$.

Preferred in order of increasing preference for reasons of biological activity or ease of synthesis or both are the following groups of compounds:

(1) Compounds of Formula I wherein W is oxygen;

(2) Compounds of Preferred (1) wherein

R is 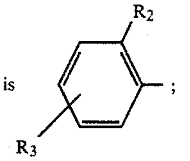 ;

(3) Compounds of Preferred (2) wherein $R_1$ is 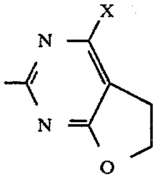 or 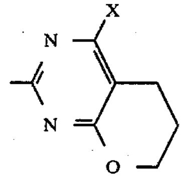

(4) Compounds of Preferred (3) where X is H, $CH_3$ or $OCH_3$;

(5) Compounds of Preferred (4) wherein $R_2$ is $NO_2$, $COR_5$, $SO_2NR_{10}R_{11}$, $SO_2R_{10}$, $SO_2N(OCH_3)(CH_3)$ and $R_{10}$ and $R_{11}$ are $CH_3$ or $CH_3CH_2$;

(6) Compounds of Preferred (5) wherein $R_3$ is H; and (7) Compounds of Preferred (6) wherein $R_5$ is $C_1$–$C_3$ alkoxy or allyloxy.

Specifically preferred for their outstanding herbicidal activity or highly favorable cost or both are:

N-[(6,7-Dihydro-4-methyl-5H-cyclopentapyrimidin-2-yl)-aminocarbonyl]-2-nitrobenzenesulfonamide;

2-{[(6,7-Dihydro-4-methyl-5H-cyclopentapyrimidin-2-yl)-aminocarbonyl]aminosulfonyl}benzoic acid, methyl ester;

N-[(6,7-Dihydro-4-methoxy-5H-cyclopentapyrimidin-2-yl)-aminocarbonyl]-2-nitrobenzenesulfonamide;

2-Chloro-N-[(5,6-dihydro-4-methylfuro[2,3-d]pyrimidin-2-yl)aminocarbonyl]benzenesulfonamide;

2-{[(6,7-Dihydro-4-methyl-5H-cyclopentapyrimidin-2-yl)aminocarbonyl]aminosulfonyl}benzoic acid, ethyl ester;

2-{[(5,6-Dihydro-4-methylfuro[2,3-d]pyrimidin-2-yl)-aminocarbonyl]aminosulfonyl}benzoic acid, ethyl ester;

N-[(5,6-Dihydro-4-methylfuro[2,3-d]pyrimidin-2-yl)-aminocarbonyl]-2-nitrobenzenesulfonamide;

2-{[(5,6-Dihydro-4-methylfuro[2,3-d]pyrimidin-2-yl)-aminocarbonyl]aminosulfonyl}benzoic acid, methyl ester;

N'-[(5,6-Dihydro-4-methylfuro[2,3-d]pyrimidin-2-yl)-aminocarbonyl]-N,N-dimethyl-1,2-benzenedisulfonamide;

2-{[(5,6-Dihydro-4-methoxyfuro[2,3-d]pyrimidin-2-yl)aminocarbonyl]aminosulfonyl}benzoic acid, methyl ester;

2-[[(5,6-Dihydro-4-methoxyfuro[2,3-d]pyrimidin-2-yl)-aminocarbonyl]aminosulfonyl]benzenecarbothioic acid, methyl ester;

1-[2-[[(5,6-Dihydro-4-methoxyfuro[2,3-d]pyrimidin-2-yl)aminocarbonyl]aminosulfonyl]benzoyl]pyrrolidine;

2-[[(5,6-Dihydro-4-methylfuro[2,3-d]pyrimidin-2-yl)-aminocarbonyl]aminosulfonyl]-N,N-dimethylbenzamide;

2-{[(4-Chloro-5,6-dihydrofuro[2,3-d]pyrimidin-2-yl)-aminocarbonyl]aminosulfonyl}benzoic acid, methyl ester;

2-{[(6,7-Dihydro-4-methyl-5H-pyrano[2,3-d]pyrimidin-2-yl)aminocarbonyl]aminosulfonyl}benzoic acid, methyl ester; and 2-{[(6,7-Dihydro-4-methoxy-5H-pyrano[2,3-d]pyrimidin-2-yl)aminocarbonyl]aminosulfonyl}benzoic acid, methyl ester.

Synthesis

As shown in Equation 1, the compounds of Formulas I and Ia can be prepared by combining an appropriate 2-aminopyrimidine of Formula II with an appropriately substituted sulfonyl isocyanate or isothiocyanate of Formula IV; R, X, Y and W being as previously defined and q being 1 or 2.

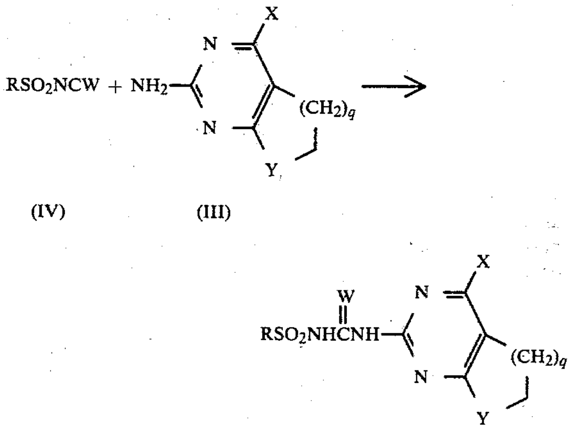

(IV) (III)

(I or Ia)

The reaction is best carried out in inert aprotic organic solvents such as methylene chloride, tetrahydrofuran or acetonitrile, at ambient pressure and temperature. The mode of addition is not critical; however, it is often convenient to add the sulfonyl isocyanate to a stirred suspension of the aminopyrimidine. Since such isocyanates usually are liquids, their addition can be easily controlled.

The reaction is generally exothermic. In some cases, the desired product is insoluble in the warm reaction medium and crystallizes from it in pure form. Products soluble in the reaction medium are isolated by evaporation of the solvent, trituration of the solid residue with solvents such as 1-chlorobutane or ethyl ether, and filtration.

As shown in Equation 2, the compounds of Formulas II and IIa can be prepared by reacting an appropriately substituted carbamimidothioic acid salt of Formula V with an alkylating agent of Formula VI:

Equation 2

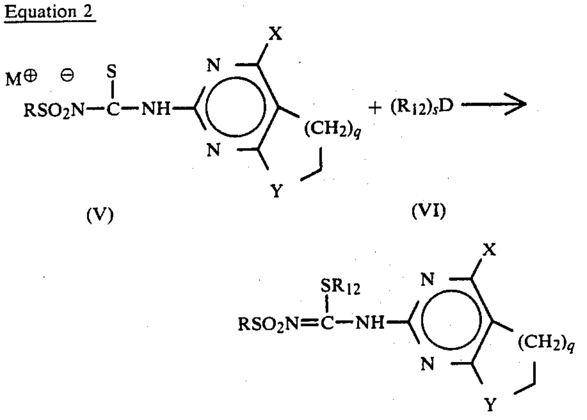

(V) (VI)

(II or IIa)

wherein R, $R_{12}$, X and Y are as previously defined; D is a sulfate or halogen, such as Cl, Br or I; M is an alkali or alkaline earth metal, q is 1 or 2, and s is an integer corresponding to the valence of D.

The reaction is best carried out in inert aprotic organic solvents such as tetrahydrofuran or diethyl ether at temperatures between about 25° and 100° C. and at ambient pressure. The mode of addition is not critical; however, it is often convenient to add the alkylating agent in solution to a stirred suspension of said salt. The end product is isolated by evaporation of the solvent and recrystallization of the residue from a solvent such as acetonitrile or ethanol.

The metal salts of Formula V can be prepared by treating the corresponding sulfonylthiourea (Formula VII, Equation 3) with a solution of an alkali metal or alkaline earth metal salt having an anion sufficiently basic to abstract the proton (e.g. hydroxide, alkoxide, carbonate, or hydride). As shown in Equation 3, the sulfonylthiourea VII can be prepared by combining an appropriately substituted sulfonyl isothiocyanate of Formula VIII with an appropriate 2-aminoheterocycle of Formula III; R, X, Y and q being as previously defined:

Equation 3

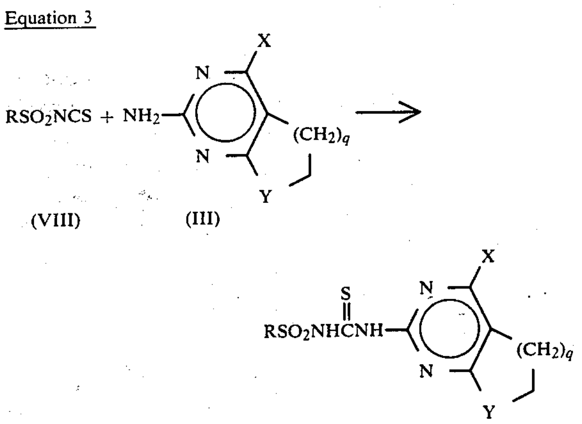

(VIII) (III)

(VII)

The reaction is best carried out in inert aprotic organic solvents such as methylene chloride, tetrahydrofuran or acetonitrile, at ambient pressure and temperature. The mode of addition is not critical; however, it is often convenient to add the isothiocyanate to a stirred suspension of the aminoheterocycle. Since such isothiocyanates usually are liquids, their addition is more easily controlled. Catalysts, such as 1,4-diazabicyclo[2.2.2]octane or dibutyltindilaurate, may be used.

In some cases, sulfonylthioureas of Formula VII are more conveniently prepared, as shown in Equation 4, by reacting an appropriately substituted sulfonamide of Formula IX with the appropriate 2-isothiocyanatoheterocycle of Formula X; R, X, Y and q being as previously defined;

Equation 4

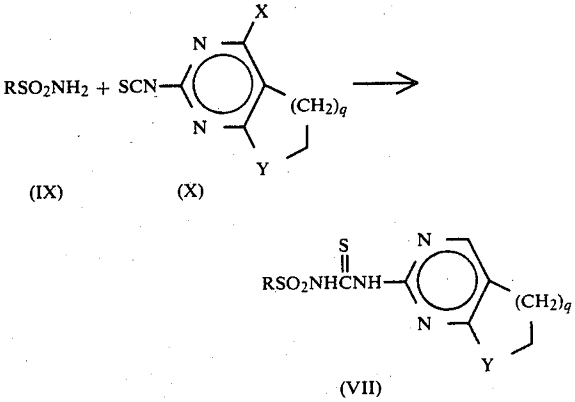

(IX) (X)

(VII)

The preparation of 2-isothiocyanatoheterocycles of Formula X is taught in Japanese patent Kokai 51-143686.

The preparation of the sulfonyl thioureas of Formula VII and reactants therefor is described in said U.S. Applications Ser. Nos. 824,805 and 840,389, the contents of which in that connection are incorporated herein by reference.

The compounds of Formulas II and IIa may also be prepared as shown in Equation 5.

Equation 5

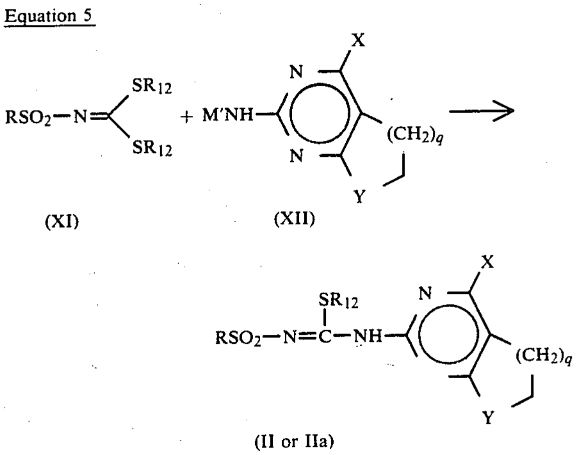

(XI) (XII)

(II or IIa)

A compound of Formula XI is reacted with the salt of the heterocyclic amine at temperatures of 0° to 100° in a suitable solvent e.g., dimethylformamide, dimethylsulfoxide or an ethereal solvent e.g., tetrahydrofuran; R, $R_{12}$, X, Y and q are as previously defined. M′ is an alkali metal cation, e.g., sodium or potassium.

Compounds of Formula XI may be prepared as described in Chem. Ber. 99, 2885 (1966).

a. Sulfonyl isocyanate or Isothiocyanate Intermediates

The intermediate aryl sulfonyl isocyanate of Formula IV (W=O) can be prepared by reacting corresponding aryl sulfonamides with phosgene in the presence of n-butyl isocyanate at reflux in a solvent such as chlorobenzene, according to the procedure of H. Ulrich and A. A. Y. Sayigh, *Newer Methods of Preparative Organic Chemistry*, Vol. VI, p. 223-241, Academic Press, New York and London, W. Foerst Ed. The intermediate pyridyl sulfonyl isocyanates of Formula IV (W=O) can be prepared by reacting an N-(alkylaminocarbonyl)-pyridinesulfonamide with phosgene as described in U.S. patent application No. 966,258, the disclosure of which is hereby incorporated by reference. The N-(alkylaminocarbonyl)pyridinesulfonamide can be prepared, as described in U.S. Ser. No. 966,258, by the reaction of a pyridinesulfonamide, an alkyl isocyanate and an anhydrous base in an anhydrous solvent.

The preparation of sulfonamides from ammonium hydroxide and sulfonyl chloride is widely reported in the literature, e.g., Crossley et al., *J. Am. Chem. Soc.* 60, 2223 (1938). The preparation of pyridylsulfonamide is described in G. Machek, *Monatsch* 2, 84 (1939) and L. Thunus and C. L. Lapiere, *Ann. Farn* 33, 663 (1975).

Certain sulfonyl chlorides are best prepared by chlorosulfonation of a substituted benzene in carbon tetrachloride according to the teaching of H. T. Clarke et al., *Org. Synth.* Coll. Vol. 1, 2nd Ed., 1941, p. 85. Other benzenesulfonyl chlorides are best made by diazotization of the appropriate aniline with sodium nitrite in HCl, followed by reaction of the diazonium salt with sulfur dioxide and cuprous chloride in acetic acid according to the teaching of H. L. Yale and F. Sowinski, *J. Org. Chem.* 25, 1824 (1960). The preparation of pyridyl sulfonyl chlorides is described in *Chem. Abs.* 88, 190603 m (1978).

Sulfonylisothiocyanates of Formula IV (W=S) can be prepared by treatment of sulfonamides with carbon disulfide and potassium hydroxide followed by reaction of the dipotassium salt with phosgene according to the teaching of K. Hartke, *Arch. Pharm.*, 229, 174 (1966).

Pyridine sulfonylisothiocyanates can be prepared according to the procedure taught by K. Dickere and E. Kuhle in U.S. Patent 3,346,590. A suitable pyridinesulfonyliminodithiocarbonate is reacted with phosgene in the presence of a solvent such as toluene or xylene.

A different method is used for preparing the intermediate sulfonyl isocyanate of Formula IV (W=O) when the intermediate is an o-sulfamoylbenzenesulfonyl isocyanate. This method is illustrated by Equations 2a-e.

Equation 2a-d (2a)

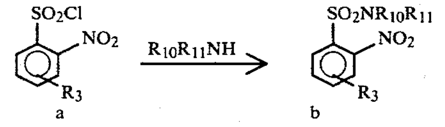

(2b)

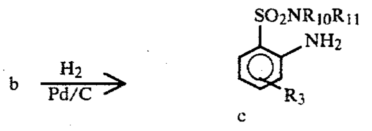

-continued

Equation 2a-d (2c)

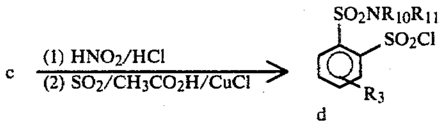

(2d)

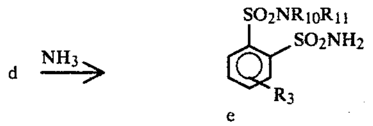

(2e)

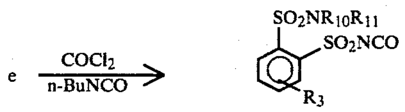

wherein $R_3$, $R_{10}$ and $R_{11}$ are as defined previously.

In step (2a), the o-nitrobenzenesulfonyl chlorides in Formula a, which are well-known in the art, are treated with an amine, $R_{10}R_{11}NH$, in an inert organic solvent such as methylene chloride, ethyl ether, or tetrahydrofuran at 0°-50°. The amine may be taken in excess to act as an acid acceptor; alternatively, a tertiary amine such as triethylamine or pyridine may be used as an acid acceptor. The by-product amine hydrochloride is filtered off or washed out of the solvent with water and the product isolated by evaporation of the solvent.

The reduction described in step (2b) is accomplished by treating a solution of the compounds of Formula b in a solvent such as ethanol, ethyl acetate, or DMF, in a pressure vessel with 100-1000 pounds per square inch of hydrogen at 80°-150° in the presence of a hydrogenation catalyst such as 5-10% palladium absorbed on carbon. When the theoretical amount of hydrogen has been absorbed, the solution is cooled and the catalyst is removed by filtration. The product is then isolated by evaporation of the solvent.

The diazotization and coupling with sulfur dioxide, described in step (2c), is accomplished in the following manner. A solution of the o-sulfamoyl aniline of Formula c in a mixture of concentrated hydrochloric acid and glacial acetic acid is treated with a solution of sodium nitrite in water at −5° to 0°. After stirring for 10-15 minutes at 0° to insure complete diazotization, this solution is added to a mixture of an excess of sulfur dioxide and a catalytic amount of cuprous chloride in glacial acetic acid at 0°-5°. The temperature is kept at 0°-5° for ¼ to 1 hour and is then raised to 20°-25° and held at that temperature for 2-4 hours. This solution is then poured into a large excess of ice water. The sulfonyl chloride products, d, can be isolated by filtration or by extraction into solvent such as ethyl ether or methylene chloride followed by evaporation of the solvent.

The amination described in step (2d) is conveniently carried out by treating a solution of the sulfonyl chloride of Formula d with an excess of anhydrous ammonia in a solvent such as ethyl ether or methylene chloride at 0°-25°. If the product sulfonamide is insoluble it may be isolated by filtration followed by washing out the salts with water. If the product sulfonamide is soluble in the reaction solution, it may be isolated by filtering off the precipitated ammonium chloride and evaporating the solvent.

Sulfonylisocyanates of Formula IV in which $R_2$ is $SO_2OCH_2CCl_3$, $SO_2OCH_2CF_3$ or $SO_2N(CH_3)OCH_3$ can be prepared by a sequence analogous to that shown in Equations 2a-e.

b. Aminopyrimidine Intermediates

The synthesis of heterocyclic amine derivatives such as those depicted by Formula III has been reviewed in "The Chemistry of Heterocyclic Compounds", a series published by Interscience Publ., New York and London. Aminopyrimidines are described by D. J. Brown in "The Pyrimidines", Vol. XVI of the above series.

Preparation of compounds of Formula III varies according to the definition of X, Y and q.

Braker, Sheehan, Spitzmiller and Lott, *J. Am. Chem. Soc.* 69, 3072 (1947) describe the preparation of 6,7-dihydro-4-methoxy-5H-cyclopentapyrimidin-2-amine by the following sequence of reactions.

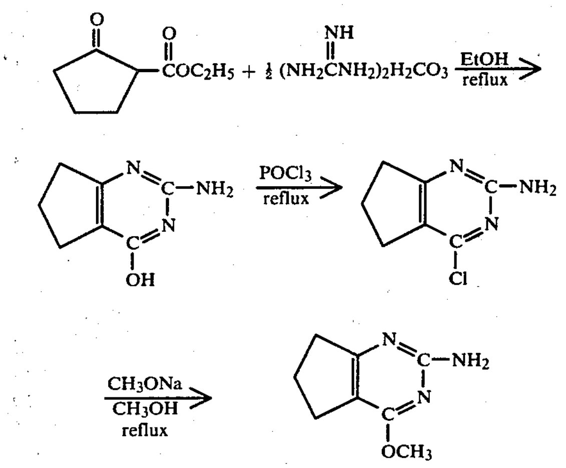

6,7-dihydro-4-methoxy-5H-cyclopentapyrimidin-2-amine.

An analogous sequence of reactions can be used to prepare 5,6,7,8-tetrahydro-4-methoxy-2-quinazolinamine.

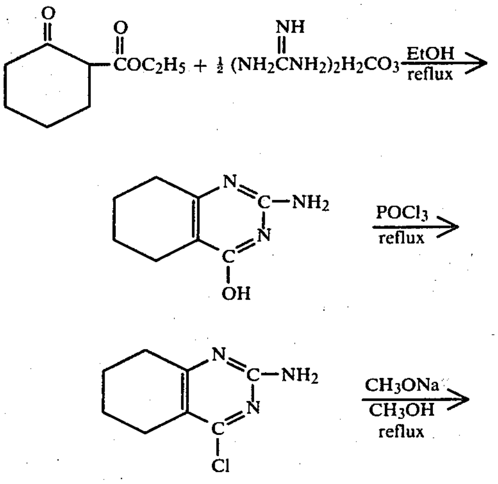

-continued

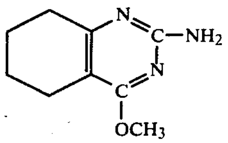

5,6,7,8-tetrahydro-4-methoxy-2-quinazolinamine.

Mitter and Bhattacharya, *Quart. J. Indian Chem. Soc.* 4, 152 (1927) describe the preparation of 5,6,7,8-tetrahydro-4-methyl-2-quinazolinamine as follows:

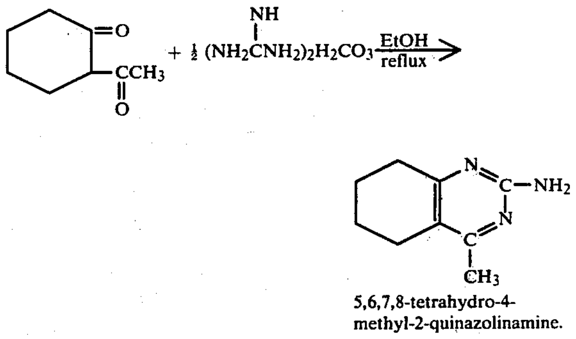

5,6,7,8-tetrahydro-4-methyl-2-quinazolinamine.

Similarly, 6,7-dihydro-4-methyl-5H-cyclopentapyrimidin-2-amine can be prepared by the condensation of 2-acetylcyclopentanone with guanidine carbonate, but preferably by heating in dimethylsulfoxide at 135° for several hours.

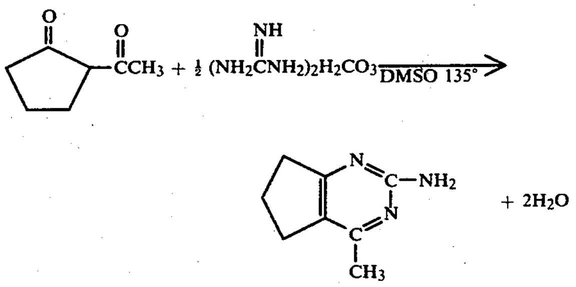

6,7-dihydro-4-methyl-5H-cyclopentapyrimidin-2-amine.

Shrage and Hitchings, *J. Org. Chem.* 16, 1153 (1951) describe the preparation of 5,6-dihydro-4-methylfuro [2,3-d]pyrimidin-2-amine by the following sequence of reactions

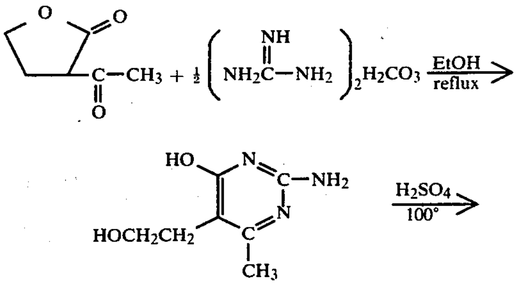

-continued

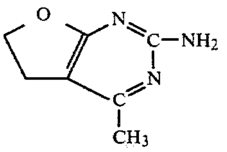

An analogous sequence of reactions can be used to prepare 6,7-dihydro-4-methyl-5H-pyrano[2,3-d]pyrimidin-2-amine starting with 2-acetyl-8 valerolactone [Korte and Wusten, Tetrahedron 19, 1423 (1963)].

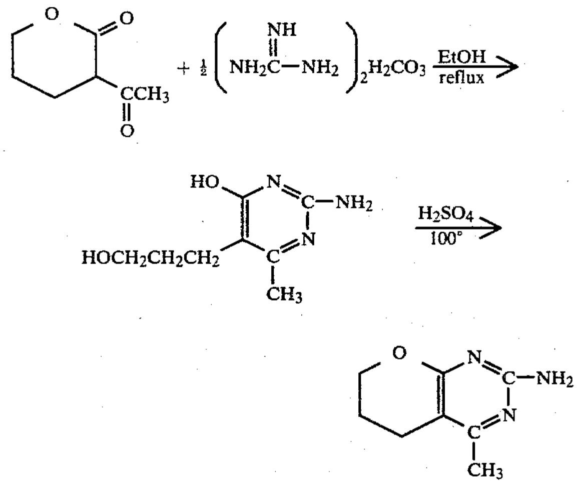

5,6-Dihydro-4-hydroxyfuro[2,3-d]pyrimidine-2-amine [Svab, Budesinski and Vavrina, *Collection Czech. Chem. Commun.* 32, 1582 (1967)] can be converted to 2-amino-5-(2-chloroethyl)-4,6-dichloropyrimidine by heating with phosphorus oxychloride. The product can be subsequently cyclized by treatment with two equivalents of aqueous sodium hydroxide to afford 4-chloro-5,6-dihydrofuro[2,3-d]pyrimidin-2-amine, which is then converted to 5,6-dihydro-4-methoxyfuro[2,3-d]pyrimidin-2-amine by heating with excess sodium methoxide in methanol.

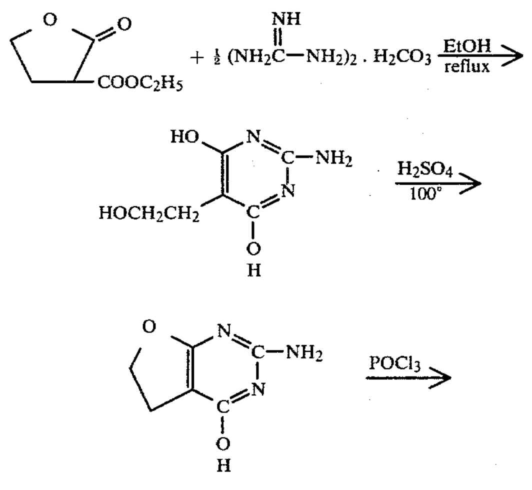

-continued

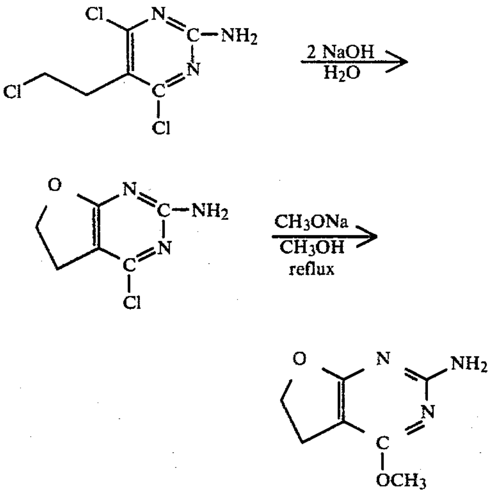

6,7-Dihydro-4-hydroxy-5H-pyrano[2,3-d]pyrimidin-2-amine can be prepared from diethyl 3-chloropropylmalonate, guanidine carbonate and sodium ethoxide in ethanol. Treatment of the product

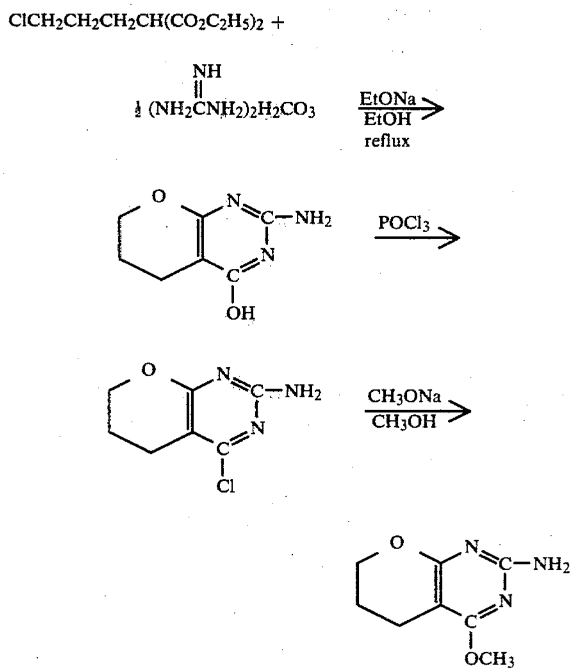

with phosphorus oxychloride gives 4-chloro-6,7-dihydro-5H-pyrano[2,3-d]pyrimidin-2-amine and subsequent reaction with sodium methoxide in refluxing methanol affords 6,7-dihydro-4-methoxy-5H-pyrano[2,3-d]pyrimidin-2-amine.

Compounds of Formulas I, Ia, II and IIa where X is ethoxy can be prepared by a procedure analogous to the methoxy derivatives.

Caldwell, Kornfeld and Donnell, *J. Am. Chem. Soc.* 63, 2188 (1941), describe the preparation of 6,7-dihydro-5H-cyclopentapyrimidin-2-amine by the following sequence of reactions.

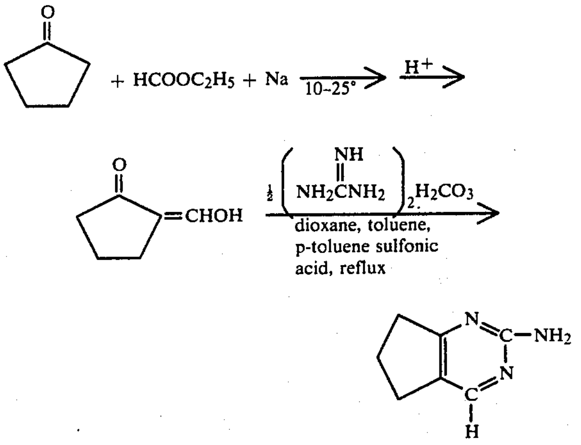

Fissekis, Myles and Brown, *J. Org. Chem.* 29, 2670 (1964), describe the preparation of 2-amino-4-hydroxy-5-(2-hydroxyethyl)pyrimidine which can be converted to 5,6-dihydrofuro[2,3-d]pyrimidin-2-amine by dehydration.

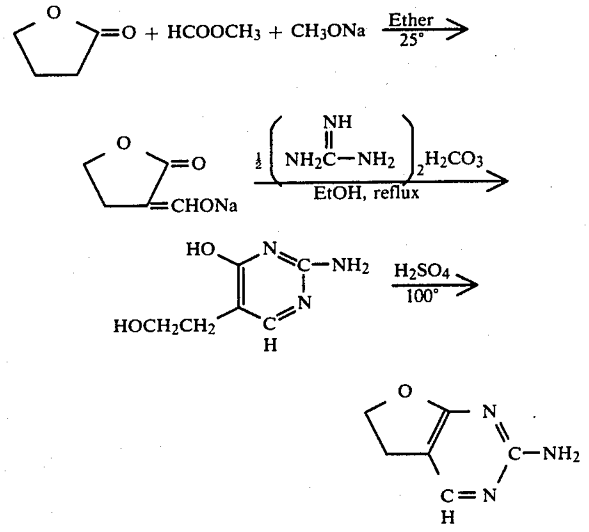

c. Special Situations

When $R_5$ is $NR_8R_9$ in Formula I or Ia, the compounds of this invention can be prepared by reacting the appropriate compound of Formula XIII with the appropriate alkylaminodialkylaluminum derivative of Formula XIV. This is illustrated in Equation 6, wherein y'1 to 6.

Equation 6

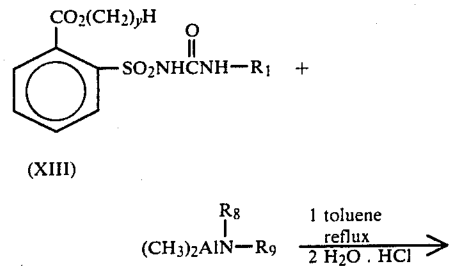

(XIII)

(XIV)

-continued

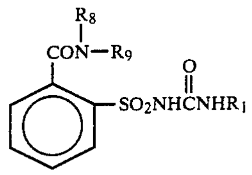

The compounds of Formula XIII are prepared in the manner described above. The intermediate alkylaminodialkylaluminum derivatives of Formula XIV, which are prepared according to A. Basha, M. Lipton and S. Weinreb, *Tetrahedron Letters,* 4171 (1977), are treated with suspensions of the appropriate esters in toluene or a similar inert solvent, and the mixture is refluxed for one to six hours. The product can be isolated by evaporation of the toluene, adding methylene chloride, water and hydrochloric acid to decompose the residual reaction mass and extracting the product into methylene chloride. Evaporation of the methylene chloride yields the desired product, sufficiently pure for the purposes of this invention.

When $R_5$ is $C_1$–$C_4$ alkylthio, these compounds can be prepared from the esters of this invention wherein $R_5$ is $C_1$–$C_4$ alkoxy by the reaction of the esters with the appropriate dialkylaluminum alkylthiolate according to Equation 7.

Equation 7

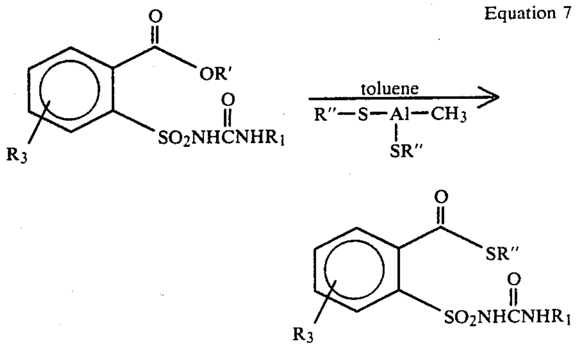

The intermediate aluminum thiolates can be prepared according to R. P. Hatch and S. W. Weinreb, *Journal of Organic Chemistry,* Vol. 42, 3960 (1977). The reaction of the thiolate with the ester of this invention is best carried out in a neutral solvent such as toluene or xylene at reflux for one to three hours. Best results are obtained when the aluminum thiolate compound is present in excess of the stoichiometric amount required.

An alternate route to prepare compounds where $R_5$ is a secondary alcohol residue involves the reaction of the appropriate dialkylaluminum alcoholate and an ester of this invention wherein R' is a lower primary alkyl group, preferably methyl, according to Equation 8.

Equation 8

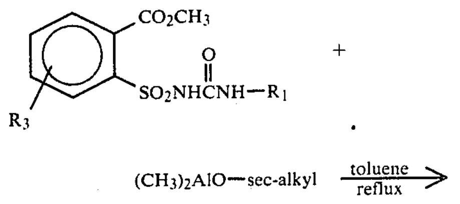

-continued

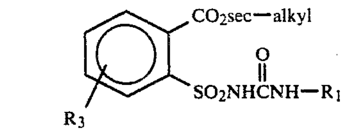

The reaction is carried out in a neutral solvent such as toluene with a boiling point sufficiently high to bring about the desired reaction during reflux. The dialkylaluminum alcoholate being present in greater than an equivalent amount to the ester for best yields. After refluxing for 1–15 hours, the reaction mixture is decomposed with dilute hydrochloric acid and the product extracted into methylene chloride. Evaporation of the methylene chloride yields the desired compound sufficiently pure for the purposes of this invention. The product can be triturated with a solvent, e.g. 1-chlorobutane to remove impurities.

Thioureas and isothioureas may be readily converted to their corresponding ureas, as depicted in Equation 9, with oxidizing agents such as hydrogen peroxide or mercuric oxide. This method of preparing ureas is known in the literature and is described in "Open-Chain Nitrogen Compounds" by P. A. S. Smith (W. A. Benjamin, New York, 1965) p. 274.

Equation 9

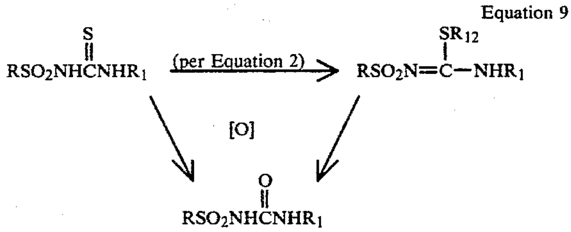

The disclosures of all references cited above are herein incorporated by reference.

Agriculturally suitable salts of compounds of Formula I or II are also useful herbicides and can be prepared by a number of ways known to the art. For example, metal salts can be made by treating compounds of Formula I or II with a solution of alkali or alkaline earth metal salt having a sufficiently basic anion (e.g., hydroxide, alkoxide, carbonate or hydride). Quaternary amine salts can be made by similar techniques.

Salts of compounds of Formula I or II can also be prepared by exchange of one cation for another Cationic exchange can be effected by direct treatment of an aqueous solution of a salt of a compound of Formula I or II (e.g., alkali metal of quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula I or II (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water soluble, e.g, a potassium, sodium or calcium salt.

Acid addition salts, useful in this invention, can be obtained by reacting a compound of Formula I or II with a suitable acid, e.g., p-toluenesulfonic acid, trichloroacetic acid or the like.

The compounds of this invention and their preparation are further illustrated by the following examples wherein temperatures are given in degrees centigrade.

EXAMPLE 1

2-Amino-5-(2-chloroethyl)-4,6-dichloropyrimidine

A mixture of 10 g of 6,7-dihydro-4-hydroxyfuro-[2,3-d]pyrimidin-2-amine, 100 ml of phosphorus oxychloride and 0.5 ml N,N-dimethylaniline were heated at 100°–110° for 2 hours. Excess phosphorus oxychloride was removed under reduced pressure and the residue was mixed with 500 g ice then neutralized to pH 7 with ammonium hydroxide solution. The solid product was collected by filtration, rinsed with water and dried to yield 12 g of 2-amino-5-(2-chloroethyl)-4,6-dichloropyrimidine, m.p. 210°–213°. The mass spectrum exhibited a parent ion at m/e 225, 227, 229 and showed two triplets at 3.40 and 3.88 ppm by nuclear magnetic resonance spectrum (60 MHz), indicating the title compound.

EXAMPLE 2

4-Chloro-5,6-dihydrofuro[2,3-d]pyrimidin-2-amine

A suspension of 6.0 g of 2-amino-5-(2-chloroethyl)-4,6-dichloropyrimidine, 29 ml of 2 N aqueous sodium hydroxide solution, 35 ml water and 75 ml of t-butanol was heated to reflux (60°) for 24 hours then cooled. The solid was collected by filtration, rinsed with water and dried to yield 2.4 g of 4-chloro-5,6-dihydrofuro[2,3-d]pyrimidin-2-amine, m.p. 258°–263°. The product showed characteristic triplet absorption bands at 3.40 and 5.10 ppm in the nuclear magnetic resonance spectrum (60 MHz), indicating the title compound.

EXAMPLE 3

5,6-Dihydro-4-methoxyfuro[2,3-d]pyrimidin-2-amine

To a suspension of 27 g of 4-chloro-5,6-dihydrofuro[2,3-d]pyrimidin-2-amine in 500 ml of anhydrous methanol was added 22 g of sodium methoxide and the mixture was heated to reflux (66°) for 5.5 hours. The solvent was then removed under reduced pressure and the residue triturated with water (500 ml) then filtered and rinsed well with water. The solid was air dried to give 20 g of 5,6-dihydro-4-methoxyfuro[2,3-d]pyrimidin-2-amine, m.p. 172°–177°. Two triplet absorptions at 3.42 and 5.02 ppm and a singlet absorption at 4.21 ppm in the nuclear magnetic resonance spectrum (60 MHz), indicated the title compound.

EXAMPLE 4

2-[[6,7-Dihydro-4-methyl-5H-cyclopentapyrimidin-2-yl)aminocarbonyl]aminosulfonyl]benzoic acid, cyclopentyl ester To 20 ml of dry toluene was added 2.4 ml of 2 M trimethylaluminum in toluene under a nitrogen atmosphere. Subsequently, 0.82 g cyclopentanol in 1 ml toluene was added via syringe and the mixture stirred at ambient temperature for 15 minutes. After addition of 1.56 g of methyl 2-[[(6,7-dihydro-4-methyl-5H-cyclopentapyrimidin-2-yl)aminocarbonyl]aminosulfonyl]benzoate to the mixture, the reaction was heated to 80° for 3.5 hours. The mixture was then cooled in ice while B 40 ml of 5% aqueous hydrochloric acid was added. Ethyl acetate was then added and shaking of the two phase mixture resulted in the crystallization of the product which was collected and dried to yield 1.5 g of 2-[[(6,7-dihydro-4-methyl-5H-cyclopentapyrimidin-2-yl)aminocarbonyl]aminosulfonyl]benzoic acid, cyclopentyl, ester, m.p. 183°-184°. The product showed characteristic absorptions at 3120, 1725, 1720 $cm^{-1}$ in the infrared spectrum and at 1.7-2.35, 2.50, 2.95, 5.4, 7.6, 8.4, 8.5 and 13.0 ppm in the nuclear magnetic resonance spectrum (60 MHz), indicating the title compound.

EXAMPLE 5

N-[(6,7-Dihydro-4-methyl-5H-cyclopentapyrimidin-2-yl)-aminocarbonyl]-2-nitrobenzenesulfonamide To a dry, stirred solution of 10 g of 6,7-dihydro-4-methyl-5H-cyclopentapyrimidin-2-amine in 800 ml of methylene chloride at ambient temperature and pressure was added 14.9 g of 2-nitrobenzenesulfonylisocyanate. The resulting mixture was stirred at reflux temperature (42°) for 2 hours after which the methylene chloride was removed under reduced pressure. The resulting solid was triturated with methanol or 1-chlorobutane and filtered to yield 15 g of N-[(6,7-dihydro-4-methyl-5H-cyclopentapyrimidin-2-yl)aminocarbonyl]-2-nitrobenzene-sulfonamide, m.p. 202°-205°. The product showed characteristic absorption bands in the infrared spectrum at 1675 $cm^{-1}$ and at 1.7, 3.2 and 7.7 to 8.5 ppms by nuclear magnetic resonance spectrum (60 MHz), indicating the title compound.

By application of one or more of the procedures of Examples 1 to 5 and/or the methods described above, and using the appropriate reactants, the compounds of Table I can be prepared.

TABLE I-A

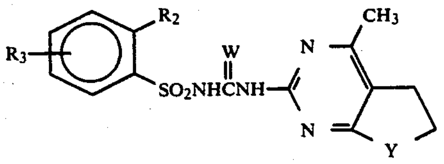

| $R_2$ | $R_3$ | W | Y | m.p. |
|---|---|---|---|---|
| $-H$ | H | O | $CH_2$ | |
| $-Cl$ | H | O | $CH_2$ | 190-192° |
| $-F$ | H | O | $CH_2$ | |
| $-Br$ | H | O | $CH_2$ | |
| $-SCH_3$ | H | O | $CH_2$ | |
| $-SO_2CH_3$ | H | O | $CH_2$ | |
| $-CF_3$ | H | O | $CH_2$ | |
| $-NO_2$ | H | O | $CH_2$ | 202-205° |
| $-CO_2CH_3$ | H | O | $CH_2$ | 193-194° |
| $-CO_2CH_2CH_3$ | H | O | $CH_2$ | 153-154° |
| $-CO_2CH_2CH_2Cl$ | H | O | $CH_2$ | |
| $-CO_2CH_2CH_2CH_3$ | H | O | $CH_2$ | |
| $-CO_2CH_2CH_2OCH_3$ | H | O | $CH_2$ | |
| $-CO_2CH_2CH_2Br$ | H | O | $CH_2$ | |
| $CO_2CH(CH_3)_2$ | H | O | $CH_2$ | 207-210° |
| $CO_2CH_2CH=CH_2$ | H | O | $CH_2$ | 167-172° |
| $CO_2CH_2CF_3$ | H | O | $CH_2$ | |
| $CO_2(CH_2)_3CH_3$ | H | O | $CH_2$ | 160-161° |
| $CO_2CH(CH_3)CH_2CH_3$ | H | O | $CH_2$ | |
| $CO_2CH(CH_2CH_3)_2$ | H | O | $CH_2$ | |
| $CO_2CH_2C(CH_3)_3$ | H | O | $CH_2$ | |
| $CO_2CH_2CH=CH-CH_3$ | H | O | $CH_2$ | |
| $CO_2CH(CH_3)CH=CH_2$ | H | O | $CH_2$ | 190-191° |
| $CO_2CH_2CH=CH(CH_2)_2CH_3$ | H | O | $CH_2$ | |
| $CO_2(CH_2)_4Cl$ | H | O | $CH_2$ | |
| $CO_2(CH_2)_6Cl$ | H | O | $CH_2$ | |
| $CO_2-$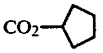 | H | O | $CH_2$ | 183-184° |
| $CO_2-$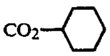 | H | O | $CH_2$ | 193-195° |
| $CO_2(CH_2CH_2O)_2CH_3$ | H | O | O | $CH_2$ |
| $CO_2(CH_2CH_2O)_2C_2H_5$ | H | O | $CH_2$ | |
| $CO_2CH_2CH_2CH_2OCH_3$ | H | O | $CH_2$ | |
| $CO_2CH_2CH_2CH_2OC_2H_5$ | H | O | $CH_2$ | |
| $CON(CH_3)_2$ | H | O | $CH_2$ | 170-172° |
| $CON(C_2H_5)_2$ | H | O | $CH_2$ | 166-169° |
| $CON-CH_3$<br>$\quad | $<br>$CH(CH_3)_2$ | H | O | $CH_2$ | |
| $CONH_2$ | H | O | $CH_2$ | |
| $CONHCH_3$ | H | O | $CH_2$ | |
| $CO_2CH_2CH_2OC_2H_5$ | H | O | $CH_2$ | |
| $CON(CH(CH_3)_2)_2$ | H | O | $CH_2$ | |

TABLE I-A-continued

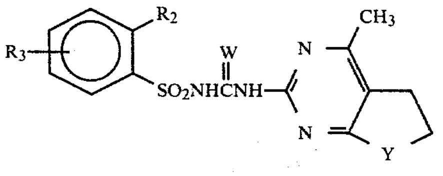

| $R_2$ | $R_3$ | W | Y | m.p. |
|---|---|---|---|---|
| 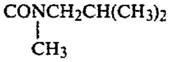 | H | O | $CH_2$ | |
| $CON(CH_2CH_2CH_2CH_3)_2$ | H | O | $CH_2$ | |
| 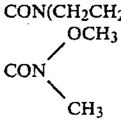 | H | O | $CH_2$ | |
| 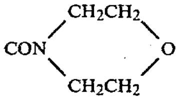 | H | O | $CH_2$ | 189–190° |
| Cl | 5-Cl | O | $CH_2$ | 201–203° |
| Cl | 6-Cl | O | $CH_2$ | |
| Cl | 4-Cl | O | $CH_2$ | |
| Cl | 3-Cl | O | $CH_2$ | |
| F | 5-Cl | O | $CH_2$ | |
| F | 3-Cl | O | $CH_2$ | |
| F | 4-Cl | O | $CH_2$ | |
| F | 5-F | O | $CH_2$ | |
| Cl | $5\text{-}OCH_3$ | O | $CH_2$ | |
| Cl | $5\text{-}CH(CH_3)_2$ | O | $CH_2$ | |
| Cl | $4\text{-}CH_3$ | O | $CH_2$ | |
| Cl | 4-F | O | $CH_2$ | |
| Cl | 5-Br | O | $CH_2$ | |
| Cl | $6\text{-}CH_3$ | O | $CH_2$ | |
| $NO_2$ | 5-Cl | O | $CH_2$ | |
| $NO_2$ | 6-Cl | O | $CH_2$ | 200–202° |
| $NO_2$ | 5-F | O | $CH_2$ | |
| Cl | $5\text{-}CH(CH_3)C_2H_5$ | O | $CH_2$ | |
| Br | 5-F | O | $CH_2$ | |
| $SCH_3$ | 5-Cl | O | $CH_2$ | |
| Cl | $5\text{-}C_2H_5$ | O | $CH_2$ | |
| 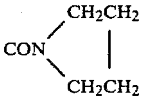 | H | O | $CH_2$ | 122–123° |
| $SCH_3$ | 4-Cl | O | $CH_2$ | |
| $SO_2CH_3$ | H | O | $CH_2$ | 183–187° |
| $SO_2CH_3$ | 6-Cl | O | $CH_2$ | |
| $SCH_3$ | 6-Cl | O | $CH_2$ | |
| $SCH_3$ | $4\text{-}OCH_3$ | O | $CH_2$ | |
| $CF_3$ | 5-Cl | O | $CH_2$ | |
| $CF_3$ | $5\text{-}CH_3$ | O | $CH_2$ | |
| $CF_3$ | 5-F | O | $CH_2$ | |
| $CF_3$ | 4-Cl | O | $CH_2$ | |
| $CF_3$ | $4\text{-}CH_3$ | O | $CH_2$ | |
| $CO_2CH_3$ | $5\text{-}CH_3$ | O | $CH_2$ | |
| $CO_2CH_3$ | $6\text{-}CH_3$ | O | $CH_2$ | |
| $CO_2CH_3$ | 5-Cl | O | $CH_2$ | |
| $CO_2CH_3$ | 3-Cl | O | $CH_2$ | |
| $CO_2CH_3$ | 6-Cl | O | $CH_2$ | |
| $CO_2CH_3$ | $4\text{-}CH_3$ | O | $CH_2$ | |
| $SO_2CH_2CH_3$ | H | O | $CH_2$ | |
| $SO_2CH_2CH{=}CH_2$ | H | O | $CH_2$ | |
| $SOCH_3$ | H | O | $CH_2$ | |
| $SOCH_2CH_3$ | 5-Cl | O | $CH_2$ | |
| 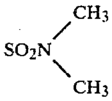 | H | O | $CH_2$ | 207–208° (d) |

TABLE I-A-continued

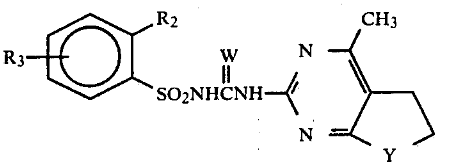

| R2 | R3 | W | Y | m.p. |
|---|---|---|---|---|
| 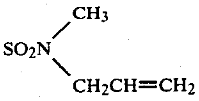 | H | O | $CH_2$ | |
| 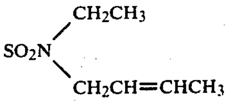 | 6-Cl | O | $CH_2$ | |
| 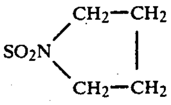 | 5-F | O | $CH_2$ | |
| $SO_2CH_2CH_2CH_3$ | H | O | $CH_2$ | 189–190° |
| 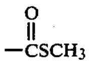 | H | O | $CH_2$ | 179–180° |
| 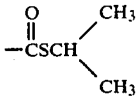 | 5-$OCH_3$ | O | $CH_2$ | |
| 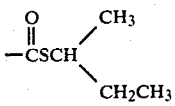 | H | O | $CH_2$ | 175–177° |
| $-SO_2OCH_2CF_3$ | H | O | $CH_2$ | |
| $-SO_2OCH_2CCl_3$ | H | O | $CH_2$ | |
| 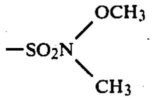 | H | O | $CH_2$ | |
| H | H | O | O | 193–194° (d) |
| —Cl | H | O | O | 202–205° |
| —F | H | O | O | |
| —Br | H | O | O | |
| $-SCH_3$ | H | O | O | |
| $-SO_2CH_3$ | H | O | O | |
| $-CF_3$ | H | O | O | |
| $-NO_2$ | H | O | O | 180–187° |
| $-CO_2CH_3$ | H | O | O | 194.5–197° |
| $-CO_2CH_2CH_3$ | H | O | O | 187–188° |
| $-CO_2CH_2CH_2Cl$ | H | O | O | |
| $-CO_2CH_2CH_2CH_3$ | H | O | O | |
| $-CO_2CH_2CH_2OCH_3$ | H | O | O | |
| $-CO_2CH_2CH_2Br$ | H | O | O | |
| $-SO_2OCH_2CF_3$ | H | O | O | |
| $-SO_2OCH_2CCl_3$ | H | O | O | |
| 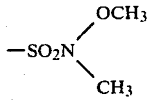 | H | O | O | |
| $-CH_3$ | H | O | O | 170–173° (d) |
| $CO_2CH(CH_3)_2$ | H | O | O | 196–199° |
| $CO_2CH_2CH=CH_2$ | H | O | O | 205–206° |
| $CO_2CH_2CF_3$ | H | O | O | |
| $CO_2(CH_2)_3CH_3$ | H | O | O | 163–165° |
| $CO_2CH(CH_3)CH_2CH_3$ | H | O | O | |
| $CO_2CH(CH_2CH_3)_2$ | H | O | O | |

TABLE I-A-continued

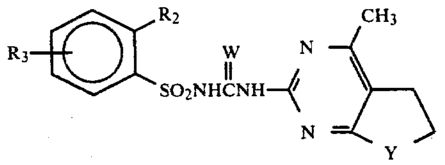

| $R_2$ | $R_3$ | W | Y | m.p. |
|---|---|---|---|---|
| $CO_2CH_2C(CH_3)_3$ | H | O | O | |
| $CO_2CH_2CH{=}CH{-}CH_3$ | H | O | O | |
| $CO_2CH(CH_3)CH{=}CH_2$ | H | O | O | 192–194° |
| $CO_2CH_2CH{=}CH(CH_2)_2CH_3$ | H | O | O | |
| $CO_2(CH_2)_4Cl$ | H | O | O | |
| $CO_2(CH_2)_6Cl$ | H | O | O | |
| 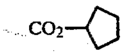 | H | O | O | 169–171° |
| 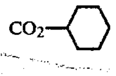 | H | O | O | 178–179° |
| $CO_2(CH_2CH_2O)_2CH_3$ | H | O | O | |
| $CO_2(CH_2CH_2O)_2C_2H_5$ | H | O | O | |
| $CO_2CH_2CH_2CH_2OCH_3$ | H | O | O | |
| $CO_2CH_2CH_2CH_2OC_2H_5$ | H | O | O | |
| $CON(CH_3)_2$ | H | O | O | 189–191° |
| $CON(C_2H_5)_2$ | H | O | O | |
| 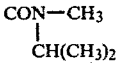 | H | O | O | |
| $CONH_2$ | H | O | O | |
| $CONHCH_3$ | H | O | O | |
| 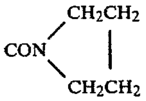 | H | O | O | 192–193° |
| $CO_2CH_2CH_2OC_2H_5$ | H | O | O | |
| $CON(CH(CH_3)_2)_2$ | H | O | O | |
| 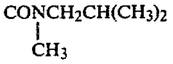 | H | O | O | |
| $CON(CH_2CH_2CH_2CH_3)_2$ | H | O | O | |
| 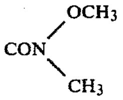 | H | O | O | |
| Cl | 5-Cl | O | O | |
| Cl | 6-Cl | O | O | |
| Cl | 4-Cl | O | O | |
| Cl | 3-Cl | O | O | |
| F | 5-Cl | O | O | |
| F | 3-Cl | O | O | |
| F | 4-Cl | O | O | |
| F | 5-F | O | O | |
| Cl | 5-$OCH_3$ | O | O | |
| Cl | 5-$CH(CH_3)_2$ | O | O | |
| Cl | 4-$CH_3$ | O | O | |
| Cl | 4-F | O | O | |
| Cl | 5-Br | O | O | |
| Cl | 6-$CH_3$ | O | O | |
| $NO_2$ | 5-Cl | O | O | |
| $NO_2$ | 6-Cl | O | O | |
| $NO_2$ | 5-F | O | O | |
| Cl | 5-$CH(CH_3)C_2H_5$ | O | O | |
| Br | 5-F | O | O | |
| $SCH_3$ | 5-Cl | O | O | |
| Cl | 5-$C_2H_5$ | O | O | |
| $SCH_3$ | 4-Cl | O | O | |

TABLE I-A-continued

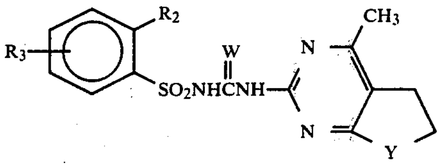

| $R_2$ | $R_3$ | W | Y | m.p. |
|---|---|---|---|---|
| $SO_2CH_3$ | 5-Cl | O | O | |
| $SO_2CH_3$ | 6-Cl | O | O | |
| $SCH_3$ | 6-Cl | O | O | |
| $SCH_3$ | 4-$OCH_3$ | O | O | |
| $CF_3$ | 5-Cl | O | O | |
| $CF_3$ | 5-$CH_3$ | O | O | |
| $CF_3$ | 5-F | O | O | |
| $CF_3$ | 4-Cl | O | O | |
| $CF_3$ | 4-$CH_3$ | O | O | |
| $CO_2CH_3$ | 5-$CH_3$ | O | O | |
| $CO_2CH_3$ | 6-$CH_3$ | O | O | |
| $CO_2CH_3$ | 5-Cl | O | O | |
| $CO_2CH_3$ | 3-Cl | O | O | |
| $CO_2CH_3$ | 6-Cl | O | O | |
| $CO_2CH_3$ | 4-$CH_3$ | O | O | |
| $SOCH_3$ | H | O | O | |
| $SOCH_2CH{=}CH_2$ | 5-Cl | O | O | |
| 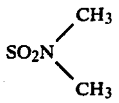 | H | O | O | 188–193° |
| 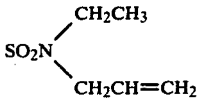 | 5-F | O | O | |
| 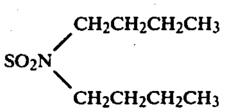 | 6-$CH_3$ | O | O | |
| 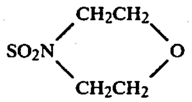 | 4-$OCH_3$ | O | O | |
| 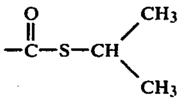 | H | O | O | |
| 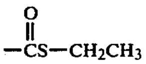 | 5-Cl | O | O | |
| $SO_2N(C_2H_5)_2$ | H | O | O | |
| 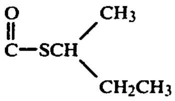 | H | O | O | |
| H | H | S | O | |
| $CH_3$ | H | S | O | |
| $OCH_3$ | H | S | O | |
| Cl | H | S | O | 190–191° (d) |
| F | H | S | O | |
| $CF_3$ | H | S | O | |
| $NO_2$ | H | S | O | |
| $CO_2CH_3$ | H | S | O | |
| $CO_2(CH_2)_3CH_3$ | H | S | O | |
| $CO_2(CH_2)_3Cl$ | H | S | O | |
| $CO_2CH_2CH_2OCH_3$ | H | S | O | |

TABLE I-A-continued

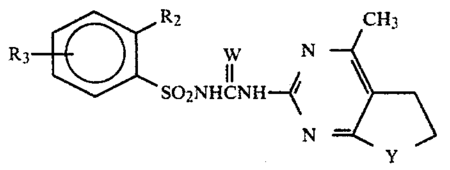

| $R_2$ | $R_3$ | W | Y | m.p. |
|---|---|---|---|---|
| O<br>‖<br>$CSCH_2CH_3$ | H | S | O | |
| $CON(C_2H_5)_2$ | H | S | O | |
| $CONHCH_3$ | H | S | O | |
| $CON(OCH_3)CH_3$ | H | S | O | |
| $SO_2N(C_2H_5)_2$ | H | S | O | |
| $SO_2OCH_2Cl_3$ | H | S | O | |
| Cl | 5-Cl | S | O | |
| $OCH_3$ | 5-$OCH_3$ | S | O | |
| $CO_2CH_3$ | 4-$CH_3$ | S | O | |
| F | 5-F | S | O | |
| Cl | 6-$CH_3$ | S | O | |

TABLE I-B

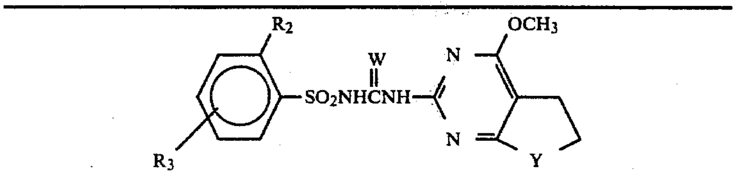

| $R_2$ | $R_3$ | W | Y | m.p. |
|---|---|---|---|---|
| Cl | H | O | $CH_2$ | 224° |
| Cl | 5-Cl | O | $CH_2$ | 231.5-232° |
| $NO_2$ | H | O | $CH_2$ | 211-212° |
| $CO_2CH_3$ | H | O | $CH_2$ | 169-184° |
| $CO_2CH(CH_3)_2$ | H | O | $CH_2$ | 207-209° |
| $-F$ | H | O | $CH_2$ | |
| $-Br$ | H | O | $CH_2$ | |
| $-SCH_3$ | H | O | $CH_2$ | |
| $-SO_2CH_3$ | H | O | $CH_2$ | 225-230° |
| $-CF_3$ | H | O | $CH_2$ | |
| $-CO_2CH_2CH_3$ | H | O | $CH_2$ | 178-179° |
| $-CO_2CH_2CH_2Cl$ | H | O | $CH_2$ | |
| $-CO_2CH_2CH_2CH_3$ | H | O | $CH_2$ | |
| $-CO_2CH_2CH_2OCH_3$ | H | O | $CH_2$ | |
| $CO_2CH_2CH{=}CH_2$ | H | O | $CH_2$ | 137-140° |
| $CO_2CH_2CF_3$ | H | O | $CH_2$ | |
| $CO_2(CH_2)_3CH_3$ | H | O | $CH_2$ | 149-151° |
| $CO_2(CH_2)_5CH_3$ | H | O | $CH_2$ | |
| $CO_2CH(CH_3)CH_2CH_3$ | H | O | $CH_2$ | |
| $CO_2CH(CH_2CH_3)_2$ | H | O | $CH_2$ | |
| $CO_2CH_2C(CH_3)_3$ | H | O | $CH_2$ | |
| $CO_2CH_2CH{=}CH{-}CH_3$ | H | O | $CH_2$ | |
| H | H | O | $CH_2$ | |
| $CO_2CH(CH_3)CH{=}CH_2$ | H | O | $CH_2$ | 176-177° |
| $CO_2CH_2CH{=}CH(CH_2)_2CH_3$ | H | O | $CH_2$ | |
| $CO_2(CH_2)_4Cl$ | H | O | $CH_2$ | |
| $CO_2(CH_2)_6Cl$ | H | O | $CH_2$ | |
| $CO_2$— 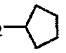 | H | O | $CH_2$ | 174-175° |
| $CO_2$— 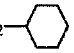 | H | O | $CH_2$ | 171-172° |
| $CO_2(CH_2CH_2O)_2CH_3$ | H | O | $CH_2$ | |
| $CO_2(CH_2CH_2O)_2C_2H_5$ | H | O | $CH_2$ | |
| $CO_2CH_2CH_2CH_2OCH_3$ | H | O | $CH_2$ | |
| $CO_2CH_2CH_2CH_2OC_2H_5$ | H | O | $CH_2$ | |
| $CON(CH_3)_2$ | H | O | $CH_2$ | 177-178° |
| $CON(C_2H_5)_2$ | H | O | $CH_2$ | 207-208° |

TABLE I-B-continued

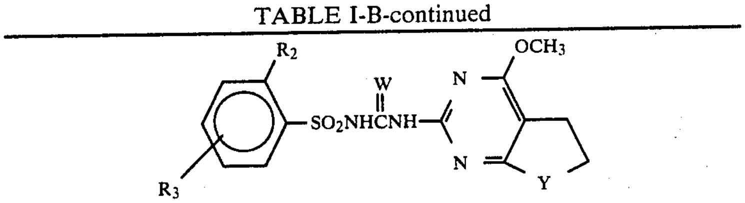

| $R_2$ | $R_3$ | W | Y | m.p. |
|---|---|---|---|---|
| 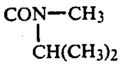 | H | O | $CH_2$ | |
| $CON(CH(CH_3)_2)_2$ | H | O | $CH_2$ | |
| 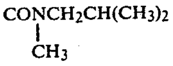 | H | O | $CH_2$ | |
| $CON(CH_2CH_2CH_2CH_3)_2$ | H | O | $CH_2$ | |
| 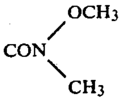 | H | O | $CH_2$ | |
| 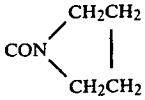 | H | O | $CH_2$ | 194–195° |
| 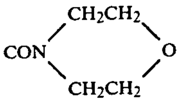 | H | O | $CH_2$ | 193–194° |
| Cl | 6-Cl | O | $CH_2$ | |
| Cl | 4-Cl | O | $CH_2$ | |
| Cl | 3-Cl | O | $CH_2$ | |
| F | 5-Cl | O | $CH_2$ | |
| F | 3-Cl | O | $CH_2$ | |
| F | 4-Cl | O | $CH_2$ | |
| F | 5-F | O | $CH_2$ | |
| Cl | 5-$OCH_3$ | O | $CH_2$ | |
| Cl | 5-$CH(CH_3)_2$ | O | $CH_2$ | |
| Cl | 4-$CH_3$ | O | $CH_2$ | |
| Cl | 4-F | O | $CH_2$ | |
| Cl | 5-Br | O | $CH_2$ | |
| Cl | 6-$CH_3$ | O | $CH_2$ | |
| $NO_2$ | 5-Cl | O | $CH_2$ | |
| $NO_2$ | 6-Cl | O | $CH_2$ | 197–198° |
| $NO_2$ | 5-F | O | $CH_2$ | |
| Cl | 5-$CH(CH_3)C_2H_5$ | O | $CH_2$ | |
| Br | 5-F | O | $CH_2$ | |
| $SCH_3$ | 5-Cl | O | $CH_2$ | |
| $SCH_3$ | 4-Cl | O | $CH_2$ | |
| $SO_2CH_3$ | 5-Cl | O | $CH_2$ | |
| $SO_2CH_3$ | 6-Cl | O | $CH_2$ | |
| $SCH_3$ | 6-Cl | O | $CH_2$ | |
| $SCH_3$ | 4-$OCH_3$ | O | $CH_2$ | |
| $CF_3$ | 5-Cl | O | $CH_2$ | |
| $CF_3$ | 5-$CH_3$ | O | $CH_2$ | |
| $CF_3$ | 5-F | O | $CH_2$ | |
| $CF_3$ | 4-Cl | O | $CH_2$ | |
| $CF_3$ | 4-$CH_3$ | O | $CH_2$ | |
| $CO_2CH_3$ | 5-$CH_3$ | O | $CH_2$ | |
| $CO_2CH_3$ | 6-$CH_3$ | O | $CH_2$ | |
| $CO_2CH_3$ | 5-Cl | O | $CH_2$ | |
| $CO_2CH_3$ | 3-Cl | O | $CH_2$ | |
| $CO_2CH_3$ | 6-Cl | O | $CH_2$ | |
| $CO_2CH_3$ | 4-$CH_3$ | O | $CH_2$ | |
| $SOCH_3$ | H | O | $CH_2$ | |
| $SOCH_3$ | 5-Br | O | $CH_2$ | |
| 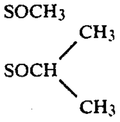 | 6-$CH_3$ | O | $CH_2$ | |

TABLE I-B-continued

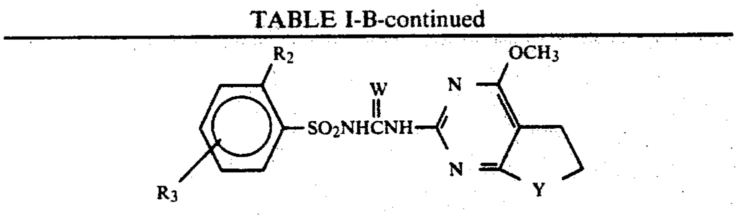

| $R_2$ | $R_3$ | W | Y | m.p. |
|---|---|---|---|---|
| 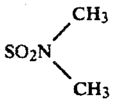 | H | O | $CH_2$ | |
| 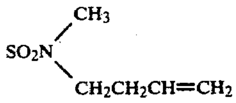 | H | O | $CH_2$ | |
| 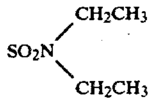 | 5-Cl | O | $CH_2$ | |
| 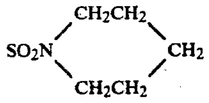 | 4-$OCH_3$ | O | $CH_2$ | |
| 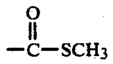 | H | O | $CH_2$ | 170–171° |
| 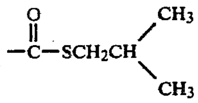 | 3-F | O | $CH_2$ | |
| 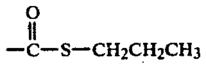 | 5-$CH_2CH_3O$ | $CH_2$ | | |
| 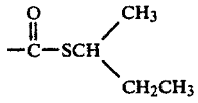 | H | O | $CH_2$ | |
| $SO_2CH_2CH_2CH_3$ | H | O | $CH_2$ | 207–212° |
| 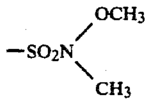 | H | O | $CH_2$ | |
| $-SO_2OCH_2CF_3$ | 5-Cl | O | $CH_2$ | |
| $-SO_2OCH_2CCl_3$ | 3-F | O | $CH_2$ | |
| Cl | H | O | O | 219–223° |
| Cl | 5-Cl | O | O | |
| $NO_2$ | H | O | O | |
| $CO_2CH_3$ | H | O | O | 203–206° |
| $CO_2CH(CH_3)_2$ | H | O | O | 222–224° |
| $-F$ | H | O | O | |
| $-Br$ | H | O | O | |
| $-SCH_3$ | H | O | O | |
| $-SO_2CH_3$ | H | O | O | |
| $-CF_3$ | H | O | O | |
| $-CO_2CH_2CH_3$ | H | O | O | 211–214° |
| $-CO_2CH_2CH_2Cl$ | H | O | O | |
| $-CO_2CH_2CH_2CH_3$ | H | O | O | |
| $-CO_2CH_2CH_2OCH_3$ | H | O | O | |
| $CO_2CH_2CH{=}CH_2$ | H | O | O | 193–195° |
| $CO_2CH_2CF_3$ | H | O | O | |
| $CO_2(CH_2)_3CH_3$ | H | O | O | 168–171° |
| $CO_2(CH_2)_5CH_3$ | H | O | O | |
| $CO_2CH(CH_3)CH_2CH_3$ | H | O | O | |
| $CO_2CH(CH_2CH_3)_2$ | H | O | O | |

TABLE I-B-continued

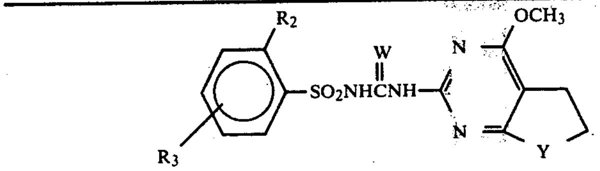

| $R_2$ | $R_3$ | W | Y | m.p. |
|---|---|---|---|---|
| $CO_2CH_2C(CH_3)_3$ | H | O | O | |
| $CO_2CH_2CH{=}CH{-}CH_3$ | H | O | O | |
| H | H | O | O | |
| $SO_2CH_2CH_2CH_3$ | H | O | O | |
| $CO_2CH(CH_3)CH{=}CH_2$ | H | O | O | 182–185° |
| $CO_2CH_2CH{=}CH(CH_2)_2CH_3$ | H | O | O | |
| $CO_2(CH_2)_4Cl$ | H | O | O | |
| $CO_2(CH_2)_6Cl$ | H | O | O | |
| 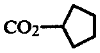 | H | O | O | 195–197° |
| 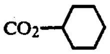 | H | O | O | 171–173° |
| $CO_2(CH_2CH_2O)_2CH_3$ | H | O | O | |
| $CO_2(CH_2CH_2O)_2C_2H_5$ | H | O | O | |
| $CO_2CH_2CH_2CH_2OCH_3$ | H | O | O | |
| $CO_2CH_2CH_2CH_2OC_2H_5$ | H | O | O | |
| $CON(CH_3)_2$ | H | O | O | 184–186° |
| $CON(C_2H_5)_2$ | H | O | O | 188–191° |
| 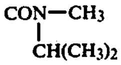 | H | O | O | |
| $CON(CH(CH_3)_2)_2$ | H | O | O | |
| 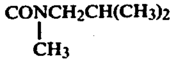 | H | O | O | |
| $CON(CH_2CH_2CH_2CH_3)_2$ | H | O | O | |
| 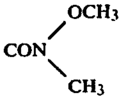 | H | O | O | |
| 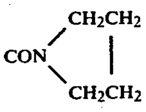 | H | O | O | 196–197° |
| 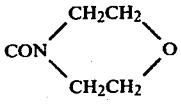 | H | O | O | 190–191° |
| Cl | 6-Cl | O | O | |
| Cl | 4-Cl | O | O | |
| Cl | 3-Cl | O | O | |
| F | 5-Cl | O | O | |
| F | 3-Cl | O | O | |
| F | 4-Cl | O | O | |
| F | 5-F | O | O | |
| Cl | 5-$OCH_3$ | O | O | |
| Cl | 5-$CH(CH_3)_2$ | O | O | |
| Cl | 4-$CH_3$ | O | O | |
| Cl | 4-F | O | O | |
| Cl | 5-Br | O | O | |
| Cl | 6-$CH_3$ | O | O | |
| $NO_2$ | 5-Cl | O | O | |
| $NO_2$ | 6-Cl | O | O | |
| $NO_2$ | 5-F | O | O | |
| Cl | 5-$CH(CH_3)C_2H_5$ | O | O | |
| Br | 5-F | O | O | |
| $SCH_3$ | 5-Cl | O | O | |

TABLE I-B-continued
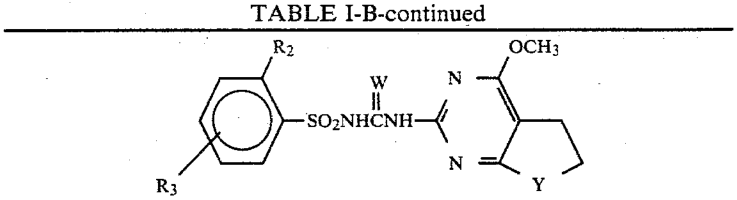
| R2 | R3 | W | Y | m.p. |
|---|---|---|---|---|
| $SCH_3$ | 4-Cl | O | O | |
| $SO_2CH_3$ | 5-Cl | O | O | |
| $SO_2CH_3$ | 6-Cl | O | O | |
| $SCH_3$ | 6-Cl | O | O | |
| $SCH_3$ | 4-$OCH_3$ | O | O | |
| $CF_3$ | 5-Cl | O | O | |
| $CF_3$ | 5-$CH_3$ | O | O | |
| $CF_3$ | 5-F | O | O | |
| $CF_3$ | 4-Cl | O | O | |
| $CF_3$ | 4-$CH_3$ | O | O | |
| $CO_2CH_3$ | 5-$CH_3$ | O | O | |
| $CO_2CH_3$ | 6-$CH_3$ | O | O | |
| $CO_2CH_3$ | 5-Cl | O | O | |
| $CO_2CH_3$ | 3-Cl | O | O | |
| $CO_2CH_3$ | 6-Cl | O | O | |
| $CO_2CH_3$ | 4-$CH_3$ | O | O | |
| $SOCH_3$ | H | O | O | |
| $SOCH_3$ | 5-Cl | O | O | |
| $SOCH_2CH{=}CH_3$ | 6-F | O | O | |
| 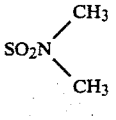 | H | O | O | |
| 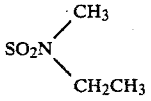 | H | O | O | |
| 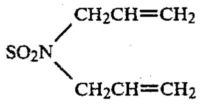 | 5-$OCH_3$ | O | O | |
| 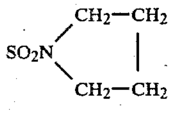 | 3-Br | O | O | |
| 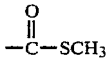 | H | O | O | 181–182° |
| 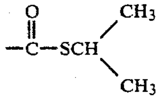 | 5-F | O | O | |
| 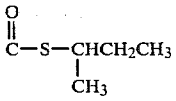 | H | O | O | |
| 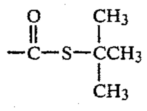 | 6-$CH_3$ | O | O | |
| $-SO_2OCH_2CF_3$ | H | O | O | |
| $-SO_2OCH_2CCl_3$ | 5-Cl | O | O | |
| 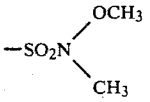 | H | O | O | |

TABLE I-B-continued

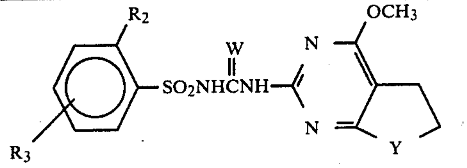

| R2 | R3 | W | Y | m.p. |
|---|---|---|---|---|
| $CH_3$ | H | S | O | |
| Cl | H | S | O | |
| $NO_2$ | H | S | O | |
| $CO_2CH_2CH_3$ | H | S | O | |
| $SO_2CH_3$ | H | S | O | |
| $CF_3$ | H | S | O | |
| $CO_2(CH_2)_3OCH_3$ | H | S | O | |
| $CO_2CH_2CH_2Cl$ | H | S | O | |
| $CO_2CH_2CH{=}CHCH_3$ | H | S | O | |
| $CON(OCH_3)CH_3$ | H | S | O | |
| $CON(CH_3)[CH(CH_3)_2]$ | H | S | O | |
| 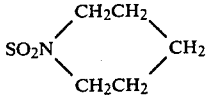 | H | S | O | |
| 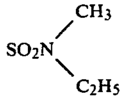 | H | S | O | |
| 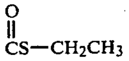 | H | S | O | |
| $SO_2OCH_2CCl_3$ | H | S | O | |
| Cl | 5-Cl | S | O | |
| $NO_2$ | 5-Cl | S | O | |
| $CO_2CH_3$ | 4-Br | S | O | |
| $SOC_2H_5$ | 4-F | S | O | |
| 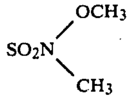 | 5-Cl | S | O | |
| $OCH_3$ | 5-$OCH_3$ | S | O | |
| 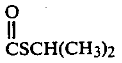 | 4-$CH_3$ | S | O | |
| $SO_2OCH_2CF_3$ | 5-Cl | S | O | |

TABLE I-C

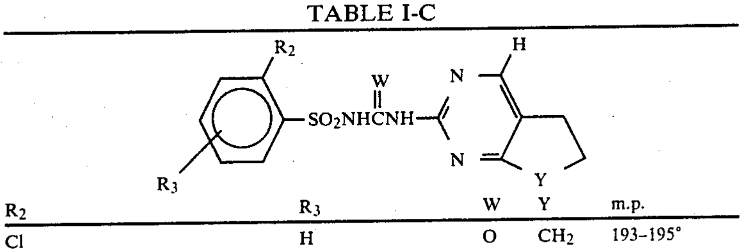

| R2 | R3 | W | Y | m.p. |
|---|---|---|---|---|
| Cl | H | O | $CH_2$ | 193–195° |
| Cl | 5-Cl | O | $CH_2$ | |
| $NO_2$ | H | O | $CH_2$ | 179–184° (d) |
| $CO_2CH_3$ | H | O | $CH_2$ | 208–209° |
| $CO_2CH(CH_3)_2$ | H | O | $CH_2$ | |
| —F | H | O | $CH_2$ | |
| —Br | H | O | $CH_2$ | |
| —$SCH_3$ | H | O | $CH_2$ | |
| —$SO_2CH_3$ | H | O | $CH_2$ | |
| —$CF_3$ | H | O | $CH_2$ | |
| —$CO_2CH_2CH_3$ | H | O | $CH_2$ | |
| —$CO_2CH_2CH_2Cl$ | H | O | $CH_2$ | |

TABLE I-C-continued

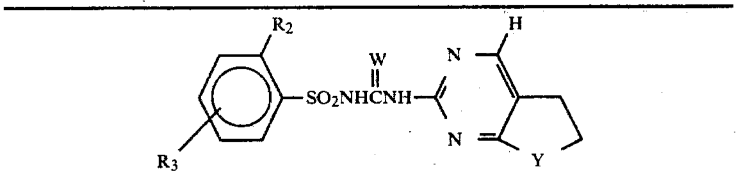

| $R_2$ | $R_3$ | W | Y | m.p. |
|---|---|---|---|---|
| $-CO_2CH_2CH_2CH_3$ | H | O | $CH_2$ | |
| $-CO_2CH_2CH_2OCH_3$ | H | O | $CH_2$ | |
| $CO_2CH(CH_3)_2$ | H | O | $CH_2$ | |
| $CO_2CH_2CH{=}CH_2$ | H | O | $CH_2$ | |
| $CO_2CH_2CF_3$ | H | O | $CH_2$ | |
| $CO_2(CH_2)_3CH_3$ | H | O | $CH_2$ | |
| $CO_2(CH_2)_5CH_3$ | H | O | $CH_2$ | |
| $CO_2CH(CH_3)CH_2CH_3$ | H | O | $CH_2$ | |
| $CO_2CH(CH_2CH_3)_2$ | H | O | $CH_2$ | |
| $CO_2CH_2C(CH_3)_3$ | H | O | $CH_2$ | |
| $CO_2CH_2CH{=}CH-CH_3$ | H | O | $CH_2$ | |
| H | H | O | $CH_2$ | |
| $CO_2CH(CH_3)CH{=}CH_2$ | H | O | $CH_2$ | |
| $CO_2CH_2CH{=}CH(CH_2)_2CH_3$ | H | O | $CH_2$ | |
| $CO_2(CH_2)_4Cl$ | H | O | $CH_2$ | |
| $CO_2(CH_2)_6Cl$ | H | O | $CH_2$ | |
| $CO_2$— 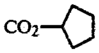 | H | O | $CH_2$ | |
| $CO_2$— 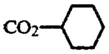 | H | O | $CH_2$ | |
| $CO_2(CH_2CH_2O)_2CH_3$ | H | O | $CH_2$ | |
| $CO_2(CH_2CH_2O)_2C_2H_5$ | H | O | $CH_2$ | |
| $CO_2CH_2CH_2CH_2OCH_3$ | H | O | $CH_2$ | |
| $CO_2CH_2CH_2CH_2OC_2H_5$ | H | O | $CH_2$ | |
| $CON(CH_3)_2$ | H | O | $CH_2$ | |
| $CON(C_2H_5)_2$ | H | O | $CH_2$ | |
| $CON-CH_3$<br>$\vert$<br>$CH(CH_3)_2$ | H | O | $CH_2$ | |
| $CON(CH(CH_3)_2)_2$ | H | O | $CH_2$ | |
| $CONCH_2CH(CH_3)_2$<br>$\vert$<br>$CH_3$ | H | O | $CH_2$ | |
| $CON(CH_2CH_2CH_2CH_3)_2$ | H | O | $CH_2$ | |
| $OCH_3$<br>$CON$<br>$CH_3$ | H | O | $CH_2$ | |
| Cl | 6-Cl | O | $CH_2$ | |
| Cl | 4-Cl | O | $CH_2$ | |
| Cl | 3-Cl | O | $CH_2$ | |
| F | 5-Cl | O | $CH_2$ | |
| F | 3-Cl | O | $CH_2$ | |
| F | 4-Cl | O | $CH_2$ | |
| F | 5-F | O | $CH_2$ | |
| Cl | 5-$OCH_3$ | O | $CH_2$ | |
| Cl | 5-$CH(CH_3)_2$ | O | $CH_2$ | |
| Cl | 4-$CH_3$ | O | $CH_2$ | |
| Cl | 4-F | O | $CH_2$ | |
| Cl | 5-Br | O | $CH_2$ | |
| Cl | 6-$CH_3$ | O | $CH_2$ | |
| $NO_2$ | 5-Cl | O | $CH_2$ | |
| $NO_2$ | 6-Cl | O | $CH_2$ | |
| $NO_2$ | 5-F | O | $CH_2$ | |
| Cl | 5-$CH(CH_3)C_2H_5$ | O | $CH_2$ | |
| Br | 5-F | O | $CH_2$ | |
| $SCH_3$ | 5-Cl | O | $CH_2$ | |
| $SCH_3$ | 4-Cl | O | $CH_2$ | |
| $SO_2CH_3$ | 5-Cl | O | $CH_2$ | |
| $SO_2CH_3$ | 6-Cl | O | $CH_2$ | |
| $SCH_3$ | 6-Cl | O | $CH_2$ | |

TABLE I-C-continued

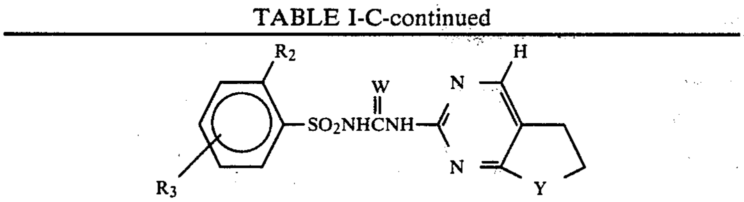

| R2 | R3 | W | Y | m.p. |
|---|---|---|---|---|
| $SCH_3$ | 4-$OCH_3$ | O | $CH_2$ | |
| $CF_3$ | 5-Cl | O | $CH_2$ | |
| $CF_3$ | 5-$CH_3$ | O | $CH_2$ | |
| $CF_3$ | 5-F | O | $CH_2$ | |
| $CF_3$ | 4-Cl | O | $CH_2$ | |
| $CF_3$ | 4-$CH_3$ | O | $CH_2$ | |
| $CO_2CH_3$ | 5-$CH_3$ | O | $CH_2$ | |
| $CO_2CH_3$ | 6-$CH_3$ | O | $CH_2$ | |
| $CO_2CH_3$ | 5-Cl | O | $CH_2$ | |
| $CO_2CH_3$ | 3-Cl | O | $CH_2$ | |
| $CO_2CH_3$ | 6-Cl | O | $CH_2$ | |
| $CO_2CH_3$ | 4-$CH_3$ | O | $CH_2$ | |
| $SOCH_3$ | H | O | $CH_2$ | |
| $SOCH_3$ | 5-Br | O | $CH_2$ | |
| 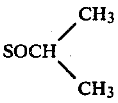 | 6-$CH_3$ | O | $CH_2$ | |
| 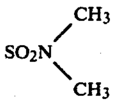 | H | O | $CH_2$ | |
| 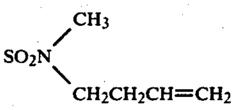 | H | O | $CH_2$ | |
| 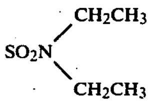 | 5-Cl | O | $CH_2$ | |
| 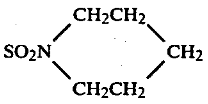 | 4-$OCH_3$ | O | $CH_2$ | |
| 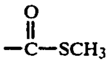 | H | O | $CH_2$ | |
| 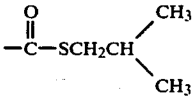 | 3-F | O | $CH_2$ | |
| 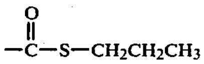 | 5-$CH_2CH_3$ | O | $CH_2$ | |
| 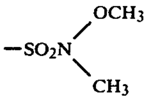 | 5-Cl | O | $CH_2$ | |
| Cl | H | O | O | 180–183° (d) |
| Cl | 5-Cl | O | O | |
| $NO_2$ | H | O | O | |
| $CO_2CH_3$ | H | O | O | 206–209° (d) |
| $CO_2CH(CH_3)_2$ | H | O | O | |
| —F | H | O | O | |
| —Br | H | O | O | |
| —$SCH_3$ | H | O | O | |
| —$SO_2CH_3$ | H | O | O | |
| —$CF_3$ | H | O | O | |

TABLE I-C-continued

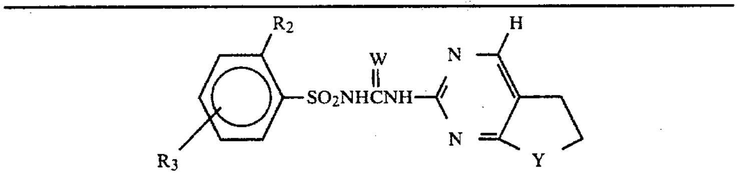

| $R_2$ | $R_3$ | W | Y | m.p. |
|---|---|---|---|---|
| $-CO_2CH_2CH_3$ | H | O | O | |
| $-CO_2CH_2CH_2Cl$ | H | O | O | |
| $-CO_2CH_2CH_2CH_3$ | H | O | O | |
| $-CO_2CH_2CH_2OCH_3$ | H | O | O | |
| $-SO_2OCH_2CF_3$ | H | O | $CH_2$ | |
| $CO_2CH_2CH=CH_2$ | H | O | O | |
| $CO_2CH_2CF_3$ | H | O | O | |
| $CO_2(CH_2)_3CH_3$ | H | O | O | |
| $CO_2(CH_2)_5CH_3$ | H | O | O | |
| $CO_2CH(CH_3)CH_2CH_3$ | H | O | O | |
| $CO_2CH(CH_2CH_3)_2$ | H | O | O | |
| $CO_2CH_2C(CH_3)_3$ | H | O | O | |
| $CO_2CH_2CH=CH-CH_3$ | H | O | O | |
| H | H | O | O | |
| 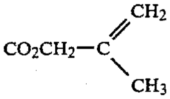 | H | O | O | |
| $CO_2CH_2CH=CH(CH_2)_2CH_3$ | H | O | O | |
| $CO_2(CH_2)_4Cl$ | H | O | O | |
| $CO_2(CH_2)_6Cl$ | H | O | O | |
| 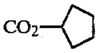 | H | O | O | |
| 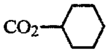 | H | O | O | |
| $CO_2(CH_2CH_2O)_2CH_3$ | H | O | O | |
| $CO_2(CH_2CH_2O)_2C_2H_5$ | H | O | O | |
| $CO_2CH_2CH_2CH_2OCH_3$ | H | O | O | |
| $CO_2CH_2CH_2CH_2OC_2H_5$ | H | O | O | |
| $CON(CH_3)_2$ | H | O | O | |
| $CON(C_2H_5)_2$ | H | O | O | |
| 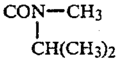 | H | O | O | |
| $CON(CH(CH_3)_2)_2$ | H | O | O | |
| 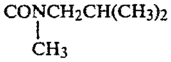 | H | O | O | |
| $CON(CH_2CH_2CH_2CH_3)_2$ | H | O | O | |
| 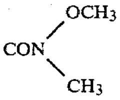 | H | O | O | |
| Cl | 6-Cl | O | O | |
| Cl | 4-Cl | O | O | |
| Cl | 3-Cl | O | O | |
| F | 5-Cl | O | O | |
| F | 3-Cl | O | O | |
| F | 4-Cl | O | O | |
| F | 5-F | O | O | |
| Cl | $5-OCH_3$ | O | O | |
| Cl | $5-CH(CH_3)_2$ | O | O | |
| Cl | $4-CH_3$ | O | O | |
| Cl | 4-F | O | O | |
| Cl | 5-Br | O | O | |
| Cl | $6-CH_3$ | O | O | |
| $NO_2$ | 5-Cl | O | O | |
| $NO_2$ | 6-Cl | O | O | |
| $NO_2$ | 5-F | O | O | |

TABLE I-C-continued
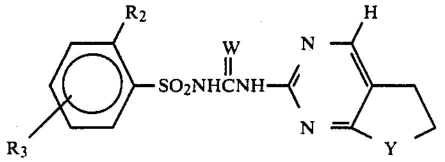
| $R_2$ | $R_3$ | W | Y | m.p. |
|---|---|---|---|---|
| Cl | 5-$CH(CH_3)C_2H_5$ | O | O | |
| Br | 5-F | O | O | |
| $SCH_3$ | 5-Cl | O | O | |
| $SCH_3$ | 4-Cl | O | O | |
| $SO_2CH_3$ | 5-Cl | O | O | |
| $SO_2CH_3$ | 6-Cl | O | O | |
| $SCH_3$ | 6-Cl | O | O | |
| $SCH_3$ | 4-$OCH_3$ | O | O | |
| $CF_3$ | 5-Cl | O | O | |
| $CF_3$ | 5-$CH_3$ | O | O | |
| $CF_3$ | 5-F | O | O | |
| $CF_3$ | 4-Cl | O | O | |
| $CF_3$ | 4-$CH_3$ | O | O | |
| $CO_2CH_3$ | 5-$CH_3$ | O | O | |
| $CO_2CH_3$ | 6-$CH_3$ | O | O | |
| $CO_2CH_3$ | 5-Cl | O | O | |
| $CO_2CH_3$ | 3-Cl | O | O | |
| $CO_2CH_3$ | 6-Cl | O | O | |
| $CO_2CH_3$ | 4-$CH_3$ | O | O | |
| $SOCH_3$ | H | O | O | |
| $SOCH_3$ | 5-Cl | O | O | |
| $SOCH_2CH{=}CH_3$ | 6-F | O | O | |
| 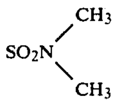 | H | O | O | |
| 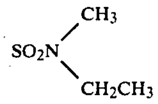 | H | O | O | |
| 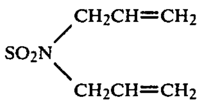 | 5-$OCH_3$ | O | O | |
| 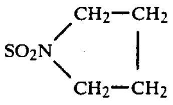 | 3-Br | O | O | |
| 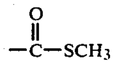 | H | O | O | |
| 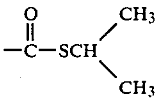 | 5-F | O | O | |
| 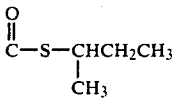 | H | O | O | |
| 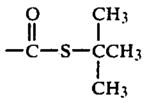 | 6-$CH_3$ | O | O | |
| 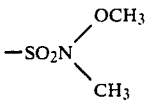 | H | O | O | |
| $-SO_2OCH_2CCl_3$ | 3-Cl | O | O | |

TABLE I-C-continued

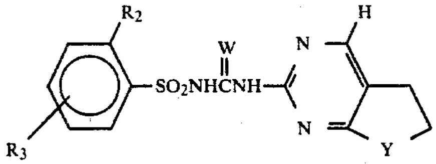

| $R_2$ | $R_3$ | W | Y | m.p. |
|---|---|---|---|---|
| H | H | S | O | |
| Cl | H | S | O | 104–108° (d) |
| F | H | S | O | |
| $NO_2$ | H | S | O | |
| $SCH_3$ | H | S | O | |
| $OCH_3$ | H | S | O | |
| $SOCH(CH_3)_2$ | H | S | O | |
| $CF_3$ | H | S | O | |
| $CO_2CH_3$ | H | S | O | |
| $CO_2CH_2CH_2Br$ | H | S | O | |
| $CO_2CH_2CH_2CH_2OCH_3$ | H | S | O | |
| $CO_2CH_2CCl_3$ | H | S | O | |
| $CO_2CH_2CH{=}CH_2$ | H | S | O | |
| $CO_2CH(CH_3)_2$ | H | S | O | |
| $CON(OCH_3)CH_3$ | H | S | O | |
| $CON[CH(CH_3)_2]_2$ | H | S | O | |
| $CH_2CH_2$ / CON $CH_2$ \ $CH_2CH_2$ | H | S | O | |
| O ‖ CS—$CH_2CH_2CH_3$ | H | S | O | |
| $SO_2OCH_2CCl_3$ | H | S | O | |
| H | 5-F | S | O | |
| Cl | 5-Cl | S | O | |
| $CO_2CH_3$ | 5-$OCH_3$ | S | O | |
| $NO_2$ | 6-Cl | S | O | |
| $OCH_3$ | 5-$OCH_3$ | S | O | |
| $SO_2N(CH_3)_2$ | 4-Cl | S | O | |
| $CON(CH_3)_2$ | 5-Br | S | O | |
| $SO_2OCH_2CF_3$ | 5-$CH_3$ | S | O | |

TABLE I-D

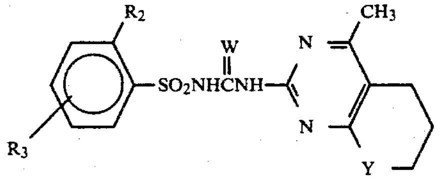

| $R_2$ | $R_3$ | W | Y | m.p. |
|---|---|---|---|---|
| $CO_2CH_3$ | H | O | $CH_2$ | 190.5–192° |
| $CO_2CH_3$ | 3-Cl | O | $CH_2$ | |
| $CO_2CH_3$ | 4-$C_2H_5$ | O | $CH_2$ | |
| $CO_2C_2H_5$ | H | O | $CH_2$ | |
| $CO_2C_2H_5$ | 4-$CH_2CH_2CH_3$ | O | $CH_2$ | |
| $CO_2CH_2CH_2CH_3$ | H | O | $CH_2$ | |
| $CO_2CH_2CH_2CH_3$ | 4-F | O | $CH_2$ | |
| $CO_2CHCH_2CH_3$ \| $CH_3$ | H | O | $CH_2$ | |
| $CO_2CHCH_2CH_3$ \| $CH_3$ | 3-Cl | O | $CH_2$ | |
| $CO_2(CH_2)_4CH{=}CH_2$ | H | O | $CH_2$ | |
| $CO_2$— 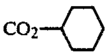 | H | O | $CH_2$ | |
| $CO_2CH_2CH_2OC_2H_5$ | H | O | $CH_2$ | |

TABLE I-D-continued

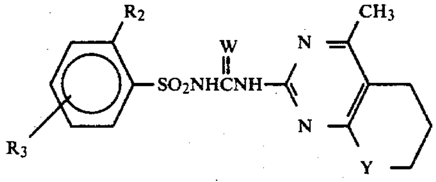

| $R_2$ | $R_3$ | W | Y | m.p. |
|---|---|---|---|---|
| $CO_2(CH_2)_3O$—$CH_3$ | 4-$CH_3$ | O | $CH_2$ | |
| $C_2H_5$ / CON \ $CH(CH_3)_2$ | Cl | O | $CH_2$ | |
| $OCH_3$ / CON \ $CH_3$ | H | O | $CH_2$ | |
| $SO_2N(CH_3)_2$ | H | O | $CH_2$ | |
| $SO_2N(C_2H_5)_2$ | H | O | $CH_2$ | |
| $OCH_3$ / $SO_2N$ \ $CH_3$ | H | O | $CH_2$ | |

TABLE I-D-continued

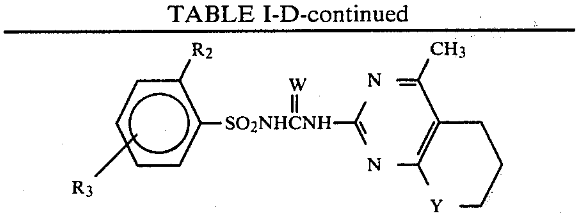

| R2 | R3 | W | Y | m.p. |
|---|---|---|---|---|
| $NO_2$ | H | O | $CH_2$ | 192–196° (d) |
| $COSCH_3$ | H | O | $CH_2$ | |
| 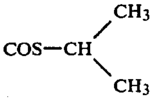 | 5-Cl | O | $CH_2$ | |
| $COSCH_2CH_3$ | 6-$OCH_3$ | O | $CH_2$ | |
| $CO_2CH_3$ | H | O | O | 179–183° |
| $CO_2CH_3$ | 3-Cl | O | O | |
| $CO_2CH_3$ | 4-$C_2H_5$ | O | O | |
| $CO_2C_2H_5$ | H | O | O | 178–182° |
| $CO_2C_2H_5$ | 4-$CH_2CH_2CH_3$ | O | O | |
| $CO_2CH_2CH_2CH_3$ | H | O | O | |
| $CO_2CH_2CH_2CH_3$ | 4-F | O | O | |
| 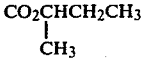 | H | O | O | |
| 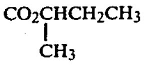 | 3-Cl | O | O | |
| $CO_2(CH_2)_4CH{=}CH_2$ | H | O | O | |
| 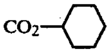 | H | O | O | |
| $CO_2CH_2CH_2OC_2H_5$ | H | O | O | |
| $CO_2(CH_2)_3O{-}CH_3$ | 4-$CH_3$ | O | O | |
| 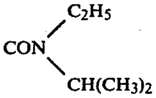 | Cl | O | O | |
| 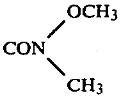 | H | O | O | |
| $COSCH_3$ | H | O | O | |
| 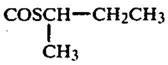 | 3-Br | O | O | |
| $COS{-}CH_2CH_2CH_3$ | 6-Cl | O | O | |
| $SO_2N(CH_3)_2$ | H | O | O | |
| $SO_2N(C_2H_5)_2$ | H | O | O | |
| 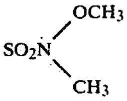 | H | O | O | |
| $CO_2CH_3$ | H | S | O | |
| $CO_2CH(CH_3)_2$ | H | S | O | |
| $CO_2CH_2CH_2OCH_2CH_3$ | H | S | O | |
| $CO_2CH_2CH{=}CHCH_3$ | H | S | O | |
| $CON(OCH_3)CH_3$ | H | S | O | |

TABLE I-D-continued

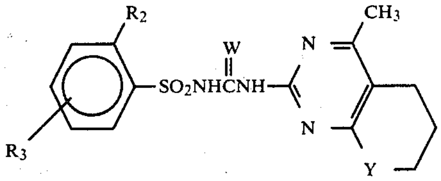

| R2 | R3 | W | Y | m.p. |
|---|---|---|---|---|
| 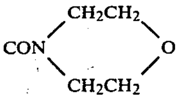 | H | S | O | |
| $SO_2N(C_2H_5)_2$ | H | S | O | |
| 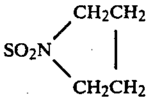 | H | S | O | |
| $CO_2CH_2CH_2CH_2CH_3$ | H | O | O | 128–131° |
| $CO_2CH(CH_3)_2$ | H | O | O | 169–171° |
| $CO_2CH_2CH{=}CH_2$ | H | O | O | 156–159° |
| Cl | H | O | O | 193–195° |
| $CO_2CH_3$ | 5-F | S | O | |
| $CO_2CH_3$ | 5-$OCH_3$ | S | O | |
| $CON(CH_3)_2$ | 6-Cl | S | O | |
| $SO_2N(OCH_3)CH_3$ | 3-Cl | S | O | |
| 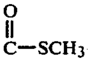 | 4-$CH_3$ | S | O | |

TABLE 1-E

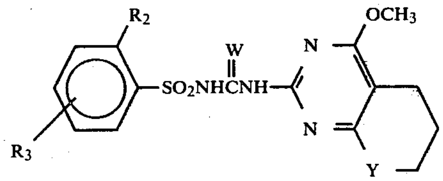

| R2 | R3 | W | Y | m.p. |
|---|---|---|---|---|
| $CO_2CH_3$ | H | O | $CH_2$ | |
| $CO_2CH_3$ | 4-$CH_3O$ | O | $CH_2$ | |
| $CO_2C_2H_5$ | H | O | $CH_2$ | |
| $CO_2C_2H_5$ | Cl | O | $CH_2$ | |
| $CO_2CH(CH_3)_2$ | H | O | $CH_2$ | |
| $CO_2CH_2{-}CH{=}CH_2$ | H | O | $CH_2$ | |
| $CO_2CH_2CH{=}CHCH_2CH_3$ | 5-Br | O | $CH_2$ | |
| 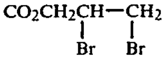 | H | O | $CH_2$ | |
| 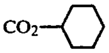 | H | O | $CH_2$ | |
| $CO_2(CH_2CH_2)_2OC_2H_5$ | H | O | $CH_2$ | |
| $CO_2CH_2CH_2CH_2OC_2H_5$ | H | O | $CH_2$ | |
| $CON(CH_2CH_2CH_2CH_3)_2$ | H | O | $CH_2$ | |
| 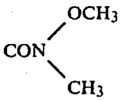 | H | O | $CH_2$ | |
| $COSCH_3$ | H | O | $CH_2$ | |

TABLE 1-E-continued

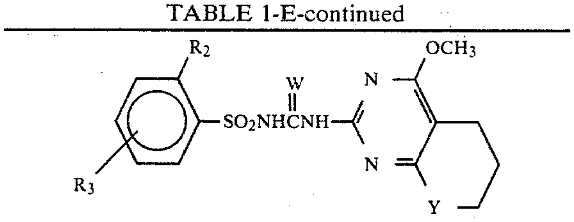

| $R_2$ | $R_3$ | W | Y | m.p. |
|---|---|---|---|---|
| 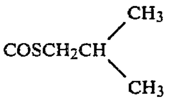 | H | O | $CH_2$ | |
| $COSCH_2CH_2CH_2CH_3$ | 3-Cl | O | $CH_2$ | |
| $SO_2N(CH_3)_2$ | H | O | $CH_2$ | |
| $SO_2N(C_2H_5)_2$ | H | O | $CH_2$ | |
| 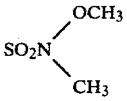 | H | O | $CH_2$ | |
| $CO_2CH_3$ | H | O | O | 206-210° |
| $CO_2CH_3$ | 4-$CH_3O$ | O | O | |
| $CO_2C_2H_5$ | H | O | O | |
| $CO_2C_2H_5$ | Cl | O | O | |
| $CO_2CH(CH_3)_2$ | H | O | O | |
| $CO_2CH_2—CH=CH_2$ | H | O | O | 155-157° |
| $CO_2CH_2CH=CHCH_2CH_3$ | 5-Br | O | O | |
| 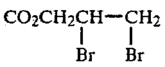 | H | O | O | |
| 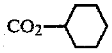 | H | O | O | |
| $CO_2(CH_2CH_2)_2OC_2H_5$ | H | O | O | |
| $CO_2CH_2CH_2CH_2OC_2H_5$ | H | O | O | |
| $CON(CH_2CH_2CH_2CH_3)_2$ | H | O | O | |
| 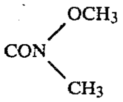 | H | O | O | |
| $COSCH_3$ | H | O | O | |
| 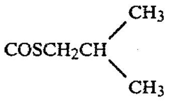 | H | O | O | |
| $CO—SCH_2CH_2CH_3$ | 6-$CH_3$ | O | O | |
| 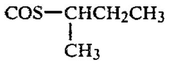 | 3-F | O | O | |
| $SO_2N(CH_3)_2$ | H | O | O | |
| $SO_2N(C_2H_5)_2$ | H | O | O | |
| 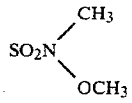 | H | O | O | |
| $CO_2CH_2CH_3$ | H | S | O | |
| $CO_2CH(CH_3)_2$ | H | S | O | |
| $CO_2CH_2CH_2Br$ | H | S | O | |
| $CO_2CH_2CH=CH_2$ | H | S | O | |
| $CO_2(CH_2CH_2O)_2CH_3$ | H | S | O | |
| $CON[CH(CH_3)_2]_2$ | H | S | O | |
| $SO_2N(OCH_3)CH_3$ | H | S | O | |
| $CO_2CH_3$ | 6-$CH_3$ | S | O | |

TABLE 1-E-continued

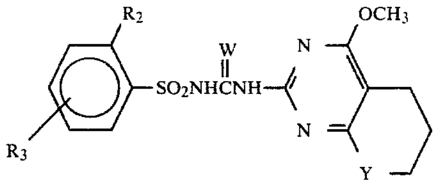

| $R_2$ | $R_3$ | W | Y | m.p. |
|---|---|---|---|---|
| $CO_2CH(CH_3)_2$ | 5-Cl | S | O | |
| $CON(OCH_3)CH_3$ | 5-$OCH_3$ | S | O | |
| $SO_2N(CH_3)_2$ | 4-F | S | O | |
| 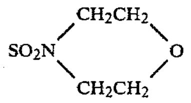 | 3-Br | S | O | |
| $CH_3$ | H | O | O | 226-228° |
| $CO_2CH(CH_3)_2$ | H | O | O | 214-216° |
| $NO_2$ | H | O | O | 203-206° |

The compounds in Table II are prepared by reacting pyridinesulfonylisocyanates or pyridinesulfonylisothiocyanates with the appropriate 2-amino-pyrimidine as illustrated by Examples 6 and 7.

EXAMPLE 6

2-Chloro-3-pyridinesulfonylisocyanate

To 125 ml of dry xylene were added with stirring 20.7 g of 2-chloro-N-(butylcarbamoyl)-3-pyridinesulfonamide. This solution was heated to reflux, and phosgene added until no further uptake of this gas was observed. It was then cooled, filtered and the solvent was removed in vacuo to yield 2-chloro-3-pyridinesulfonylisocyanate as an oil Bp 108°-110° (0.7 mm Hg). This product showed a sharp absorption peak in the infrared region at 2220 $cm^{-1}$.

EXAMPLE 7

2-Chloro-N-[(6,7-dihydro-4-methyl-5H-cyclopentapyrimidin-2-yl)aminocarbonyl]pyridine-3-sulfonamide To a dry, stirred solution of 7.5 g of 6,7-dihydro-4-methyl-5H-cyclopentapyrimidin-2-amine in 200 ml of methylene chloride at ambient temperature and pressure is added 13 g of 2-chloropyrimidine-3-sulfonylisocyanate. The resulting mixture is stirred at reflux for 2 hours and then concentrated at reduced pressure. The residue is triturated with 1-chlorobutane and filtered to yield the desired solid product.

TABLE II-A

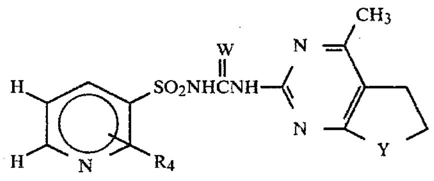

| $R_4$ | W | Y |
|---|---|---|
| 2-F | O | $CH_2$ |
| 2-Br | O | $CH_2$ |
| 2-$CH_3$ | O | $CH_2$ |
| 2-$OCH_3$ | O | $CH_2$ |
| 2-$NO_2$ | O | $CH_2$ |
| 2-$CO_2CH_3$ | O | $CH_2$ |
| 2-$CO_2CH(CH_3)_2$ | O | $CH_2$ |

TABLE II-A-continued

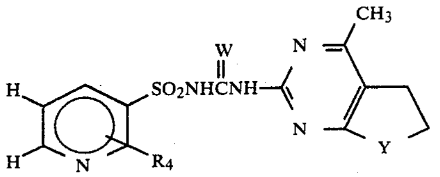

| $R_4$ | W | Y |
|---|---|---|
| $2\text{-}CO_2CHCH_2CH_3$<br>$CH_3$ | O | $CH_2$ |
| $2\text{-}SCH_3$ | O | $CH_2$ |
| 4-Cl | O | $CH_2$ |
| 4-F | O | $CH_2$ |
| 4-Br | O | $CH_2$ |
| $4\text{-}C_2H_5$ | O | $CH_2$ |
| $4\text{-}CH_2CH_2CH_2CH_3$ | O | $CH_2$ |
| $4\text{-}OCH_2CH_2CH_2CH_3$ | O | $CH_2$ |
| $4\text{-}NO_2$ | O | $CH_2$ |
| $4\text{-}CO_2C_2H_5$ | O | $CH_2$ |
| $4\text{-}CO_2CH_2CH_2CH_3$ | O | $CH_2$ |
| $4\text{-}CO_2CH_2CH(CH_3)_2$ | O | $CH_2$ |
| $4\text{-}CO_2(CH_2)_4CH_3$ | O | $CH_2$ |
| $4\text{-}CO_2(CH_2)_5CH_3$ | O | $CH_2$ |
| $4\text{-}SCH_3$ | O | $CH_2$ |
| H | O | $CH_2$ |
| $2\text{-}S(CH_2)_3CH_3$ | O | $CH_2$ |
| 2-F | O | O |
| 2-Br | O | O |
| $2\text{-}CH_3$ | O | O |
| $2\text{-}OCH_3$ | O | O |
| $2\text{-}NO_2$ | O | O |
| $2\text{-}CO_2CH_3$ | O | O |
| $2\text{-}CO_2CH(CH_3)_2$ | O | O |
| $2\text{-}CO_2CHCH_2CH_3$<br>$CH_3$ | O | O |
| $2\text{-}SCH_3$ | O | O |
| 4-Cl | O | O |
| 4-F | O | O |
| 4-Br | O | O |
| $4\text{-}C_2H_5$ | O | O |
| $4\text{-}CH_2CH_2CH_2CH_3$ | O | O |
| $4\text{-}OCH_2CH_2CH_2CH_3$ | O | O |
| $4\text{-}NO_2$ | O | O |
| $4\text{-}CO_2C_2H_5$ | O | O |
| $4\text{-}CO_2CH_2CH_2CH_3$ | O | O |
| $4\text{-}CO_2CH_2CH(CH_3)_2$ | O | O |
| $4\text{-}CO_2(CH_2)_4CH_3$ | O | O |
| $4\text{-}CO_2(CH_2)_5CH_3$ | O | O |
| $4\text{-}SCH_3$ | O | O |
| 2-Cl | O | O |
| $2\text{-}S(CH_2)_3CH_3$ | O | O |
| H | S | O |
| 2-Cl | S | O |
| 2-Br | S | O |
| $2\text{-}CH_3$ | S | O |
| $2\text{-}OCH_3$ | S | O |
| $2\text{-}CO_2CH(CH_3)_2$ | S | O |
| $2\text{-}SCH_3$ | S | O |
| 4-Cl | S | O |
| 4-F | S | O |
| $4\text{-}C_2H_5$ | S | O |
| $4\text{-}OCH(CH_3)_2$ | S | O |
| $4\text{-}NO_2$ | S | O |
| $4\text{-}CO_2CH_3$ | S | O |

TABLE II-B

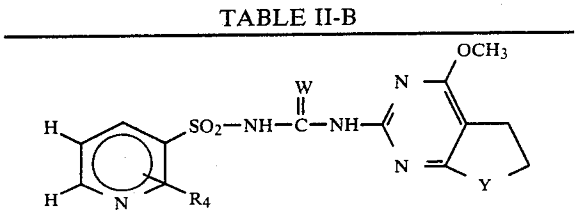

| $R_4$ | W | Y |
|---|---|---|
| 2-Br | O | $CH_2$ |
| $2\text{-}CH_3$ | O | $CH_2$ |
| $2\text{-}CHCH_2CH_3$<br>$CH_3$ | O | $CH_2$ |
| $2\text{-}CH_2CH_2CH_3$ | O | $CH_2$ |
| $2\text{-}OCH_3$ | O | $CH_2$ |
| $2\text{-}NO_2$ | O | $CH_2$ |
| $2\text{-}CO_2CH_3$ | O | $CH_2$ |
| $2\text{-}CO_2(CH_2)_5CH_3$ | O | $CH_2$ |
| $2\text{-}CO_2CH_2CH_3$ | O | $CH_2$ |
| 4-Cl | O | $CH_2$ |
| 4-F | O | $CH_2$ |
| 4-Br | O | $CH_2$ |
| $4\text{-}CH_3$ | O | $CH_2$ |
| $4\text{-}C_2H_5$ | O | $CH_2$ |
| $4\text{-}CH(CH_3)_2$ | O | $CH_2$ |
| $4\text{-}OCH_3$ | O | $CH_2$ |
| $4\text{-}NO_2$ | O | $CH_2$ |
| $4\text{-}CO_2CH_2CH_2CH_2CH_3$ | O | $CH_2$ |
| $4\text{-}CO_2CH(CH_3)_2$ | O | $CH_2$ |
| $4\text{-}SCH_3$ | O | $CH_2$ |
| 2-Cl | O | $CH_2$ |
| 2-F | O | $CH_2$ |
| $2\text{-}OCH_2CH_2CH_3$ | O | $CH_2$ |
| $2\text{-}OCH_2CH_2CH_2CH_3$ | O | $CH_2$ |
| H | O | $CH_2$ |
| 2-Br | O | O |
| $2\text{-}CH_3$ | O | O |
| $2\text{-}CHCH_2CH_3$<br>$CH_3$ | O | O |
| $2\text{-}CH_2CH_2CH_3$ | O | O |
| $2\text{-}OCH_3$ | O | O |
| $2\text{-}NO_2$ | O | O |
| $2\text{-}CO_2CH_3$ | O | O |
| $2\text{-}CO_2(CH_2)_5CH_3$ | O | O |
| $2\text{-}CO_2CH_2CH_3$ | O | O |
| 4-Cl | O | O |
| 4-F | O | O |
| 4-Br | O | O |
| $4\text{-}CH_3$ | O | O |
| $4\text{-}C_2H_5$ | O | O |
| $4\text{-}CH(CH_3)_2$ | O | O |
| $4\text{-}OCH_3$ | O | O |
| $4\text{-}NO_2$ | O | O |
| $4\text{-}CO_2CH_2CH_2CH_2CH_3$ | O | O |
| $4\text{-}CO_2CH(CH_3)_2$ | O | O |
| $4\text{-}SCH_3$ | O | O |
| 2-Cl | O | O |
| 2-F | O | O |
| $2\text{-}OCH_2CH_2CH_3$ | O | O |
| $2\text{-}OCH_2CH_2CH_2CH_3$ | O | O |
| H | O | O |
| H | S | O |
| 2-Cl | S | O |
| 2-Br | S | O |
| 2-F | S | O |
| $2\text{-}CH_3$ | S | O |
| $2\text{-}OCH_3$ | S | O |
| $2\text{-}NO_2$ | S | O |
| $2\text{-}CO_2CH_3$ | S | O |
| 4-Cl | S | O |
| 4-F | S | O |
| $4\text{-}C_2H_5$ | S | O |
| $4\text{-}NO_2$ | S | O |

TABLE II-B-continued

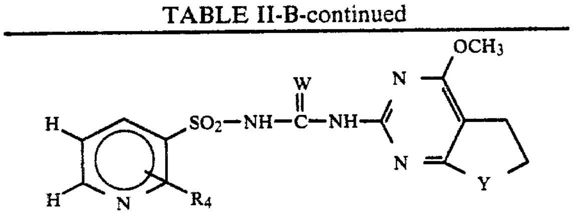

| $R_4$ | W | Y |
|---|---|---|
| 4-$CO_2C_2H_5$ | S | O |

TABLE II-C

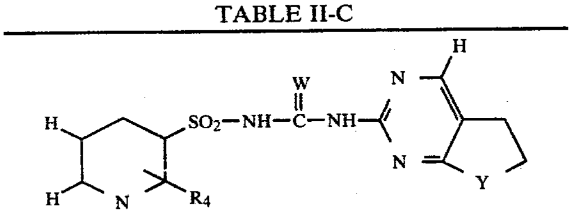

| $R_4$ | W | Y |
|---|---|---|
| 2-Br | O | $CH_2$ |
| 2-$CH_3$ | O | $CH_2$ |
| 2-$CHCH_2CH_3$<br>\|<br>$CH_3$ | O | $CH_2$ |
| 2-$CH_2CH_2CH_3$ | O | $CH_2$ |
| 2-$OCH_3$ | O | $CH_2$ |
| 2-$NO_2$ | O | $CH_2$ |
| 2-$CO_2CH_3$ | O | $CH_2$ |
| 2-$CO_2(CH_2)_5CH_3$ | O | $CH_2$ |
| 2-$CO_2CH_2CH_3$ | O | $CH_2$ |
| 4-Cl | O | $CH_2$ |
| 4-F | O | $CH_2$ |
| 4-Br | O | $CH_2$ |
| 4-$CH_3$ | O | $CH_2$ |
| 4-$C_2H_5$ | O | $CH_2$ |
| 4-$CH(CH_3)_2$ | O | $CH_2$ |
| 4-$OCH_3$ | O | $CH_2$ |
| 4-$NO_2$ | O | $CH_2$ |
| 4-$CO_2CH_2CH_2CH_2CH_3$ | O | $CH_2$ |
| 4-$CO_2CH(CH_3)_2$ | O | $CH_2$ |
| 4-$SCH_3$ | O | $CH_2$ |
| 2-Cl | O | $CH_2$ |
| 2-F | O | $CH_2$ |
| 2-$OCH_2CH_2CH_3$ | O | $CH_2$ |
| 2-$OCH_2CH_2CH_2CH_3$ | O | $CH_2$ |
| H | O | $CH_2$ |
| 2-$S(CH_2)_2CH_3$ | O | $CH_2$ |
| 2-Br | O | O |
| 2-$CH_3$ | O | O |
| 2-$CHCH_2CH_3$<br>\|<br>$CH_3$ | O | O |
| 2-$CH_2CH_2CH_3$ | O | O |
| 2-$OCH_3$ | O | O |
| 2-$NO_2$ | O | O |
| 2-$CO_2CH_3$ | O | O |
| 2-$CO_2(CH_2)_5CH_3$ | O | O |
| 2-$CO_2CH_2CH_3$ | O | O |
| 4-Cl | O | O |
| 4-F | O | O |
| 4-Br | O | O |
| 4-$CH_3$ | O | O |
| 4-$C_2H_5$ | O | O |
| 4-$CH(CH_3)_2$ | O | O |
| 4-$OCH_3$ | O | O |
| 4-$NO_2$ | O | O |
| 4-$CO_2CH_2CH_2CH_2CH_3$ | O | O |
| 4-$CO_2CH(CH_3)_2$ | O | O |
| 4-$SCH_3$ | O | O |
| 2-Cl | O | O |
| 2-F | O | O |

TABLE II-C-continued

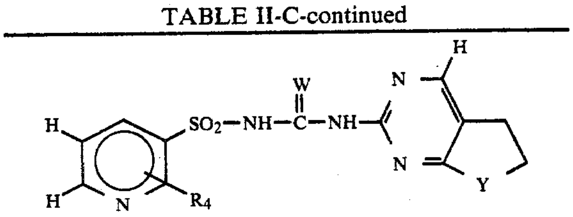

| $R_4$ | W | Y |
|---|---|---|
| 2-$OCH_2CH_2CH_3$ | O | O |
| 2-$OCH_2CH_2CH_2CH_3$ | O | O |
| H | O | O |
| -2-$S(CH_2)_2CH_3$ | O | O |
| 2-Cl | S | O |
| 2-Br | S | O |
| 2-$CH_3$ | S | O |
| 2-$OCH_3$ | S | O |
| 2-$NO_2$ | S | O |
| 2-$CO_2CH(CH_3)_2$ | S | O |
| 2-$SCH_3$ | S | O |
| 4-Cl | S | O |
| 4-F | S | O |
| 4-$CH_3$ | S | O |
| 4-$OCH_3$ | S | O |
| 4-$CO_2CH_3$ | S | O |

TABLE II-D

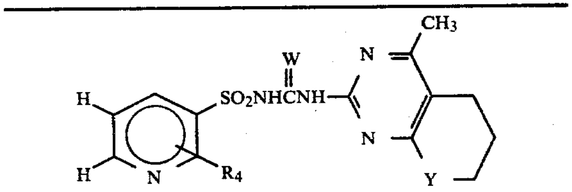

| $R_4$ | W | Y |
|---|---|---|
| 2-Cl | O | $CH_2$ |
| 2-F | O | $CH_2$ |
| 2-Br | O | $CH_2$ |
| 2-$CH_3$ | O | $CH_2$ |
| 2-$CH_2CH_2CH_3$ | O | $CH_2$ |
| 2-$NO_2$ | O | $CH_2$ |
| 2-$CO_2CH_3$ | O | $CH_2$ |
| 2-$CO_2CH_2CH(CH_3)_2$ | O | $CH_2$ |
| 2-$SCH_3$ | O | $CH_2$ |
| 4-Cl | O | $CH_2$ |
| 4-F | O | $CH_2$ |
| 4-$CH_2CH_2CH_3$ | O | $CH_2$ |
| 4-$CH_3$ | O | $CH_2$ |
| 4-$CH_3O$ | O | $CH_2$ |
| 4-$NO_2$ | O | $CH_2$ |
| 4-$CO_2CH(CH_3)_2$ | O | $CH_2$ |
| 4-$SCH_3$ | O | $CH_2$ |
| 2-$S(CH_2)_3CH_3$ | O | $CH_2$ |
| 2-Cl | O | O |
| 2-F | O | O |
| 2-Br | O | O |
| 2-$CH_3$ | O | O |
| 2-$CH_2CH_2CH_3$ | O | O |
| 2-$NO_2$ | O | O |
| 2-$CO_2CH_3$ | O | O |
| 2-$CO_2CH_2CH(CH_3)_2$ | O | O |
| 2-$SCH_3$ | O | O |
| 4-Cl | O | O |
| 4-F | O | O |
| 4-$CH_2CH_2CH_3$ | O | O |
| 4-$CH_3$ | O | O |
| 4-$CH_3O$ | O | O |
| 4-$NO_2$ | O | O |
| 4-$CO_2CH(CH_3)_2$ | O | O |
| 4-$SCH_3$ | O | O |
| 2-$S(CH_2)_3CH_3$ | O | O |
| 2-Cl | S | O |
| 2-F | S | O |
| 2-Br | S | O |
| 2-$C_2H_5$ | S | O |
| 2-$OC_2H_5$ | S | O |

TABLE II-D-continued

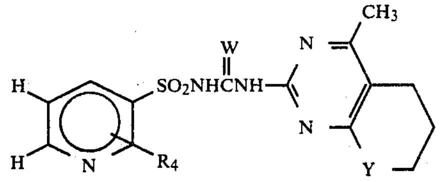

| R4 | W | Y |
|---|---|---|
| $2-NO_2$ | S | O |
| $2-CH_2CH_3$ | S | O |
| $2-SCH(CH_3)_2$ | S | O |
| 4-Cl | S | O |
| 4-F | S | O |
| $4-CH_3$ | S | O |
| $4-OCH_3$ | S | O |
| $4-NO_2$ | S | O |
| $4-CO_2CH_3$ | S | O |

TABLE II-E

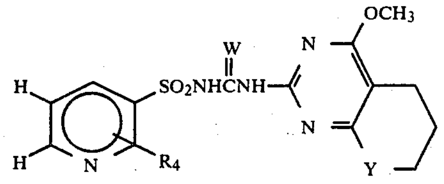

| R4 | W | Y |
|---|---|---|
| 4-Cl | O | $CH_2$ |
| 4-Br | O | $CH_2$ |
| $4-CH_3$ | O | $CH_2$ |
| $4-OCH_3$ | O | $CH_2$ |
| $4-NO_2$ | O | $CH_2$ |
| $4-CO_2CH_3$ | O | $CH_2$ |
| $4-CO_2(CH_2)_4CH_3$ | O | $CH_2$ |
| $4-SCH_3$ | O | $CH_2$ |
| 2-Cl | O | $CH_2$ |
| 2-F | O | $CH_2$ |
| 2-Br | O | $CH_2$ |
| $2-CH(CH_3)_2$ | O | $CH_2$ |
| $2-CH_3O$ | O | $CH_2$ |
| $2-NO_2$ | O | $CH_2$ |
| $2-COOC_2H_5$ | O | $CH_2$ |
| $2-SCH_3$ | O | $CH_2$ |
| $4-SCH_2CH_3$ | O | $CH_2$ |
| 4-Cl | O | O |
| 4-Br | O | O |
| $4-CH_3$ | O | O |
| $4-OCH_3$ | O | O |
| $4-NO_2$ | O | O |
| $4-CO_2CH_3$ | O | O |
| $4-CO_2(CH_2)_4CH_3$ | O | O |
| $4-SCH_3$ | O | O |
| 2-Cl | O | O |
| 2-F | O | O |
| 2-Br | O | O |
| $2-CH(CH_3)_2$ | O | O |
| $2-CH_3O$ | O | O |
| $2-NO_2$ | O | O |
| $2-COOC_2H_5$ | O | O |
| $2-SCH_3$ | O | O |
| $4-SCH_2CH_3$ | O | O |
| 2-Cl | S | O |
| 2-F | S | O |
| 2-Br | S | O |
| $2-C_2H_5$ | S | O |
| $2-OCH(CH_3)_2$ | S | O |
| $2-NO_2$ | S | O |
| $2-CO_2CH_3$ | S | O |
| $2-SCH_3$ | S | O |
| 4-Cl | S | O |
| 4-Br | S | O |
| $4-CH_3$ | S | O |
| $4-OCH_3$ | S | O |
| $4-NO_2$ | S | O |

TABLE II-E-continued

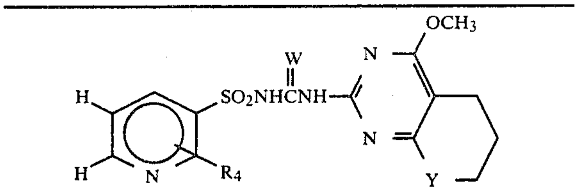

| R4 | W | Y |
|---|---|---|
| $4-CO_2CH_3$ | S | O |

EXAMPLE 8

2-Isopropylaminocarbonyl-N-[(6,7-dihydro-4-methyl-5H-cyclopentapyrimidin-2-yl)aminocarbonyl]benzenesulfonamide To 21.2 ml of 25% trimethylaluminum in hexane (2.36 molar) under nitrogen is added 2.9 g of isopropyl amine in 100 ml of dried methylene chloride. The mixture is stirred at ambient temperature until evolution of methane gas ceases and then 19.5 g of methyl 2[[(6,7-dihydro-4-methyl-5H-cyclopentapyrimidin-2-yl)aminocarbonyl]aminosulfonyl]benzoate and 200 ml of dry toluene is added. The resulting mixture is heated to distill off the methylene chloride and hexane, after which heating is continued at the reflux temperature of toluene. After 2 hours, the toluene is removed in vacuo, and 200 ml of methylene chloride and 100 ml of 10% hydrochloric acid are added. The phases are separated, and the methylene chloride phase is washed once with water, dried over magnesium sulfate, and filtered, and the methylene chloride distilled to yield the desired compound.

By using the procedure of Example 8 with an equivalent amount of an appropriately substituted benzoic acid ester and alkylaminodialkylaluminum, the compounds of Table III can be prepared.

TABLE III-A

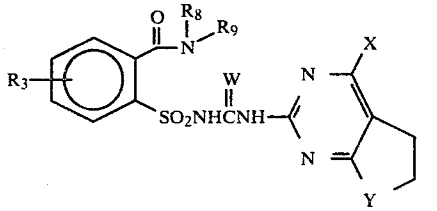

| R3 | R9 | R8 | W | X | Y | m.p. |
|---|---|---|---|---|---|---|
| H | $CH_3$ | H | O | $CH_3$ | $CH_2$ | |
| H | $C_2H_5$ | H | O | $CH_3$ | $CH_2$ | |
| H | $CH(CH_3)_2$ | H | O | $CH_3$ | $CH_2$ | |
| 5-Cl | $CH_3$ | H | O | $CH_3$ | $CH_2$ | |
| 6-Cl | $CH(CH_3)_2$ | H | O | $CH_3$ | $CH_2$ | |
| H | $CH_2CH_2CH_2CH_3$ | H | O | $CH_3$ | $CH_2$ | |
| H | $CH(CH_3)_2$ | H | O | $OCH_3$ | $CH_2$ | |
| 5-Cl | $C_2H_5$ | H | O | $OCH_3$ | $CH_2$ | |
| 6-Cl | $CH_2CH_2CH_3$ | H | O | $OCH_3$ | $CH_2$ | |
| H | $CH(CH_3)_2$ | $CH_3$ | O | $CH_3$ | $CH_2$ | |
| H | $C_2H_5$ | $C_2H_5$ | O | $CH_3$ | $CH_2$ | 166–169° |
| H | $CH(CH_3)_2$ | $CH(CH_3)_2$ | O | $CH_3$ | $CH_2$ | |
| H | $(CH_2)_4H$ | $(CH_2)_4H$ | O | $CH_3$ | $CH_2$ | |
| H | H | H | O | $CH_3$ | $CH_2$ | |
| H | $CH_3$ | H | O | H | $CH_2$ | |
| 5-Cl | $C_2H_5$ | H | O | H | $CH_2$ | |
| 6-Cl | $CH(CH_3)_2$ | H | O | H | $CH_2$ | |
| H | $CH_2CH_2CH_3$ | $CH_3$ | O | H | $CH_2$ | |
| H | $C_2H_5$ | $C_2H_5$ | O | H | $CH_2$ | |
| H | H | H | O | H | $CH_2$ | |

TABLE III-A-continued

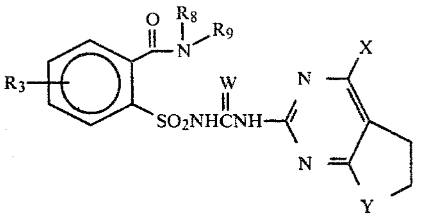

| $R_3$ | $R_9$ | $R_8$ | W | X | Y | m.p. |
|---|---|---|---|---|---|---|
| H | $CH_3$ | $CH_3$ | O | Cl | $CH_2$ | |
| H | $C_2H_5$ | H | O | Cl | $CH_2$ | |
| H | $CH(CH_3)_2$ | H | O | Cl | $CH_2$ | |
| H | $CH_3$ | H | O | Cl | $CH_2$ | |
| 5-Cl | $CH_3$ | $CH_3$ | O | $OC_2H_5$ | $CH_2$ | |
| 6-Cl | $C_2H_5$ | $C_2H_5$ | O | $OC_2H_5$ | $CH_2$ | |
| H | $-CH_2CH_2CH_2CH_2CH_2-$ | | O | $OC_2H_5$ | $CH_2$ | |
| H | $CH_3$ | H | O | $CH_3$ | O | |
| H | $C_2H_5$ | H | O | $CH_3$ | O | |
| H | $CH(CH_3)_2$ | H | O | $CH_3$ | O | |
| 5-Cl | $CH_3$ | H | O | $CH_3$ | O | |
| 6-Cl | $CH(CH_3)_2$ | H | O | $CH_3$ | O | |
| H | $CH_2CH_2CH_2CH_3$ | H | O | $CH_3$ | O | |
| H | $CH(CH_3)_2$ | H | O | $OCH_3$ | O | |
| 5-Cl | $C_2H_5$ | H | O | $OCH_3$ | O | |
| 6-Cl | $CH_2CH_2CH_3$ | H | O | $OCH_3$ | O | |
| H | $CH(CH_3)_2$ | $CH_3$ | O | $CH_3$ | O | |
| H | $C_2H_5$ | $C_2H_5$ | O | $CH_3$ | O | |
| H | $CH(CH_3)_2$ | $CH(CH_3)_2$ | O | $CH_3$ | O | |
| H | $(CH_2)_4H$ | $(CH_2)_4H$ | O | $CH_3$ | O | |
| H | H | H | O | $CH_3$ | O | |
| H | $CH_3$ | H | O | H | O | |
| 5-Cl | $CH_3$ | H | O | H | O | |
| 6-Cl | $C_2H_5$ | H | O | H | O | |
| H | $CH_2CH_2CH_3$ | $CH_3$ | O | H | O | |
| H | $CH(CH_3)_2$ | $C_2H_5$ | O | H | O | |
| H | $(CH_2)_4H$ | $CH_3$ | O | H | O | |
| H | H | H | O | H | O | |
| H | $CH_3$ | $CH_3$ | O | Cl | O | |
| H | $C_2H_5$ | H | O | Cl | O | |
| H | $CH(CH_3)_2$ | H | O | Cl | O | |
| H | $CH_3$ | H | O | Cl | O | |
| 5-Cl | $CH_3$ | $CH_3$ | O | $OC_2H_5$ | O | |
| 6-Cl | $C_2H_5$ | $C_2H_5$ | O | $OC_2H_5$ | O | |
| H | $-CH_2CH_2CH_2CH_2CH_2-$ | | O | $OC_2H_5$ | O | |
| H | H | H | S | $CH_3$ | O | |
| H | $CH_3$ | H | S | $CH_3$ | O | |
| H | $CH(CH_3)_2$ | H | S | $CH_3$ | O | |
| H | $CHC_2H_5$<br>$CH_3$ | H | S | $CH_3$ | O | |
| H | $CH_3$ | $CH_3$ | S | $CH_3$ | O | |
| H | $CH(CH_3)_2$ | $CH(CH_3)_2$ | S | $CH_3$ | O | |
| 5-Cl | $C_2H_5$ | H | S | $CH_3$ | O | |
| 6-Cl | $CH_3$ | $CH_3$ | S | $CH_3$ | O | |
| H | H | H | S | $OCH_3$ | O | |
| H | $CH_3$ | H | S | $OCH_3$ | O | |
| H | $CH_3$ | $CH_3$ | S | $OCH_3$ | O | |
| 5-Cl | $CH_3$ | $CH_3$ | S | $OCH_3$ | O | |
| H | $CH_3$ | H | S | H | O | |
| H | $CH_3$ | $C_2H_5$ | S | H | O | |
| H | $CH(CH_3)_2$ | $CH(CH_3)_2$ | S | H | O | |
| H | $CH_3$ | H | S | Cl | O | |
| H | $CH_3$ | $CH_3$ | S | Cl | O | |
| 6-Cl | $CH_2CH_2CH_3$ | H | S | Cl | O | |
| H | $-CH_2CH_2CH_2CH_2-$ | | S | Cl | O | |
| H | H | H | S | $OC_2H_5$ | O | |
| H | $CH_3$ | $CH_3$ | S | $OC_2H_5$ | O | |
| 5-Cl | $CH_3$ | H | S | $OC_2H_5$ | O | |
| H | $-CH_2CH_2O-CH_2CH_2-$ | | S | $OC_2H_5$ | O | |
| H | H | H | S | $CH_3$ | O | |
| H | $CH_3$ | H | S | $CH_3$ | O | |
| H | $C_2H_5$ | H | S | $CH_3$ | O | |
| H | $CH_3$ | $CH_3$ | S | $CH_3$ | O | |
| H | $CH_3$ | $C_2H_5$ | S | $CH_3$ | O | |
| 6-Cl | $-CH(CH_3)_2$ | H | S | $CH_3$ | O | |
| 5-Cl | $CH_3$ | $CH_3$ | S | $CH_3$ | O | |
| H | H | H | S | $OCH_3$ | O | |

TABLE III-A-continued

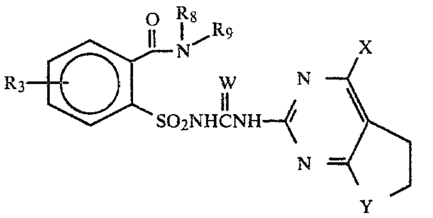

| $R_3$ | $R_9$ | $R_8$ | W | X | Y | m.p. |
|---|---|---|---|---|---|---|
| H | $CH_3$ | H | S | $OCH_3$ | O | |
| H | $C_2H_5$ | $C_2H_5$ | S | $OCH_3$ | O | |
| 5-Cl | $CH_3$ | $-CH(CH_3)_2$ | S | $OCH_3$ | O | |
| H | $CH_3$ | H | S | H | O | |
| H | $-(CH_2)_3CH_3$ | H | S | H | O | |
| H | $CH_3$ | $CH_3$ | S | H | O | |
| H | $C_2H_5$ | H | S | Cl | O | |
| H | $C_2H_5$ | $CH_3$ | S | Cl | O | |
| H | $-CH_2CH_2CH_2CH_2CH_2CH_2-$ | | S | Cl | O | |
| 5-Cl | $CHCH_2CH_3$<br>$CH_3$ | H | S | Cl | O | |
| H | H | H | S | $OC_2H_5$ | O | |
| H | $CH_3$ | $CH_3$ | S | $OC_2H_5$ | O | |
| H | $-CH_2CH_2OCH_2CH_2-$ | | S | $OC_2H_5$ | O | |
| H | $-CH(CH_3)_2$ | $CH_3$ | S | $OC_2H_5$ | O | |
| 6-Cl | $C_2H_5$ | $C_2H_5$ | S | $OC_2H_5$ | O | |

TABLE III-B

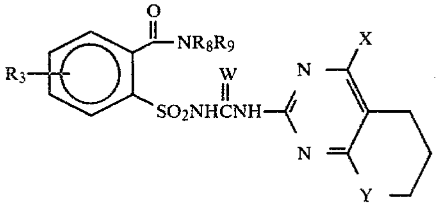

| $R_3$ | $R_9$ | $R_8$ | W | X | Y |
|---|---|---|---|---|---|
| H | $C_2H_5$ | H | O | $CH_3$ | $CH_2$ |
| H | $CH(CH_3)_2$ | H | O | $CH_3$ | $CH_2$ |
| H | $CH_2CH_2CH_3$ | H | O | $CH_3$ | $CH_2$ |
| 5-Cl | $CH_3$<br>$CH$<br>$C_2H_5$ | H | O | $CH_3$ | $CH_2$ |
| H | $CH_3$ | $CH_3$ | O | $CH_3$ | $CH_2$ |
| H | $C_2H_5$ | $CH_3$ | O | $CH_3$ | $CH_2$ |
| H | $C_2H_5$ | $C_2H_5$ | O | $CH_3$ | $CH_2$ |
| H | H | H | O | $CH_3$ | $CH_2$ |
| H | $C_2H_5$ | H | O | $CH_3$ | O |
| H | $CH(CH_3)_2$ | H | O | $CH_3$ | O |
| H | $CH_2CH_2CH_3$ | H | O | $CH_3$ | O |
| 5-Cl | $CH_3$<br>$CH$<br>$C_2H_5$ | H | O | $CH_3$ | O |
| H | $CH_3$ | $CH_3$ | O | $CH_3$ | O |
| H | $C_2H_5$ | $CH_3$ | O | $CH_3$ | O |
| H | $C_2H_5$ | $C_2H_5$ | O | $CH_3$ | O |
| H | H | H | O | $CH_3$ | O |
| H | $C_2H_5$ | $CH_3$ | O | $OCH_3$ | $CH_2$ |
| H | $CH(CH_3)_2$ | H | O | $OCH_3$ | $CH_2$ |
| H | $CH_3$ | $CH_3$ | O | $OCH_3$ | O |
| H | $C_2H_5$ | $C_2H_5$ | O | $OCH_3$ | O |
| H | $CH_3$ | H | S | $CH_3$ | O |
| H | $-CH_2CH_2CH_3$ | H | S | $CH_3$ | O |
| H | $-CH_2CH_2CH_2CH_2-$ | | S | $CH_3$ | O |
| 5-Cl | $CH_3$ | $CH_3$ | S | $CH_3$ | O |
| H | $C_2H_5$ | $CH_3$ | S | $CH_3$ | O |
| H | $C_2H_5$ | H | S | $OCH_3$ | O |

TABLE III-B-continued

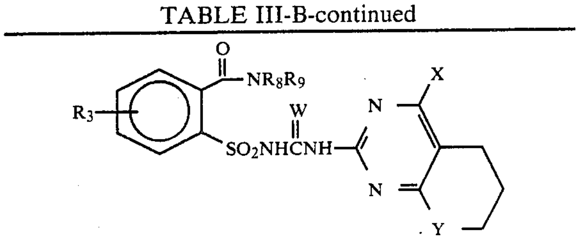

| R3 | R9 | R8 | W | X | Y |
|---|---|---|---|---|---|
| H | $CH_2(CH_3)_3$ | H | S | $OCH_3$ | O |
| H | $CH_3$ | $CH_3$ | S | $OCH_3$ | O |
| H | $CH_3$ | $CH_2CH_2CH_3$ | S | $OCH_3$ | O |
| 6-Cl | $-CH_2CH_2CH_2CH_2CH_2-$ | | S | $OCH_3$ | O |

By using the procedures described above and the appropriate reactants and 4-chloro or 4-ethoxy-5,6-dihydrofuro[2,3-d]pyrimidin-2-amine or 4-chloro or 4-ethoxy-6,7-dihydro-5H-cyclopentapyrimidin-2-amine, the compounds of Table IV-A can be prepared.

Similarly, compounds of Table IV-B can be prepared using the appropriate reactants and starting from 6,7-dihydro-5H-pyrano[2,3-d]pyrimidin-2-amine substituted in the 4-position with hydrogen, chlorine or ethoxy.

TABLE IV-A

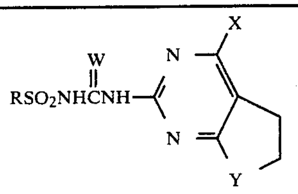

R = 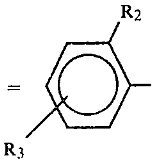 or 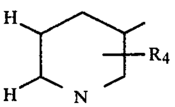

| R2 | R3 | R4 | W | X | Y | m.p. |
|---|---|---|---|---|---|---|
| H | H | — | O | Cl | O | |
| $CO_2CH_3$ | H | — | O | Cl | O | 215-219° |
| $CO_2CH_3$ | 5-Cl | — | O | Cl | $CH_2$ | |
| $SO_2N(CH_3)_2$ | H | — | O | $OC_2H_5$ | $CH_2$ | |
| Cl | H | — | O | $OC_2H_5$ | O | |
| $NO_2$ | H | — | O | $OC_2H_5$ | $CH_2$ | |
| $SO_2CH_3$ | H | — | O | $OC_2H_5$ | $CH_2$ | |
| $CO_2CH_2CH{=}CH_2$ | H | — | O | $OC_2H_5$ | O | |
| $CON(CH_3)_2$ | H | — | O | $OC_2H_5$ | $CH_2$ | |
| 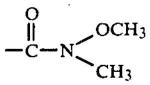 | H | — | O | $OC_2H_5$ | O | |
| F | H | — | O | $OC_2H_5$ | O | |
| — | — | 2-$CO_2CH_3$ | O | Cl | O | |
| — | — | 4-$CO_2CH_2CH_3$ | O | Cl | $CH_2$ | |
| — | — | 4-$NO_2$ | O | Cl | O | |
| — | — | 2-$CH_3O$ | O | Cl | O | |
| — | — | 2-Br | O | $OC_2H_5$ | $CH_2$ | |
| — | — | 2-$CH_3$ | O | $OC_2H_5$ | $CH_2$ | |
| — | — | 2-$CO_2CH(CH_3)_2$ | O | $OC_2H_5$ | O | |
| — | — | 4-F | O | $OC_2H_5$ | $CH_2$ | |
| — | — | 2-$NO_2$ | O | $OC_2H_5$ | $CH_2$ | |
| Cl | H | — | S | Cl | O | |
| $NO_2$ | H | — | S | Cl | O | |
| $CO_2CH_3$ | H | — | S | Cl | O | |
| $SO_2N(CH_3)_2$ | H | — | S | Cl | O | |
| Cl | 5-Cl | — | S | Cl | O | |
| Cl | H | — | S | $OC_2H_5$ | O | |
| $NO_2$ | H | — | S | $OC_2H_5$ | O | |
| $CO_2C_2H_5$ | H | — | S | $OC_2H_5$ | O | |
| 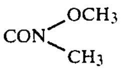 | H | — | S | $OC_2H_5$ | O | |
| $OCH_3$ | 5-$OCH_3$ | — | S | $OC_2H_5$ | O | |
| $SCH_3$ | H | — | S | $OC_2H_5$ | O | |
| $SO_2C_2H_5$ | H | — | S | $OC_2H_5$ | O | |
| — | — | 2-Cl | S | Cl | O | |

TABLE IV-A-continued

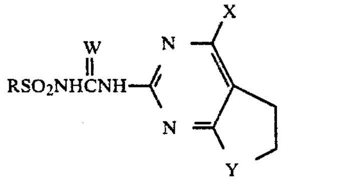

R = 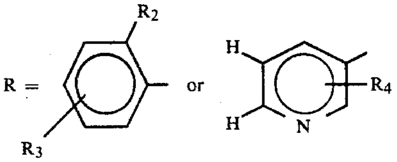

| $R_2$ | $R_3$ | $R_4$ | W | X | Y | m.p. |
|---|---|---|---|---|---|---|
| — | — | 4-F | S | Cl | O | |
| — | — | 2-$NO_2$ | S | Cl | O | |
| — | — | 4-$CO_2CH_3$ | S | Cl | O | |
| — | — | 2-$OCH_3$ | S | Cl | O | |
| — | — | 2-$CH_3$ | S | Cl | O | |
| — | — | 2-Cl | S | $OC_2H_5$ | O | |
| — | — | 2-$NO_2$ | S | $OC_2H_5$ | O | |
| — | — | 4-$CO_2C_2H_5$ | S | $OC_2H_5$ | O | |
| — | — | 4-$SCH_3$ | S | $OC_2H_5$ | O | |
| — | — | 2-$OCH_3$ | S | $OC_2H_5$ | O | |
| — | — | 4-$CH_3$ | S | $OC_2H_5$ | O | |

TABLE IV-B

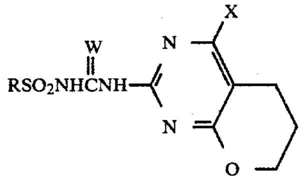

R = 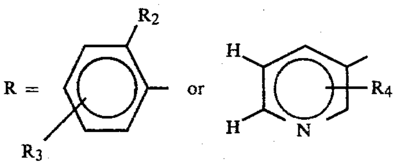

| $R_2$ | $R_3$ | $R_4$ | W | X | m.p. |
|---|---|---|---|---|---|
| H | H | — | O | Cl | |
| $CO_2CH_3$ | H | — | O | Cl | 215–220° |
| $CO_2CH_3$ | 5-Cl | — | O | Cl | |
| $SO_2N(CH_3)_2$ | H | — | O | $OC_2H_5$ | |
| Cl | H | — | O | $OC_2H_5$ | |
| $NO_2$ | H | — | O | $OC_2H_5$ | |
| $SO_2CH_3$ | H | — | O | $OC_2H_5$ | |
| $CO_2CH_2CH=CH_2$ | H | — | O | $OC_2H_5$ | |
| $CON(CH_3)_2$ | H | — | O | $OC_2H_5$ | |
| 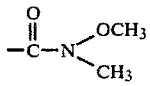 | H | — | O | $OC_2H_5$ | |
| F | H | — | O | $OC_2H_5$ | |
| — | — | 2-$CO_2CH_3$ | O | Cl | |
| — | — | 4-$CO_2CH_2CH_3$ | O | Cl | |
| — | — | 4-$NO_2$ | O | Cl | |
| — | — | 2-$CH_3O$ | O | Cl | |
| — | — | 2-Br | O | $OC_2H_5$ | |
| — | — | 2-$CH_3$ | O | $OC_2H_5$ | |
| — | — | 2-$CO_2CH(CH_3)_2$ | O | $OC_2H_5$ | |
| — | — | 4-F | O | $OC_2H_5$ | |
| — | — | 2-$NO_2$ | O | $OC_2H_5$ | |
| Cl | H | — | S | Cl | |
| $NO_2$ | H | — | S | Cl | |
| $CO_2CH_3$ | H | — | S | Cl | |

TABLE IV-B-continued

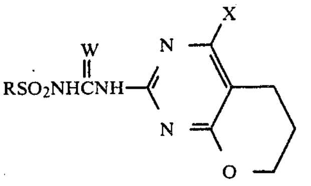

R = 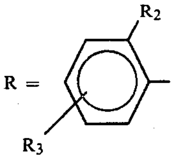 or 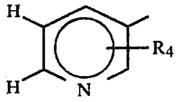

| $R_2$ | $R_3$ | $R_4$ | W | X | m.p. |
|---|---|---|---|---|---|
| $SO_2N(CH_3)_2$ | H | — | S | Cl | |
| Cl | 5-Cl | — | S | Cl | |
| Cl | H | — | S | $OC_2H_5$ | |
| $NO_2$ | H | — | S | $OC_2H_5$ | |
| $CO_2C_2H_5$ | H | — | S | $OC_2H_5$ | |
| 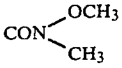 | H | — | S | $OC_2H_5$ | |
| $OCH_3$ | 5-$OCH_3$ | — | S | $OC_2H_5$ | |
| $SCH_3$ | H | — | S | $OC_2H_5$ | |
| $SO_2C_2H_5$ | H | — | S | $OC_2H_5$ | |
| Cl | H | — | S | Cl | |
| $NO_2$ | H | — | S | Cl | |
| $CO_2CH_3$ | H | — | S | Cl | |
| Cl | 5-Cl | — | S | Cl | |
| $SO_2N(C_2H_5)_2$ | H | — | S | Cl | |
| Cl | H | — | S | $OC_2H_5$ | |
| $NO_2$ | H | — | S | $OC_2H_5$ | |
| $CO_2CH_3$ | H | — | S | $OC_2H_5$ | |
| $SCH_3$ | 5-$SCH_3$ | — | S | $OC_2H_5$ | |
| $CON(CH_3)_2$ | H | — | S | $OC_2H_5$ | |
| $SO_2N(CH_3)_2$ | H | — | S | $OC_2H_5$ | |
| — | — | 2-Cl | S | Cl | |
| — | — | 4-F | S | Cl | |
| — | — | 2-$NO_2$ | S | Cl | |
| — | — | 4-$CO_2CH_3$ | S | Cl | |
| — | — | 2-$OCH_3$ | S | Cl | |
| — | — | 2-$CH_3$ | S | Cl | |
| — | — | 4-Cl | S | Cl | |
| — | — | 4-$NO_2$ | S | Cl | |
| — | — | 4-$CO_2CH_3$ | S | Cl | |
| — | — | 4-$CO_2CH(CH_3)_2$ | S | Cl | |
| — | — | 2-Cl | S | $OC_2H_5$ | |
| — | — | 2-$NO_2$ | S | $OC_2H_5$ | |
| — | — | 4-$CO_2C_2H_5$ | S | $OC_2H_5$ | |
| — | — | 4-$SCH_3$ | S | $OC_2H_5$ | |
| — | — | 2-$OCH_3$ | S | $OC_2H_5$ | |
| — | — | 4-$CH_3$ | S | $OC_2H_5$ | |
| — | — | 4-F | S | $OC_2H_5$ | |
| — | — | 2-Br | 2 | $OC_2H_5$ | |
| — | — | 2-$NO_2$ | S | $OC_2H_5$ | |
| — | — | 4-$CO_2CH_3$ | S | $OC_2H_5$ | |
| — | — | 2-$C_2H_5$ | S | $OC_2H_5$ | |
| H | H | — | O | H | |
| $CO_2CH_3$ | H | — | O | H | |
| $CO_2CH_3$ | 5-Cl | — | O | H | |
| $SO_2N(CH_3)_2$ | H | — | O | H | |
| Cl | H | — | O | H | |
| $NO_2$ | H | — | O | H | |
| $SO_2CH_3$ | H | — | O | H | |
| $CO_2CH_2CH{=}CH_2$ | H | — | O | H | |
| $CON(CH_3)_2$ | H | — | O | H | |
| 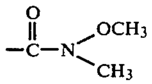 | H | — | O | H | |
| F | H | — | O | H | |
| — | — | 2-$CO_2CH_3$ | O | H | |
| — | — | 4-$CO_2CH_2CH_3$ | O | H | |
| — | — | 4-$NO_2$ | O | H | |

TABLE IV-B-continued

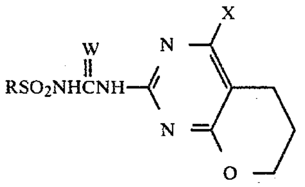

R = 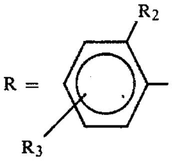 or 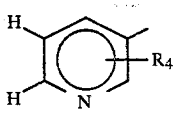

| $R_2$ | $R_3$ | $R_4$ | W | X | m.p. |
|---|---|---|---|---|---|
| — | — | 2-$CH_3O$ | O | H | |
| — | — | 2-Br | O | H | |
| — | — | 2-$CH_3$ | O | H | |
| — | — | 2-$CO_2CH(CH_3)_2$ | O | H | |
| — | — | 4-F | O | H | |
| — | — | 2-$NO_2$ | O | H | |
| H | H | — | S | H | |
| $CO_2CH_3$ | H | — | S | H | |
| $CO_2CH_3$ | 5-Cl | — | S | H | |
| $SO_2N(CH_3)_2$ | H | — | S | H | |
| Cl | H | — | S | H | |
| $NO_2$ | H | — | S | H | |
| $SO_2CH_3$ | H | — | S | H | |
| $CO_2CH_2CH{=}CH_2$ | H | — | S | H | |
| $CON(CH_3)_2$ | H | — | S | H | |
| 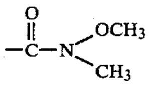 | H | — | S | H | |
| F | H | — | S | H | |
| — | — | 2-$CO_2CH_3$ | S | H | |
| — | — | 4-$CO_2CH_2CH_3$ | S | H | |
| — | — | 4-$NO_2$ | S | H | |
| — | — | 2-$CH_3O$ | S | H | |
| — | — | 2-Br | S | H | |
| — | — | 2-$CH_3$ | S | H | |
| — | — | 2-$CO_2CH(CH_3)_2$ | S | H | |
| — | — | 4-F | S | H | |
| — | — | 2-$NO_2$ | S | H | |

Compounds of Formula II are prepared according to the procedures of Equations 2 and 5 and Example 9 wherein temperatures are given in degrees centrigrade.

EXAMPLE 9

Methyl N'-(2-chlorophenylsulfonyl)-N-(5,6-dihydro-4-methylfuro[2,3-d]pyrimidin-2-yl)carbamimidothioate To a suspension of 3.85 g 2-chloro-N-[(5,6-dihydro-2-methylfuro[2,3-d]pyrimidine-2-yl)aminothioxomethyl]-benzenesulfonamide in 150 ml of anhydrous tetrahydrofuran was added 4.3 ml of 3 M $NaOCH_3/CH_3OH$ solution. The reaction reaction mixture was refluxed for 1.25 hour, whereupon 1.85 g of methyl iodide in 10 ml of anhydrous tetrahydrofuran was added. After refluxing and stirring for an additional 12 hours, the reaction mixture was cooled, solvent was removed under vacuum and the residue was recrystallized from acetonitrile to yield 1 g of the product.

TABLE V-a

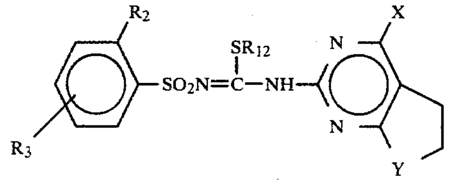

| $R_{12}$ | $R_2$ | $R_3$ | X | Y | m.p. |
|---|---|---|---|---|---|
| $CH_3$ | Cl | 5-Cl | $CH_3O$ | O | |
| $CH_3CH_2$ | Cl | 5-Cl | $CH_3$ | O | |
| $CH_3$ | Cl | 5-Cl | $CH_3CH_2O$ | O | |
| $CH_3$ | $CH_3$ | 5-$CH_3$ | H | O | |
| $CH_3$ | $CH_3$ | 5-$CH_3$ | $CH_3$ | O | |

TABLE V-a-continued

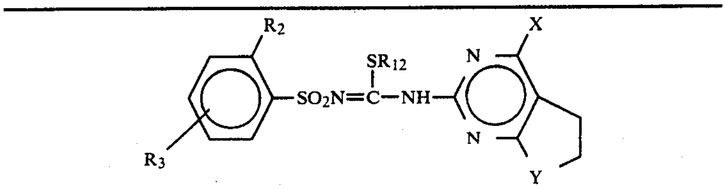

| $R_{12}$ | $R_2$ | $R_3$ | X | Y | m.p. |
|---|---|---|---|---|---|
| $CH_3$ | $CH_3$ | H | $CH_3O$ | O | |
| $CH_3$ | $CH_3$ | H | $CH_3$ | O | |
| $CH_3(CH_2)_3$ | H | H | $CH_3O$ | O | |
| $CH_3$ | H | H | $CH_3$ | O | |
| $CH_3CH_2$ | Cl | H | H | O | |
| $CH_3$ | F | H | $CH_3$ | O | |
| $CH_3$ | $CH_3O$ | 5-Cl | $CH_3$ | O | |
| $CH_3$ | Cl | 6-Cl | $CH_3$ | O | |
| $CH_3$ | Cl | 5-$CH_3$ | H | O | |
| $CH_3$ | F | H | $CH_3O$ | O | |
| $CH_3$ | $CH_3O$ | 5-Cl | $CH_3O$ | O | |
| $CH_3$ | $NO_2$ | H | $CH_3$ | O | |
| $CH_3$ | $NO_2$ | H | $CH_3O$ | O | |
| $CH_3$ | $SO_2N(CH_3)_2$ | H | $CH_3$ | O | |
| $CH_3$ | $CH_3SO-$ | H | $CH_3$ | O | |
| $CH_3$ | Cl | 3-Cl | H | O | |
| $(CH_3)_2CHCH_2$ | $CH_3O$ | 5-$CH_3O$ | $CH_3$ | O | |
| $CH_3$ | $CF_3$ | H | $CH_3$ | O | |
| $CH_3$ | $CH_3O$ | H | Cl | O | |
| $CH_3$ | H | 3-Cl | $CH_3$ | O | |
| $CH_3$ | H | 3-F | $CH_3$ | O | |
| $CH_3$ | Cl | H | $CH_3$ | O | 161-162° |
| $CH_3$ | H | 3-$CH_3$ | $CH_3$ | O | |
| $(CH_3)_2CH$ | H | 3-Br | $CH_3O$ | O | |
| $CH_3$ | $SO_2N(OCH_3)CH_3$ | H | $CH_3$ | O | |
| $CH_3$ | F | 6-F | H | O | |
| $CH_3$ | F | 5-F | $CH_3$ | O | |
| $CH_3$ | $SO_2OCH_2CF_3$ | H | $CH_3$ | O | |
| $CH_3$ | $SO_2OCH_2CCl_3$ | H | H | O | |
| $CH_3$ | Cl | 5-$CH_3$ | $CH_3$ | O | |
| $CH_3(CH_2)_3$ | Cl | H | Cl | O | |
| $CH_3CH_2$ | $CH_3O$ | 5-$CH_3O$ | $CH_3O$ | O | |
| $CH_3(CH_2)_3\underset{CH_3}{\underset{\vert}{CH}}$ | $CH_3O$ | 5-$CH_3O$ | H | O | |
| $CH_3(CH_2)_3$ | $CH_3$ | H | $CH_3O$ | O | |
| $(CH_3)_2CH$ | $CH_3$ | H | $CH_3$ | O | |
| $CH_3(CH_2)_4$ | H | H | $CH_3$ | O | |
| $CH_3$ | Cl | H | $CH_3O$ | O | |
| n-$C_7H_{15}$ | Cl | H | $CH_3$ | O | 110-111.5° |
| n-$C_{10}H_{21}$ | Cl | H | Cl | O | |
| $\underset{CH_3}{\underset{\vert}{CH}}(CH_2)_7CH_3$ | Cl | H | $CH_3$ | O | |
| $CH_3$ | $\overset{O}{\overset{\Vert}{C}}SCH_3$ | H | $CH_3$ | O | |
| $CH_2CN$ | $\overset{O}{\overset{\Vert}{C}}SC_2H_5$ | H | $CH_3O$ | O | |
| $\underset{CH_3}{\underset{\vert}{CH}}CO_2CH_3$ | Cl | H | $CH_3$ | O | 241-243° |
| $\underset{CH_3}{\underset{\vert}{CH}}-CO_2CH(CH_3)_2$ | F | H | $CH_3$ | O | |
| $-CH_2CN$ | Cl | H | $CH_3$ | O | |
| $-CH_2COOH$ | Cl | H | $CH_3$ | O | |
| $-\underset{CH_3}{\underset{\vert}{CH}}COOH$ | Cl | H | $CH_3$ | O | 115-188°(d) |

TABLE V-a-continued

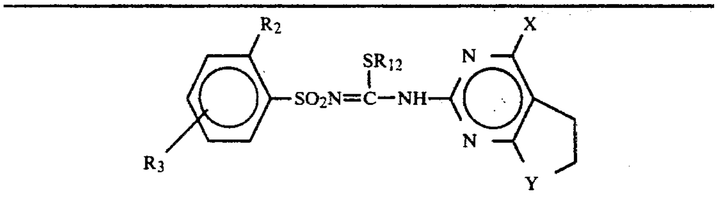

| $R_{12}$ | $R_2$ | $R_3$ | X | Y | m.p. |
|---|---|---|---|---|---|
| $CH_2-C_6H_5$ | Cl | H | $CH_3$ | O | 140-142° |
| $CH-C_6H_5$<br>$CH_3$ | Cl | H | $CH_3$ | O | |
| 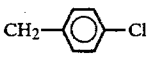 | Cl | H | H | O | |
| 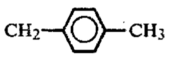 | Cl | H | $CH_3$ | O | |
| $CH_2CN$ | $CO_2CH_3$ | H | $CH_3$ | O | |
| $-CH_2CH=CH_2$ | $CO_2CH_3$ | H | $CH_3$ | O | |
| $-CH_2CH=CH_2$ | Cl | H | Cl | O | |
| $CH_2CH=CH-CH_3$ | Cl | H | $CH_3O$ | O | |
| $CH_2C\equiv CH$ | $CO_2CH(CH_3)_2$ | H | H | O | |
| $CH_2CONH_2$ | Cl | H | $CH_3$ | O | 150-152° |
| $-(CH_2)_5CH_3$ | Cl | H | $CH_3O$ | O | |
| $-(CH_2)_7CH_3$ | Cl | H | $CH_3O$ | O | |
| n-$C_{12}H_{25}$ | Cl | H | $CH_3$ | O | 83-85° |
| $-CHCOOH$<br>$CH_3$ | $CH_3O$ | 5-$CH_3O$ | $CH_3O$ | O | |
| $-CH_3$ | $CH_3O$ | 5-$CH_3O$ | $CH_3O$ | O | |
| $-CH_2CN$ | F | H | H | O | |
| 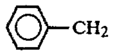 | $NO_2-$ | H | $CH_3$ | O | |
| 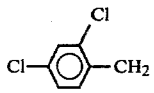 | Br | 5-Br | $CH_3$ | O | |
| $-CH_2COOH$<br>$CH_3$ | $CON(CH_3)_2$ | H | $CH_3O$ | O | |
| 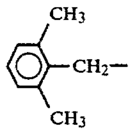 | $CH_3(CH_2)_5SO_2$ | H | $CH_3CH_2O$ | O | |
| 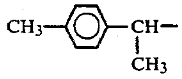 | 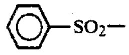 | 5-$CH_3$ | Cl | O | |
| 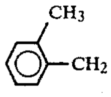 | $CH_3$ | 5-$CH_3$ | $CH_3$ | O | |
| $-CHC\equiv N$<br>$CH_3$ | $(CH_3)_2CH_2SO_2$ | H | H | O | |
| $-CH_3$ | $SO_2N(C_2H_5)_2$ | H | $CH_3$ | O | |

TABLE V-a-continued

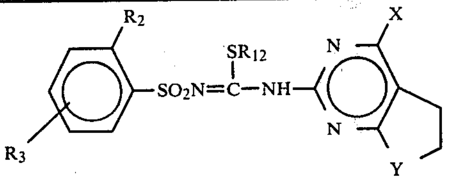

| $R_{12}$ | $R_2$ | $R_3$ | X | Y | m.p. |
|---|---|---|---|---|---|
| $-C_2H_5$ | 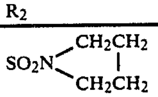 | H | $CH_3$ | O | |
| $-CH_3$ | $SO_2OCH_2CF_3$ | H | $CH_3$ | O | |
| $-CH(CH_3)_2$ | $SO_2OCH_2CCl_3$ | H | $CH_3O$ | O | |

TABLE V-b

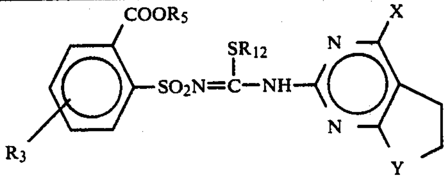

| $R_{12}$ | $R_3$ | $R_5$ | X | Y |
|---|---|---|---|---|
| $CH_3$ | H | $CH_3$ | $CH_3$ | O |
| $CH_3$ | H | $CH_3$ | $CH_3O$ | O |
| $CH_3CH_2$ | 5-Cl | $CH_3$ | $CH_3O$ | O |
| $(CH_3)_2CH$ | 5-Br | $CH_3$ | $CH_3$ | O |
| $CH_3CH_2$ | 5-Cl | $CH_3$ | $CH_3$ | O |
| $CH_3(CH_2)_3$ | 5-$CH_3O$ | $CH_3$ | $CH_3$ | O |
| $(CH_3)_2CHCH_2$ | 5-$CH_3O$ | $CH_3$ | $CH_3$ | O |
| $CH_3$ | 5-$CH_3O$ | $CH_3$ | $CH_3$ | O |
| $CH_3$ | H | $CH_3CH_2\overset{CH_3}{\overset{\vert}{CH}}$ | H | O |
| $CH_3CH_2(CH_3)CH$ | H | $CH_3(CH_2)_3$ | $CH_3$ | O |
| $CH_3$ | 5-$CH_3O$ | $CH_3$ | $CH_3O$ | O |
| $CH_3$ | 3-$CH_3$ | $CH_3CH_2$ | $CH_3$ | O |
| $C_2H_5$ | H | $CH_3$ | $CH_3O$ | O |
| $-\underset{CH_3}{\underset{\vert}{CH}}COOCH_3$ | H | $CH_3$ | $CH_3O$ | O |
| $CH_3$ | H | $CH_2CH{=}CH_2$ | $CH_3O$ | O |
| $CH_3$ | H | $CH(CH_3)CH{=}CH_2$ | $CH_3$ | O |
| $-CH_2CH{=}CH_2$ | H | $CH_3OCH_2CH_2$ | $CH_3$ | O |
| $-\underset{CH_3}{\underset{\vert}{CH}}C{\equiv}N$ | H | 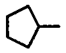 | H | O |
| $-CH_2C{\equiv}CH$ | 5-Cl | $CH_3CH_2OCH_2CH_2$ | $CH_3O$ | O |
| n-$C_{11}H_{23}$ | 5-F | $CH_3(CH_2)_2\underset{CH_3}{\underset{\vert}{CH}}-$ | H | O |
| $-CH_2COOC_2H_5$ | 6-Cl | $CH_3CH{=}CH-CH_2$ | $CH_3O$ | O |
| $CH_3OCH_2CH_2$ | 5-Br | $(CH_3)_2CH-$ | $CH_3O$ | O |
| $-\underset{CH_3}{\underset{\vert}{CH}}CO_2CH(CH_3)_2$ | H | $CH_3$ | $CH_3$ | O |
| 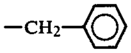 | H | $CH_3OCH_2CH_2$ | H | O |
| $CH_2COOCH_3$ | H | n-$C_6H_{13}-$ | $CH_3$ | O |
| $-CH_2CH_2CH_2OCH_3$ | H | $CH_2{=}CH-CH_2-$ | H | O |

TABLE V-b-continued

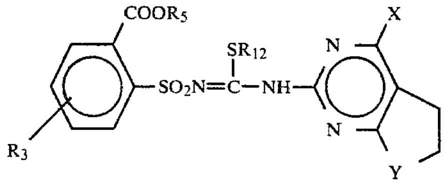

| $R_{12}$ | $R_3$ | $R_5$ | X | Y |
|---|---|---|---|---|
| $-CH(CH_3)_2$ | H | $-CHC{=}CH$<br>$\ \ \ \ \vert\ \ \ \ \ \vert$<br>$\ \ \ \ Cl\ \ Cl$ | Cl | O |
| $-CH_2C{\equiv}CH$ | 5-Cl | 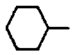 | Cl | O |
| $CH_2COOCH_3$<br>$\vert$<br>$CH_3$ | H | $CH_3$ | $CH_3O$ | O |
| $-CH_2CO_2CHCH_2CH_3$<br>$\vert$<br>$CH_3$ | 3-F | $CH_3CH_2$ | $CH_3$ | O |
| $-CH_2C{\equiv}CH$ | 6-$CH_3$ | $CH_3(CH_2)_2-$ | H | O |
| $-CH_2CH_2CH_3$ | 6-Cl | $-CH_2CCl_3$ | Cl | O |
| $-CHCN$<br>$\vert$<br>$CH_3$ | H | $-(CH_2)_3CH_3$ | Cl | O |
| $-(CH_2)_5CH_3$ | H | $-CH_2CH{=}CH_2$ | H | O |
| $-CH_2COOH$ | 5-Br | $C_2H_5$ | H | O |

TABLE V-c

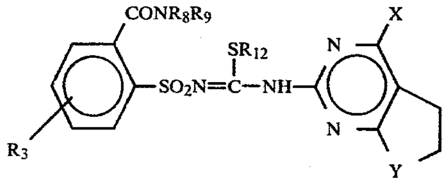

| $R_{12}$ | $R_3$ | $R_8$ | $R_9$ | X | Y |
|---|---|---|---|---|---|
| $CH_3(CH_2)_5$ | H | $CH_3$ | $CH_3$ | $CH_3O$ | O |
| $CH_3$ | 5-Cl | $CH_3CH_2$ | $CH_3CH_2$ | $CH_3O$ | O |
| $CH_3(CH_2)_3$ | 6-Cl | $CH_3$ | H | $CH_3O$ | O |
| $CH_3CH_2$ | H | $CH_3$ | $CH_3$ | $CH_3O$ | O |
| $CH_3$ | 3-$CH_3$ | $CH_3O$ | $CH_3$ | $CH_3O$ | O |
| $CH_3$ | H | $CH_3(CH_2)_2$ | $CH_3(CH_2)_2$ | H | O |
| $CH_3$ | H | H | $(CH_3)_2CH$ | $CH_3O$ | O |
| $-CHCOOCH_3$<br>$\vert$<br>$CH_3$ | H | $CH_3$ | $CH_3$ | $CH_3O$ | O |
| 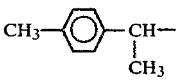 | 5-$CH_3$ | $CH_3O$ | $CH_3$ | H | O |
| $CH_3$<br>$\ \ \ \ CH(CH_2)_8-$<br>$CH_3$ | H | $CH_2{=}CHCH_2$ | $CH_2{=}CHCH_2$ | $CH_3O$ | O |
| $-CH_3$ | H | $CH_3$ | $CH_3$ | H | O |
| $-C_2H_5$ | H | $CH_3$ | $CH_3$ | Cl | O |
| $CHCO_2(CH_2)_3CH_3$<br>$\vert$<br>$CH_3$ | H | $-CH_2CH_2CH_2CH_2-$ | | $CH_3CH_2O$ | O |

TABLE V-c-continued

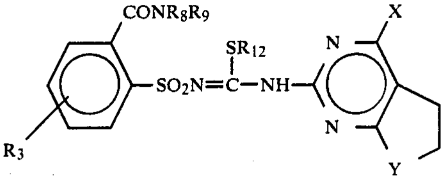

| $R_{12}$ | $R_3$ | $R_8$ | $R_9$ | X | Y |
|---|---|---|---|---|---|
| 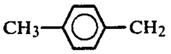 | 5-$CH_3O$ | $-CH_2CH_2CH_2CH_2CH_2-$ | | H | O |
| -n-$C_{12}H_{25}$ | H | $CH_3O$ | $CH_3$ | $CH_3$ | O |
| -n-$C_{10}H_{21}-$ | 6-Cl | H | H | $CH_3$ | O |
| $CH_3OCH_2CH_2$ | 5-F | H | $CH_3$ | $CH_3O$ | O |
| $CH_2CO_2CH_3$ | 5-$CH_3$ | $CH_3CH_2$ | $CH_3$ | H | O |
| $-CH-CO_2CH(CH_3)_2$<br>$CH_3$ | H | n-$C_4H_9$ | n-$C_4H_9$ | H | O |
| $CHC\equiv N$<br>$CH_3$ | H | $-CH_2CH_2CH_2CH_2CH_2-$ | | $CH_3$ | O |
| 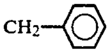 | H | $-CH_2CH_2OCH_2CH_2-$ | | $CH_3CH_2O$ | O |
| 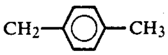 | 6-Cl | $CH_3O$ | $CH_3$ | $CH_3O$ | O |
| $CH_2CH\equiv CH_2$ | 5-$CH_3O$ | H | H | $CH_3O$ | O |
| $-CH_2CH_2CH_2OCH_3$ | H | $C_2H_5-$ | $CH_3$ | Cl | O |
| $-CH_2C\equiv N$ | H | $-CH(CH_3)_2$ | $CH_3$ | Cl | O |

TABLE V-d

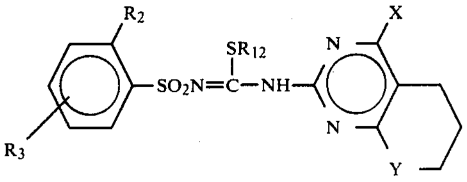

| $R_{12}$ | $R_2$ | $R_3$ | X | Y |
|---|---|---|---|---|
| $CH_3$ | $SO_2N(CH_3)_2$ | H | $CH_3$ | O |
| $-CH(CH_3)_2$ | $CO_2CH_3$ | H | $CH_3O$ | O |
| $-CHCH_2CH_3$<br>$CH_3$ | $SO_2N(C_2H_5)_2$ | H | $CH_3$ | O |
| $-(CH_2)_4CH(CH_3)_2$ | $CON(CH_3)_2$ | H | H | O |
| $-(CH_2)_7CH_3$ | 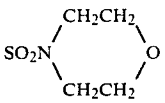 | H | $CH_3$ | O |
| $-(CH_2)_9CH_3$ | $SO_2N(CH_3)_2$ | H | $CH_3$ | O |
| $-(CH_2)_{11}CH_3$ | $CON(OCH_3)CH_3$ | 5-Cl | $C_2H_5O$ | O |
| $CH_2COOH$ | $SO_2N(CH_3)_2$ | H | $CH_3$ | O |
| $CHCOOH$<br>$CH_3$ | $SO_2N(OCH_3)CH_3$ | H | $CH_3O$ | O |
| $CH_2COOCH_3$ | 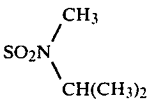 | H<br>H | Cl | O |

TABLE V-d-continued

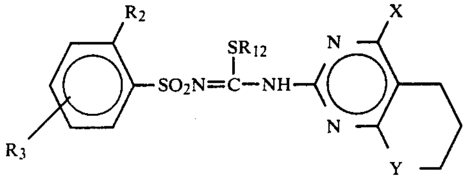

| $R_{12}$ | $R_2$ | $R_3$ | X | Y |
|---|---|---|---|---|
| $CHCOOC_2H_5$<br>$CH_3$ | O<br>‖<br>$CSCH_3$ | 5-$CH_3$ | $CH_3O$ | O |
| 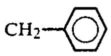 | $CO_2CH(CH_3)_2$ | H | $CH_3$ | O |
| 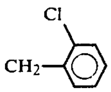 | $CON(C_2H_5)_2$ | H | $CH_3O$ | O |
| 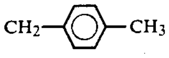 | $SO_2N(CH_3)_2$ | 6-$OCH_3$ | $C_2H_5O$ | O |
| $CH_2CH{=}CH_2$ | 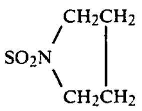 | H | $CH_3O$ | O |
| $-CH_2C\equiv CH$ | $CO_2CH_3$ | H | Cl | O |

TABLE V-d-continued

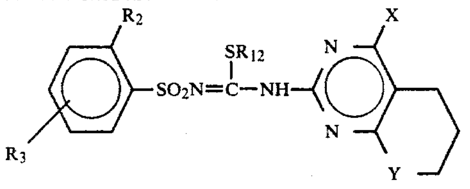

| $R_{12}$ | $R_2$ | $R_3$ | X | Y |
|---|---|---|---|---|
| $CH_2CH_2OCH_3$ | 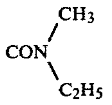 | H | $CH_3O$ | O |
| $CH_2CH_2CH_2OCH_3$ | $CO_2CH_2CH_2CH_3$ | 5-F | $CH_3$ | O |
| $CH_2C{\equiv}N$ | $SO_2N(OCH_3)CH_3$ | H | H | O |

TABLE V-e

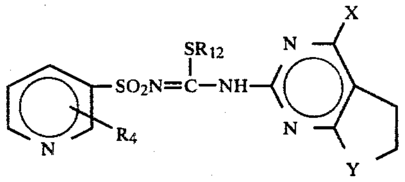

| $R_{12}$ | $R_4$ | X | Y |
|---|---|---|---|
| $CH_3$ | H | $CH_3O$ | O |
| $CH_3$ | 2-Cl | $CH_3$ | O |
| $CH_3(CH_2)_3$ | 4-F | $CH_3$ | O |
| $CH_3CH_2(CH_3)CH$ | $2\text{-}SCH_3$ | $CH_3O$ | O |
| $CH_3(CH_2)_3CH$<br>$CH_3$ | 2-Br | $CH_3O$ | O |
| $CH_3(CH_2)_3CH$<br>$CH_3$ | $2\text{-}OC_2H_5$ | $CH_3O$ | O |
| $CH_3OCH_2CH_2CH_2$ | $4\text{-}NO_2$ | $CH_3O$ | O |
| $CH_2COOH$ | 2-F | $CH_3O$ | O |
| $CH_2COOCH_3$ | $2\text{-}CH(CH_3)_2$ | $CH_3CH_2O$ | O |
| $CH{-}COOCH_3$<br>$CH_3$ | $4\text{-}OCH_3$ | $CH_3O$ | O |
| $CH_3CH_2$ | $2\text{-}SO_2CH_3$ | Cl | O |
| 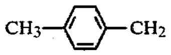 | 2-F | H | O |
| 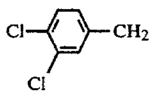 | $4\text{-}SCH_3$ | Cl | O |
| $CH_3O(CH_2)_3$ | 2-Br | H | O |
| 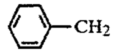 | $2\text{-}CO_2C_2H_5$ | H | O |
| $CH_2{=}CHCH_2CH_2$ | $2\text{-}NO_2$ | Cl | O |
| 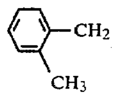 | 4-Cl | Cl | O |

TABLE V-f

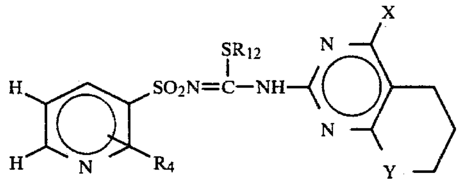

| $R_{12}$ | $R_4$ | X | Y | m.p. |
|---|---|---|---|---|
| $CH_3$ | 2-Cl | $CH_3O$ | O | |
| $CH_3CH_2$ | 4-Cl | H | O | |
| $CH_3(CH_2)_2$ | 2-F | $CH_3$ | O | |
| $CH_3$ | 4-Br | $C_2H_5O$ | O | |
| $(CH_3)_2CHCH_2$ | $4\text{-}NO_2$ | $CH_3O$ | O | |
| $-CH_2CH{=}CH_2$ | $2\text{-}C_2H_5$ | Cl | O | |
| 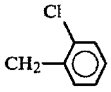 | $2\text{-}OCH_3$ | $CH_3$ | O | |
| $CHCOOH$<br>$CH_3$ | $4\text{-}CO_2C_2H_5$ | $CH_3$ | O | |
| $-CH_2COOH$ | $2\text{-}SC_2H_5$ | H | O | |
| 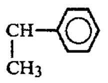 | 2-Cl | $CH_3$ | O | |
| $CH_3OCH_2CH_2$ | 2-Br | $C_2H_5O$ | O | |

The compounds of Table VI are useful as intermediates for the preparation of many of the ureas of Tables I through V. By application of one or more of the procedures of Examples 10 through 13 and/or the methods described above, and using the appropriate reactants, the compounds of Table VI can be prepared.

Conversion of these compounds to ureas can be accomplished by the procedure of Example 14 and/or the methods described above.

EXAMPLE 10

Methyl 2-[[(6,7-dihydro-4-methoxy-5H-cyclopentapyrimidin-2-yl)aminothioxomethyl]aminosulfonyl]benzoate A mixture of 4.3 g of methyl 2-(aminosulfonyl)-benzoate, 4.2 g of 6,7-dihydro-2-isothiocyanato-4-methoxy-5H-cyclopentapyrimidine and 2.2 g of anhydrous potassium carbonate in 70 ml of acetone was warmed to 40° with stirring. After 2 hours, a thick precipitate formed and stirring was continued for three more hours at ambient temperature. The precipitate was filtered, suspended in 150 ml of water, stirred and the pH adjusted to 2 by the addition of hydrochloric acid. The white solid was filtered, washed with cold water and dried to yield 4.2 g of product.

EXAMPLE 11

2-Chloro-N[(5,6-dihydro-4-methylfuro[2,3-d]pyrimidin-2-yl)aminothioxomethyl]benzenesulfonamide To a dry stirred mixture of 4.9 g of 5,6-dihydro-4-methylfuro[2,3-d]pyrimidin-2-amine in 125 ml of acetonitrile at ambient temperature was added 7.6 g of 2-chlorophenyl sulfonylisothiocyanate. The resulting mixture was stirred at reflux temperature (84°) for 24 hours. After cooling the reaction mixture, a white solid was filtered and washed with acetonitrile to yield 10.8 g of product, m.p. 190–191 dec. Elemental analyses, infrared spectrum and nuclear magnetic resonance spectrum indicated the title compound.

EXAMPLE 12

Methyl N-(6,7-dihydro-4-methyl-5H-cyclopentapyrimidin-2-yl)N'-(2,5-dimethoxyphenylsulfonyl)carbamimidothioate 1.5 grams of 6,7-dihydro-4-methyl-5H-cyclopentapyrimidin-2-amine was dissolved in a mixture of 20 ml of anhydrous tetrahydrofuran and 60 ml of anhydrous dimethylformamide. 0.48 grams of sodium hydride (50% mineral oil dispersion) was added. The reaction was stirred until hydrogen evolution ceased. 2.75 grams of N(2,5-dimethoxyphenylsulfonyl)carbonimidodithioic acid, 5,5-dimethyl ester was added all at once. The reaction mixture was stirred 24 hours at ambient temperature. The mixture was poured into 300 ml of water and acidified to pH 5 with 20% hydrochloric acid. The mixture was filtered. The solid obtained was recrystallized from ethyl acetate to yield 1 g of product.

EXAMPLE 13

Methyl 2-[[1-(6,7-dihydro-4-methoxy-5H-cyclopentapyrimidin-2-yl-amino)-1-(ethylthio)methylene]aminosulfonyl]benzoate To a suspension at 4.2 g of methyl 2-[[(6,7-dihydro-4-methoxy-5H-cyclopentapyrimin-2-yl)aminothioxomethyl]aminosulfonyl]benzoate in 200 ml of anhydrous tetrahydrofuran was added 4.3 ml of 3 M $NaOCH_3/CH_3OH$ solution. The reaction was refluxed for 5 min. whereupon 2 g of ethyl iodide in 10 ml of anhydrous tetrahydrofuran was added. After refluxing and stirring for an additional 6 hours, the reaction mixture was cooled, solvent was removed under vacuum and the residue was recrystallized from acetonitrile to yield 0.5 g of the product.

EXAMPLE 14

Methyl 2-[[(6,7-dihydro-4-methoxy-5H-cyclopentapyrimidin-2-yl)aminocarbonyl]aminosulfonyl]benzoate A solution of 3.2 g of methyl 2-[[1-(6,7-dihydro-4-methoxy-5H-cyclopentapyrimidin-2-ylamino)-1-(ethylthio)methylene]aminosulfonyl]benzoate in 75 ml of acetone is treated with 3.0 g of mercuric oxide and stirred at room temperature for 3 days. The mercury salts are removed by filtration and the solvent is evaporated to yield the solid product.

TABLE VI-a

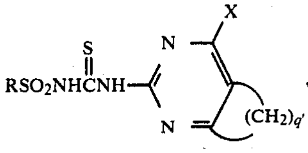
wherein R is
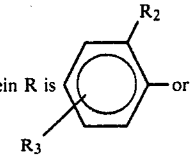
or
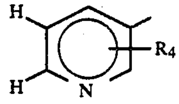
and q' = 3 or 4

| $R_2$ | $R_3$ | $R_4$ | q' | X | m.p.(°C.) |
|---|---|---|---|---|---|
| $CO_2CH_3$ | H | — | 3 | $OCH_3$ | |
| Cl | H | — | 3 | $OCH_3$ | 198–199° |
| Cl | H | — | 3 | $CH_3$ | 190–191° |
| $SCH_3$ | H | — | 3 | $CH_3$ | |
| $SO_2CH_3$ | H | — | 4 | $CH_3$ | |
| $NO_2$ | 5-Cl | — | 4 | $OCH_3$ | |
| $CH_3$ | H | — | 4 | $OC_2H_5$ | |
| $CON(CH_3)_2$ | H | — | 3 | $CH_3$ | |
| 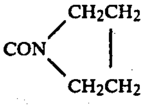 | H | — | 4 | $CH_3$ | |
| F | H | — | 3 | $OCH_3$ | |
| $CO_2C_2H_5$ | H | — | 4 | $CH_3$ | |
| $CO_2CH_2CH{=}CH_2$ | H | — | 3 | H | |
| $CO_2CH(CH_3)_2$ | H | — | 4 | H | |
| $SO_2N(CH_3)_2$ | H | — | 4 | $CH_3$ | |
| $SO_2N(OCH_3)CH_3$ | 5-Br | — | 3 | $OCH_3$ | |
| Br | H | — | 4 | Cl | |
| $CON(C_2H_5)_2$ | H | — | 3 | Cl | |
| $CF_3$ | H | — | 3 | H | |
| $SO_2OCH_2CF_3$ | H | — | 4 | $CH_3$ | |
| — | — | H | 3 | $CH_3$ | |
| — | — | 2-Cl | 4 | $CH_3$ | |
| — | — | 2-Br | 3 | $CH_3$ | |
| — | — | 2-$NO_2$ | 4 | $OCH_3$ | |
| — | — | 2-$CO_2CH_3$ | 3 | $OCH_3$ | |
| — | — | 4-$NO_2$ | 4 | $OCH_3$ | |
| — | — | 4-$OCH_3$ | 3 | $OCH_3$ | |
| — | — | 2-$CH(CH_3)_2$ | 4 | $CH_3$ | |
| — | — | 2-F | 4 | $CH_3$ | |
| — | — | 4-$OCH_2CH_3$ | 3 | $OCH_3$ | |
| — | — | 4-Br | 3 | $OCH_2CH_3$ | |

TABLE VI-b

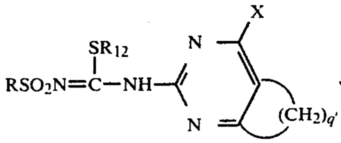
wherein R is
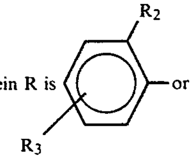
or
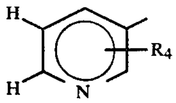
and q' = 3 or 4

| $R_{12}$ | $R_2$ | $R_3$ | $R_4$ | q' | X | m.p.(°C.) |
|---|---|---|---|---|---|---|
| $C_2H_5$ | Cl | H | — | 3 | $CH_3$ | 162–163° |
| $CH_3$ | Br | H | — | 4 | $CH_3$ | |
| $CH_3$ | $NO_2$ | 5-Cl | — | 4 | $OCH_3$ | |
| $C_{12}H_{25}$ | $CH_3$ | H | — | 4 | $OCH_3$ | |
| $CH_3$ | $CO_2CH_3$ | H | — | 3 | H | |

TABLE VI-b-continued

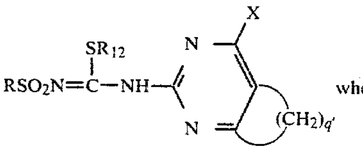 wherein R is 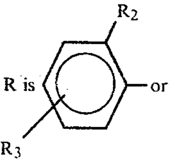 or

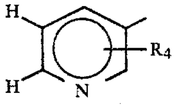 and q' = 3 or 4

| $R_{12}$ | $R_2$ | $R_3$ | $R_4$ | q' | X | m.p.(°C.) |
|---|---|---|---|---|---|---|
| $CH_3$ | $CON(CH_3)_2$ | H | — | 3 | H | |
| $CH_3$ | $CON(C_2H_5)_2$ | H | — | 3 | $CH_3$ | |
| $C_2H_5$ | $CON(OCH_3)CH_3$ | H | — | 4 | $CH_3$ | |
| $C_4H_9$ | $CONHCH_3$ | H | — | 4 | $CH_3$ | |
| $CH_3$ | $SO_2N(CH_3)_2$ | 5-$NO_2$ | — | 4 | $OCH_3$ | |
| $CH_2CO_2CH_3$ | $SO_2C_2H_5$ | H | — | 4 | $OCH_3$ | |
| $CH_2C_6H_5$ | $SO_2OCH_2CF_3$ | 3-F | — | 3 | $OCH_3$ | |
| $CH(CH_3)CO_2CH_3$ | $CF_3$ | H | — | 3 | $OC_2H_5$ | |
| $CH_2CH{=}CH_2$ | $CO_2CH_2CH_3$ | H | — | 3 | $OC_2H_5$ | |
| $CH_2C{\equiv}CH$ | Cl | 6-$NO_2$ | — | 3 | Cl | |
| $CH_2CH_2OCH_3$ | $CO_2CH(CH_3)_2$ | H | — | 4 | Cl | |
| $CH_2CO_2H$ | $OCH_3$ | H | — | 4 | H | |
| 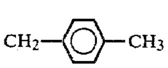 | — | — | 4-Cl | 4 | H | |
| $CH_3$ | — | — | 2-$NO_2$ | 4 | $CH_3$ | |
| 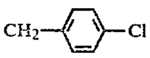 | — | — | 4-$CO_2CH_3$ | 3 | $CH_3$ | |
| $CH_3$ | — | — | 2-Br | 3 | $CH_3$ | |
| 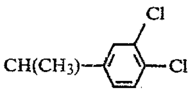 | — | — | 2-$OCH_3$ | 3 | $OCH_3$ | |
| $C_3H_7$ | — | — | 4-$CH_2CH_3$ | 3 | $OCH_3$ | |
| $CH(CH_3)CO_2C_2H_5$ | — | — | 2-Cl | 4 | $OCH_3$ | |

Formulations

Useful formulations of the compounds of Formulas I and II can be prepared in conventional ways. They include dusts, granules, pellets, suspensions, emulsions, wettable powders, emulsifiable concentrates and the like. Many of these can be applied directly. Sprayable formulations can be extended in suitable media and used at spray volumes of from a few liters to several hundred liters per hectare. The formulations, broadly, contain about 0.1% to 99% by weight of active ingredient(s) and at least one of (a) about 0.1% to 20% surfactant(s) and (b) about 1% to 99.9% solid or liquid diluents(s). More specifically, they will contain these ingredients in the approximate proportions set forth in Table VII.

TABLE VII

| | Weight Percent* | | |
|---|---|---|---|
| | Active Ingredient | Diluent(s) | Surfactant(s) |
| Wettable Powders | 20-90 | 0-74 | 1-10 |
| Oil Suspensions, Solutions, Emulsions (including Emulsifiable Concentrates) | 3-50 | 40-95 | 0-15 |
| Aqueous Suspensions | 10-50 | 40-84 | 1-20 |
| Dusts | 1-25 | 70-99 | 0-5 |

TABLE VII-continued

| | Weight Percent* | | |
|---|---|---|---|
| | Active Ingredient | Diluent(s) | Surfactant(s) |
| Granules and Pellets | 0.1-95 | 5-99.9 | 0-15 |

*Active Ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation, or by tank mixing.

Some typical solid diluents are described in Watkins, et al., "Handbook of Insecticide Dust Diluents and Carriers", 2nd Ed., Dorland Books, Caldwell, New Jersey, but other solids, either mined or manufactured, may be used. The more absorptive diluents are preferred for wettable powders and the denser ones for dusts. Typical liquid diluents and solvents are described in Marsden, "Solvents Guide", 2nd Ed., Interscience, New York, 1950. Solubility under 0.1% is preferred for suspension concentrates, solution concentrates are preferably stable against phase separation at 0° C.

"McCutcheon's Detergents and Emulsifiers Annual", MC Publishing Corp., Ridgewood, New Jersey, as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending, and usually, grinding as in a hammer or fluid energy mill. Suspensions are prepared by wet milling (see for example, Littler, U.S. Pat. No. 3,060,084). Granules and pellets may be made by spraying the active material on preformed granular carriers or by agglomeration techniques. See J. E. Browning, "Agglomeration", *Chemical Engineering, Dec.* 4, 1967, pp. 147ff. and "Perry's Chemical Engineer's Handbook", 4th Ed., McGraw-Hill, New York, 1963, pp. 8-59ff.

For further information regarding the art of formulation, see for example:

H. M. Loux, U.S. Pat. No. 3,235,361, Col. 6, line 16 through Col. 7, line 19 and Examples 10 through 41.

R. W. Luckenbaugh, U.S. Pat. No. 3,309,192, Col. 5, line 43 through Col. 7, line 62 and Examples 8, 12, 15, 39, 41, 52, 53, 58, 132, 138-140, 162-164, 166, 167, 169-182.

H. Gysin and E. Knusli, U.S. Pat. No. 2,891,855, Col. 3, line 66 through Col. 5, line 17 and Examples 1-4.

G. C. Klingman, "Weed Control as a Science", John Wiley & Sons, Inc., New York, 1961, pp. 81-96.

J. D. Fryer and S. A. Evans, "Weed Control Handbook", 5th Ed., Blackwell Scientific Publications, Oxford, 1968, pp. 101-103.

The disclosures of the above-cited references are herein incorporated by reference.

Unless indicated otherwise, all parts are by weight in the following examples.

EXAMPLE 15

| Wettable Powder | |
|---|---|
| N-[(6,7-dihydro-4-methyl-5H-cyclopentapyrimidin-2-yl)-aminocarbonyl]-2-nitrobenzenesulfonamide | 40% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S. No. 50 sieve (0.3 mm opening) before packaging.

EXAMPLE 16

| Granule | |
|---|---|
| wettable powder of Example 15 | 10% |
| attapulgite granules (U.S.S. #20-40; 0.84-0.42 mm) | 90% |

A slurry of wettable powder containing 25% solids is sprayed on the surface of attapulgite granules in a double-cone blended. The granules are dried and packaged.

EXAMPLE 17

| Wettable Powder | |
|---|---|
| N-[(6,7-dihydro-4-methoxy-5H-cyclopentapyrimidin-2-yl)-aminocarbonyl]-2-nitrobenzenesulfonamide | 80% |
| Sodium alkylnaphthalenesulfonate | 2% |
| sodium ligninsulfonate | 2% |
| synthetic amorphous silica | 3% |
| kaolinite | 13% |

The ingredients are blended and ground in a hammer mill to produce an average particle size under 100 microns. The material is reblended, sifted through a U.S.S. #50 sieve and packaged.

EXAMPLE 18

| Granule | |
|---|---|
| wettable powder of Example 17 | 15% |
| gypsum | 69% |
| potassium sulfate | 16% |

The ingredients are blended in a rotating mixer and water sprayed on to accomplish granulation. When most of the material has reached the desired range of 1.0 to 0.42 mm. (U.S.S. #18 to 40 sieves), the granules are removed, dried, and screened. Oversize material is crushed to produce additional material in the desired range. These granules contain 12% active ingredient.

EXAMPLE 19

| Wettable Powder | |
|---|---|
| N-[(6,7-dihydro-4-methyl-5H-cyclopentapyrimidin-2-yl)-aminocarbonyl]-2-(methoxycarbonyl)benzenesulfonamide | 65% |
| dodecylphenol polyethylene glycol ether | 2% |
| sodium ligninsulfonate | 4% |
| sodium silicoaluminate | 6% |
| montmorillonite (calcined) | 23% |

The ingredients are thoroughly blended. The liquid surfactant is added by spraying upon the solid ingredients in the blender. After grinding in a hammer mill to produce particles essentially all below 100 microns, the material is reblended, sifted through a U.S.S. No. 50 sieve (0.3 mm opening) and packaged.

EXAMPLE 20

| High Strength Concentrate | |
|---|---|
| N-[(6,7-dihydro-4-methoxy-5H-cyclopentapyrimidin-2-yl)-aminocarbonyl]-2-nitrobenzenesulfonamide | 98.5% |
| silica aerogel | 0.5% |
| synthetic amorphous fine silica | 1.0% |

The ingredients are blended and ground in a hammer mill to produce a high strength concentrate essentially all passing a U.S.S. No. 50 sieve (0.3 mm openings). This material may then be formulated in a variety of ways.

EXAMPLE 21

| Aqueous Suspension | |
|---|---|
| N-[(6,7-dihydro-4-methyl-5H-cyclopentapyrimidin-2-yl) aminocarbonyl]2-(methoxycarbonyl)benzenesulfonamide | 25% |
| hydrated attapulgite | 3% |
| crude calcium ligninsulfonate | 10% |
| sodium dihydrogen phosphate | 0.5% |
| water | 61.5% |

The ingredients are ground together in a ball or roller mill until the solid particles have been reduced to diameters under 10 microns.

EXAMPLE 22

| Oil Suspension | |
|---|---|
| N-[(6,7-dihydro-4-methyl-5H-cyclopentapyrimidin-2-yl)-aminocarbonyl-2-nitrobenzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting suspension may be applied directly, but preferably after being extended with oils or emulsified in water.

EXAMPLE 23

| Extruded Pellet | |
|---|---|
| N-[(6,7-dihydro-4-methyl-5H-cyclopentapyrimidin-2-yl)-aminocarbonyl]-2-(methoxycarbonyl)benzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

Utility

The compounds of the present invention are powerful herbicides. They have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, the subject compounds are useful for the selective pre- or post-emergence weed control in crops, such as wheat and soybeans.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.02 to 10 kg/ha, the lower rates being suggested for use on lighter soils and/or those having a low organic matter content, for selective weed control or for situations where only short-term persistence is required.

The compounds of the invention may be used in combination with any other commercial herbicide examples of which are those of the triazine, triazole, uracil, urea, amide, diphenylether, carbamate and bipyridylium types.

The herbicidal properties of the subject compounds were discovered in a number of greenhouse tests. The test procedures and results follow.

Test A

Seeds of crabgrass (Digitaria spp.), barnyardgrass (*Echinochloa crusgalli*), wild oats (*Avena fatua*), *Cassia tora,* morningglory (Ipomeoea spp.), cocklebur (Xanthium spp.), Sorghum, corn, soybean, rice, wheat as well as nutsedge tubers were planted in a growth medium and treated preemergence with the chemicals dissolved in a non-phytotoxic solvent. At the same time, cotton having five leaves (including cotyledonary ones), bush beans with the third trifoliolate leaf expanding, crabgrass, barnyardgrass and wild oats with two leaves, cassia with three leaves (including cotyledonary ones), morningglory and cocklebur with four leaves (including the cotyledonary ones), sorghum and corn with four leaves, soybean with two cotyledonary leaves, rice with three leaves, wheat with one leaf, and nutsedge with three-five leaves were sprayed. Treated plants and controls were maintained in a greenhouse for sixteen days, whereupon all species were compared to controls and visually rated for response to treatment. The ratings are based on a numerical scale extending from 0=no injury, to 10=complete kill. The accompanying descriptive symbols have the following meanings: G=growth retardation; C=chlorosis/necrosis; D=defoliation; S=albinism; 6F=delayed flowering; 6Y=abscised buds or flowers; U=unusual pigmentation; E=emergence inhibition; X=axillary stimulation; and H=formative effects. The ratings for the compounds tested by this procedure are presented in Table A. It will be seen that certain of the compounds tested have utility for selective pre-emergence weed control in wheat and soybeans.

TABLE A
| | kg/ha | Bush-bean | Cotton | Post-emergence Morning-glory | Cockle-bur | Cassia | Nut-sedge | Crab-grass | Barn-yard grass | Wild oats | Wheat | Corn | Soybean | Rice | Sorghum |
|---|---|---|---|---|---|---|---|---|---|---|---|---|---|---|---|
| 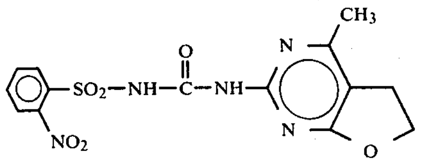 | 0.4 | 9C | 9G,6C | 10C | 9C | 9C | 10C | 9C | 10C | 9G,5C | 8G,2C | 9H,5U | 9C | 9C | 9H,2U |
| 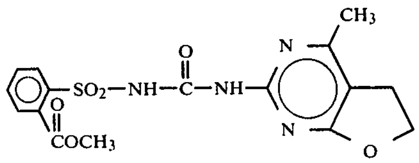 | 0.4 | 9C | 10C | 10C | 9C | 9C | 2C,8G | 5C,8G | 9C | 9C | 9C | 9C | 9C | 6C,9G | 9C |
| 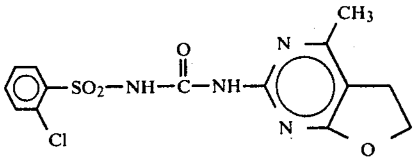 | 2 | 9C | 9C | 10C | 9C | 9C | 8C | 9C | 9C | 9C | 8C | 9U,9G | 9C | 5C,8G | 5U,9G |
| " | 0.4 | 9C | 6C,9G | 8C | 9C | 9C | 5C,9G | 9C | 6C,9G | 3C,7G | 3C,8G | 9C | 6C,9G | 5C,9G | 9G |
| 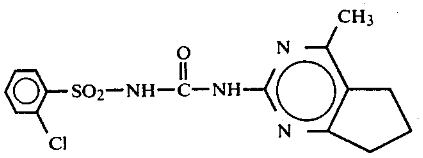 | 2 | 9D,9G | 3C,5G | 3C,9G | 5C,9G | 3C | 4G | 2C,6G | 2C | 1C | 2C | 1C,5H | 6H | 8G | 8H |
| " | 0.4 | 5C,7G,6Y | 1C,2G | 1C,8G | 2C,7G | 1H | 2C | 2C | 2C | 0 | 0 | 6H | 8H | 5G | 6H |
| 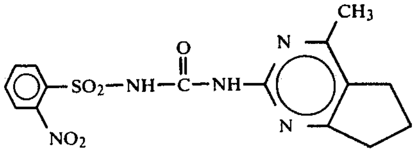 | 0.4 | 6C,8G,6Y | 3C,5G | 10C | 9C | 1C,8G | 5C,9G | 3C,8G | 3C,8H | 2C | 1C,6G | 2C,9H | 3H,9G | 5C,9G | 7H |

TABLE A-continued
| | | | | | | | | | | | | | | | |
|---|---|---|---|---|---|---|---|---|---|---|---|---|---|---|---|
| 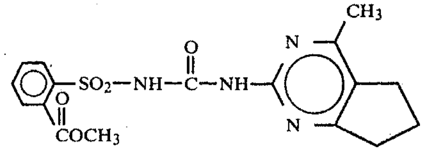 | 2 | 9C | 8C,9G | 10C | 10C | 5C,8G | 9C | 9C | 10C | 5C,8G | 5U,8G | 9C | 9C | 9C | 9C |
| " | 0.4 | 9C | 9C,9G | 10C | 10C | 5C,8G | 10C | 9C | 10C | 5C,9G | 5U,8G | 10C | 9C | 9C | 9C |
| 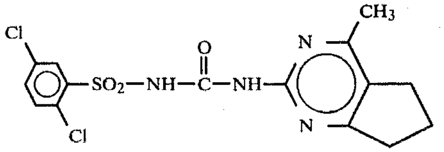 | 2 | 1C | 0 | 1C | 0 | 0 | 0 | 0 | 0 | 0 | 0 | 0 | 0 | 0 | 0 |
| " | 0.4 | 0 | 0 | 2C | 0 | 0 | 0 | 0 | 0 | 0 | 0 | 0 | 0 | 0 | 0 |
| 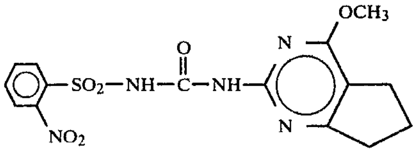 | 2 | 5C,9G | 2C,2H,4G | 10C | 2C,9G | 5C,7G | 0 | 3C,7G | 9C | 2C,6G | 1C,6G | 2C,9H | 1C,9H | 5C,9G | 3H,9G |
| " | 0.4 | 5C,9G | 2C,2H | 5C,9G | 1C | 5C,9G | 0 | 2C,7G | 3C,7H | 3G | 2G | 1C,4H | 6H | 5C,9G | 1C,6G |
| 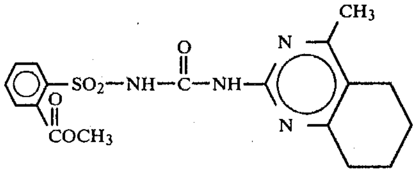 | 2 | 9D,9G | 5C,6G | 5C,7G | 1C | 4H | 2C,7G | 1C,5G | 2C,9H | 2C,7G | 9H | 9H | 5H,9G | 4C,9G | 2C,9G |
| 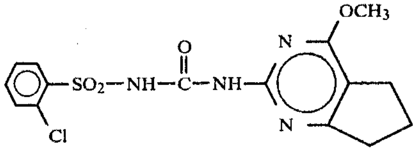 | 2 | 2C | 1C | 1C | 0 | 1C | 0 | 0 | 2H | 0 | 0 | 6H | 6H | 5G | 5G |
| " | 0.4 | 1C,1H | 0 | 0 | 0 | 0 | 0 | 0 | 0 | 0 | 0 | 0 | 0 | 0 | 0 |

TABLE A-continued
| | | | | | | | | | | | | | | | |
|---|---|---|---|---|---|---|---|---|---|---|---|---|---|---|---|
| 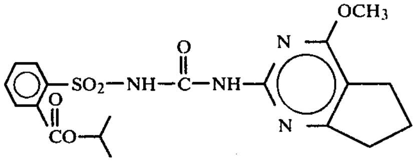 | 0.4 | 9C | 2C,6G | 5C,9G | 2C | 3C | 2G | 1C | 2C,7G | 1C | 1C | 1C,6G | 3C,8G | 7G | 1C,6G |
| 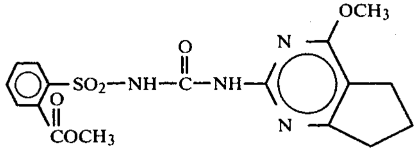 | 0.4 | 9C | 2C,6G | 9C | 1C,3H | 2C,7G | 2G | 2C,7G | 5C,9H | 1C,8G | 2C,7G | 2C,9G | 5C,9G | 3C,8G | 2C,9G |
| 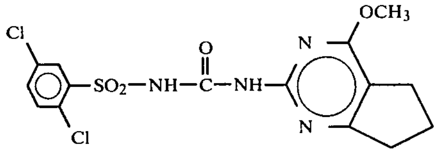 | 0.4 | 3C,5G,6Y | 1C | 3G | 1C | — | 0 | 0 | 0 | 0 | 0 | 0 | 0 | 0 | 0 |
| 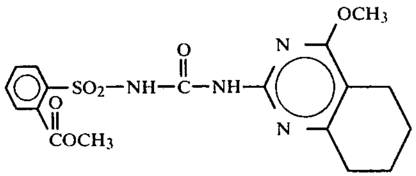 | 0.4 | 8C | 2C | 5C,8G | 2C | 1C | 2G | 0 | 3C,5G | 1C | 0 | 1C,3G | 1C | 1C,3G | 2C,7G |
| 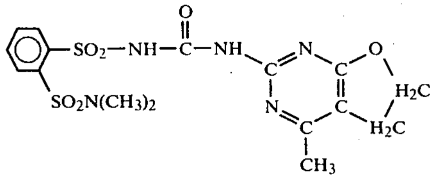 | 1/10 | 9D,9G,6Y | 5C,9G | 9C | 3C,9G | 3C,9G | 1C,7G | 9C | 10C | 9C | 1C,7G | 9C | 9C | 9C | 10C |
| 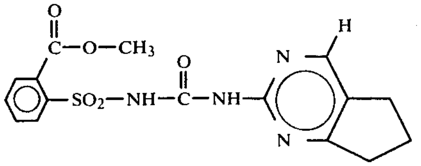 | 2 | 5C,9G,6Y | 3C,9G | 10C | 1C,8G | 2C,5G | 1C,9G | 1C,7G | 9C | 1C,7G | 4C,8G | 5C,9G | 3C,9G | 3C,9G | 2C,9G |
| " | 0.4 | 6C,9G,6Y | 2C,2H,8G | 2C,5G | 2C | 3C | 7G | 2G | 3C,9H | 3C,5G | 2C,4G | 2C,7H | 2C,8G | 5C,9G | 9G |

TABLE A-continued
| | | | | | | | | | | | | | | | |
|---|---|---|---|---|---|---|---|---|---|---|---|---|---|---|---|
| 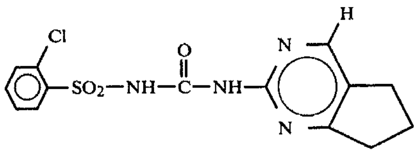 | 2 | 2H,6F | 1H | 2H | 1C | 0 | 0 | 0 | 0 | 0 | 0 | 0 | 4H | — | 0 |
| " | 0.4 | 0 | 0 | 1H | 0 | 0 | 0 | 0 | 0 | 0 | 0 | 0 | 2H | 0 | 0 |
| 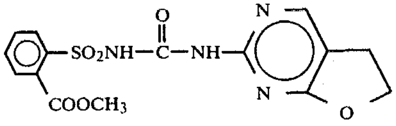 | 0.4 | 7C 9G | 6C 9G | 5C 9G | 9C | 5C 7G | 1C 8G | 9C | 9C | 9C | 9C | 3U 9G | 10C | 9C | 9C |
| 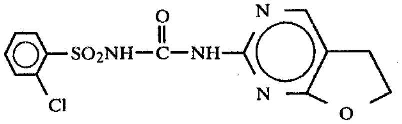 | 2 | 6C 9G 6Y | 9C | 10C | 10C | 9C | 1C 9G | 9C | 9C | 1C 3G | 2C 7G | 2C 9G | 6C 9G | 7G | 2C 9G |
| " | 0.4 | 6C 8G 6Y | 5C 9G | 10C | 9C | 3C 6G | 3G | 2C 8G | 9C | 0 | 1C 5G | 2C 7H | 3C 8G | 2C 7G | 1C 7H |
| 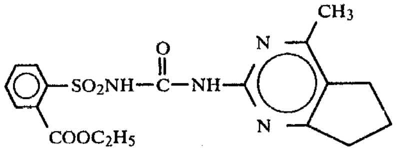 | 0.4 | 9D 9G 6Y | 9C | 10C | 3C 9G | 5C 9G | 1C 8G | 3C 6G | 5C 9H | 2C 8H | 3C 7G | 8U 9G | 3C 9G | 6C 9G | 3C 9G |
| 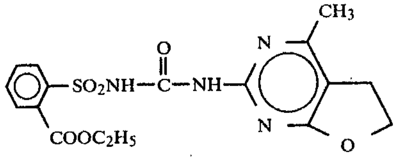 | 0.4 | 7C 9G | 9C | 10C | 9C | 9C | 4C 9G | 4C 9G | 10C | 5C 9G | 4C 9G | 9C | 9C | 5C 9G | 10C |
| 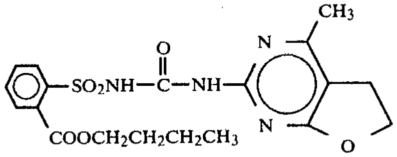 | 0.4 | 3C 9G 6Y | 4C 9G | 10C | 3C 9G | 3C 5G | 2G | 2G | 3C 9H | 8G | 6G 5X | 2C 9H | 3C 9G | 5C 9G | 5C 9G |

TABLE A-continued
| | | | | | | | | | | | | | | | |
|---|---|---|---|---|---|---|---|---|---|---|---|---|---|---|---|
| 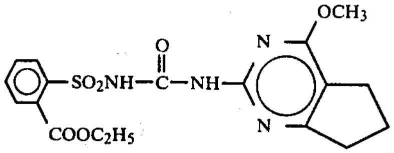 | 0.4 | 6C 9G 6Y | 3C 3H 9G | 10C | 1C 4G | 2C 6G | 5G | 5C 9G | 5C 9H | 1C 5G | 1C 5G | 4C 9G | 2C 8G 5X | 7C | 2C 9G |
| 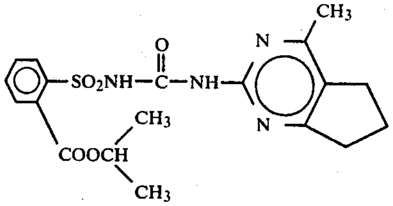 | 0.4 | 5C,9G | 5C,9G | 9C | 5C,9G | 3C | 0 | 1C,5G | 3C,9H | 4G | 0 | 8H | 2C,9G | 9C | 9H |
| 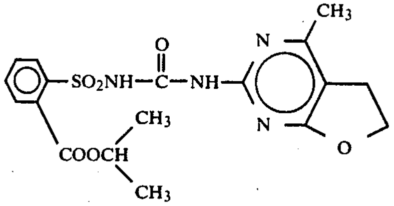 | 0.4 | 3S,9G,6Y | 2C,7G | 2C,9G | 1C,6G | 2C,5G | 0 | 2G | 2C,5H | 0 | 0 | 1C,8G | 1C,6G | 1C,3G | 1C,7H |
| 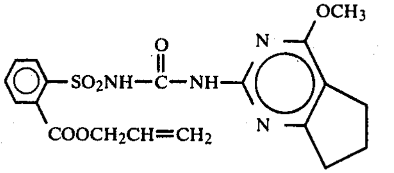 | 0.4 | 3S,9G,6Y | 2C,2H,8G | 3C,9H | 3C,9G | 3C,4H | 1C,4G | 0 | 4H | 0 | 0 | 2C,9H | 2H,8G | 1C | 2C,9H |
| 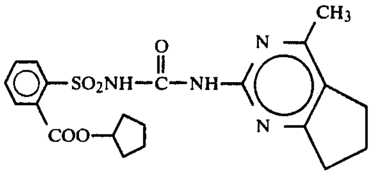 | 0.4 | 4S,7G,6Y | 3C,5G | 9C | 1C,3H | 1C | 0 | 0 | 1C,5H | 0 | 0 | 2C,7G | 2C,8G | 1C,7G | 2C,9G |

TABLE A-continued
| | | | | | | | | | | | | | | | |
|---|---|---|---|---|---|---|---|---|---|---|---|---|---|---|---|
| 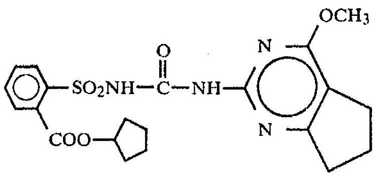 | 0.4 | 2C,6G | 1C,3G | 1C | 1C | 0 | 0 | 1C,3G | 1C,4G | 0 | 0 | 1C,3H | 4H | 2C,7G | 2C,7G |
| 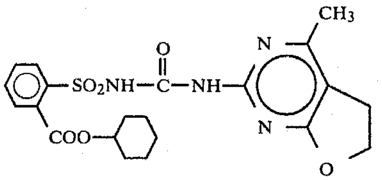 | 0.4 | 5C,8G,6Y | 3C,2H | 10C | 2C,9H | 2C,9G | 2G | 2C,4G | 2C,8H | 1C,2G | 1C,6G | 2C,9H | 3C,6G | 1C,9G | 2C,9H |
| 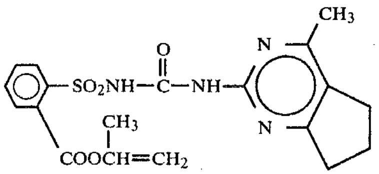 | 0.4 | 9D,9G,6Y | 3C,3H,9G | 10C | 3C,8G | 1C,5G | 1C,5G | 2C | 2C,9H | 0 | 4G | 2C,9H | 2C,7G,5X | 2C,9G | 2C,9G |
| 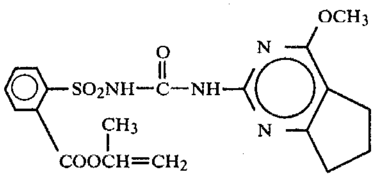 | 0.4 | 3C,7G,6Y | 3B | 1C,9G | 2H | 1C,4G | 0 | 3G | 1C,3H | 0 | 0 | 6G | 2H,6G | 5G | 3G |
Pre-emergence
| | kg/ha | Morning-glory | Cockle-bur | Cassia | Nut-sedge | Crab-grass | Barn-yard grass | Wild oats | Wheat | Corn | Soybean | Rice | Sorghum |
|---|---|---|---|---|---|---|---|---|---|---|---|---|---|
| 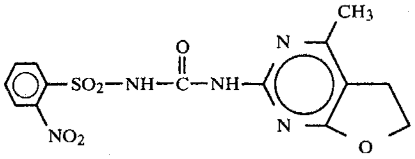 | 0.4 | 9G | 9G | 9G | 10E | 9G,5C | 9H | 9G,2C | 9H | 9G | 9H | 10E | 9G,1C |

TABLE A-continued
| | | | | | | | | | | | | | |
|---|---|---|---|---|---|---|---|---|---|---|---|---|---|
| 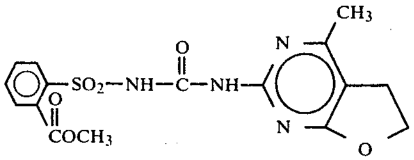 | 0.4 | 9G | 9G | 9G | 10E | 10E | 10H | 5C,9H | 9H | 10H | 9H | 10E | 9H |
| 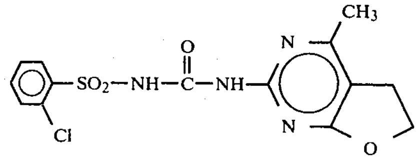 | 2 | 9G | 9G | 9G | 10E | 1C,9G | 9H | 1C,8G | 9H | 9G | 9H | 10E | 5C,9H |
| " | 0.4 | 9G | 9G | 9G | 10E | 2C,9G | 5C,9H | 1C,9G | 9H | 1C,9G | 9H | 10E | 1C,9G |
| 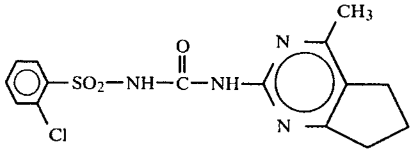 | 2 | 9G | 9G | 8G | 9G | 3G | 9H | 2G | 5G | 2C,8G | 3H | 9H | 8H |
| " | 0.4 | 9G | 9G | 1C,7G | 8G | 2G | 7G | 0 | 0 | 1C,6G | 2H | 9H | 1C,8H |
| 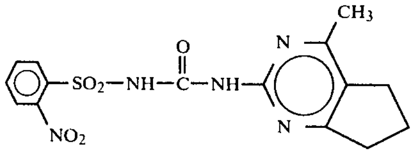 | 0.4 | 9G | 9G | 7G | 9G | 4G | 9H | 6G | 8G | 2C,9G | 5H | 9H | 2C,9G |
| 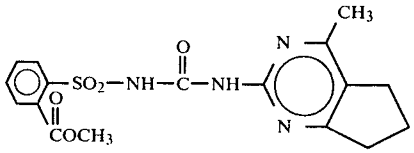 | 2 | 9C | 9G | 9G | 10E | 9H | 10H | 2C,8G | 10H | 10E | 10E | 10E | 10H |
| " | 0.4 | 9G | 9G | 9G | 10E | 9H | 10H | 2C,9G | 10E | 10E | 9H | 10E | 10H |

TABLE A-continued
| | | | | | | | | | | | | | |
|---|---|---|---|---|---|---|---|---|---|---|---|---|---|
| 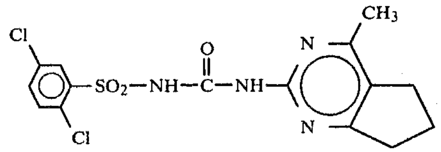 | 2 | 9G | 9G | 2H | 0 | 0 | 0 | 0 | 0 | 0 | 0 | 3G | 2G |
| " | 0.4 | 5G | 4G | 0 | 0 | 0 | 0 | 0 | 0 | 0 | 0 | 0 | 0 |
| 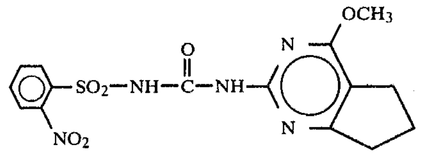 | 2 | 9G | 9G | 10E | 9G | 2C,9G | 9H | 2C,8H | 9G | 2C,9G | 9H | 10E | 9H |
| " | 0.4 | 9G | 8G | 9G | 6G | 7G | 9H | 8G | 8G | 2C,9G | 8H | 9H | 9G |
| 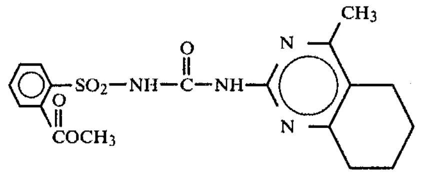 | 2 | 9G | 9G | 7G | 9G | 4G | 9H | 7G | 9G | 9G | 4H | 10E | 9H |
| 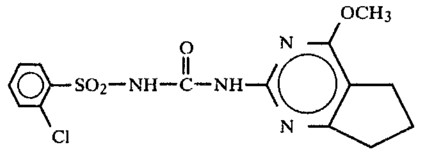 | 2 | 4G | 2G | 6G | 5G | 0 | 2C,5G | 1C | 1C | 3G | 0 | 8H | 2G |
| " | 0.4 | 9G | 8G | 5G | 0 | 3G | 5G | 0 | 0 | 3G | 0 | 7G | 4G |
| 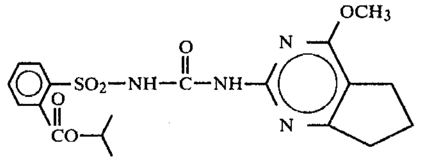 | 0.4 | 8G | 8G | 2G | 8G | 0 | 1C,9G | 1G | 1G | 1C,5G | 1H | 8H | 2C,8G |

TABLE A-continued
| | | | | | | | | | | | | | |
|---|---|---|---|---|---|---|---|---|---|---|---|---|---|
| 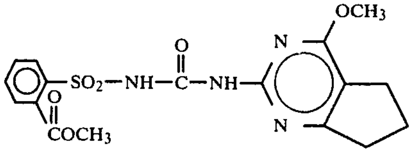 | 0.4 | 9G | 9G | 9G | 9G | 3C,8G | 9H | 2C,8G | 9H | 2C,9G | 8H | 10E | 10H |
| 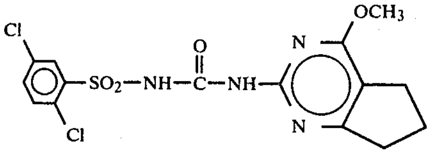 | 0.4 | 3G | 0 | 0 | 0 | 0 | 0 | 0 | 0 | 0 | 0 | 0 | 1C |
| 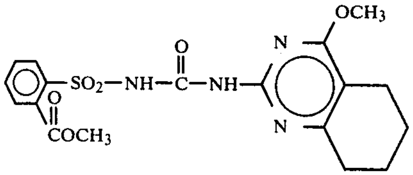 | 0.4 | 8G | 8G | 0 | 0 | 1C | 2C,8H | 2G | 2G | 1C,3G | 0 | 1C,7G | 1C,8G |
| 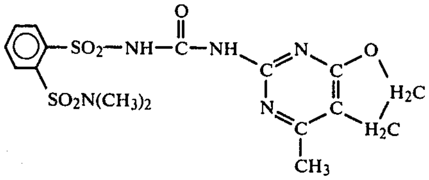 | 1/10 | 9G | 9G | 1C,9G | 10E | 1C,9G | 2C,9H | 2C,9G | 9G | 1C.9G | 9H | 10E | 9H |
| 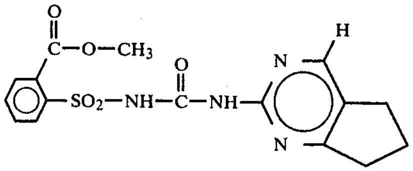 | 2 | 9G | 9G | 1C,9G | 10E | 4G | 2C,9H | 2C,9G | 9G | 3U,9G | 9H | 10E | 10H |
| " | 0.4 | 9G | — | 8G | 9G | 0 | 2C,9H | 8G | 5G | 1C,9G | 2C,8H | 10E | 2C,9H |
| 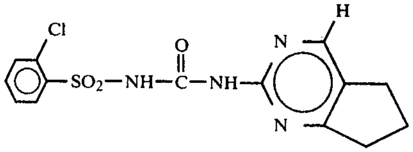 | 2 | 7G | 8G | 5H | 0 | 0 | 2C | 0 | 0 | 2C | 1C,5H | 2G | 0 |

TABLE A-continued
| | | | | | | | | | | | | | |
|---|---|---|---|---|---|---|---|---|---|---|---|---|---|
| " | 0.4 | 5G | 5G | 0 | 0 | 0 | 0 | 0 | 0 | 0 | 0 | 0 | 0 |
| 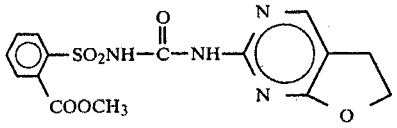 | 0.4 | 9G | 9G | 9G | 10E | 1C 9G | 5C 9H | 4C 9H | 2C 9H | 9G | 9H | 10E | 9H |
| 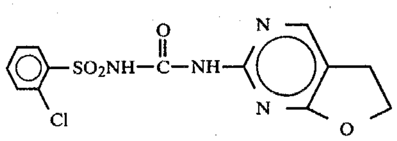 | 2 | 9G | 9H | 9G | 10E | 1C 8G | 9H | 6G | 8H | 1C 9G | 9H | 10E | 1C 9G |
| " | 0.4 | 9G | 9H | 7G | 9G | 2G | 1C 9H | 5G | 6G | 1C 9G | 2G 7H | 9H | 9G |
| 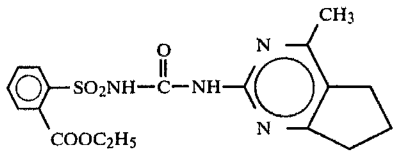 | 0.4 | 9G | 9H | 9G | 10E | 2C 9G | 3C 9H | 2C 9H | 1C 9G | 9G | 8H | 10E | 3C |
| 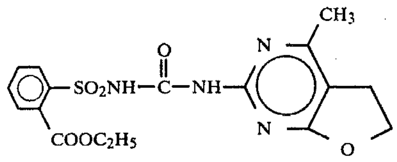 | 0.4 | 9G | 9H | 9G | 10E | 5C 9G | 9H | 9H | 10E | 10E | 9H | 10E | 10E |
| 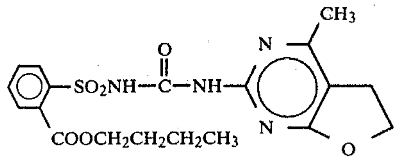 | 0.4 | 9G | 9H | 1C 8G | 7G | 1C 6G | 9H | — | 1C 8G | 1C 9G | 1C 4H | 9H | 4C |
| 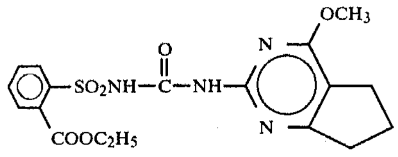 | 0.4 | 9G | 9H | 2C 9G | 1C 9G | 1C 5G | 9H | 1C 7G | 9G | 2U 9G | 1C 4H | 9H | 1C 9G |

TABLE A-continued
| | | | | | | | | | | | | | |
|---|---|---|---|---|---|---|---|---|---|---|---|---|---|
| 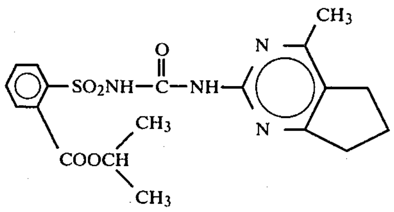 | 0.4 | 9G | 9G | 9G | 9G | 2G | 2C,9H | 1C,6G | 3G | 9H | 1H,3G | 9H | 9H |
| 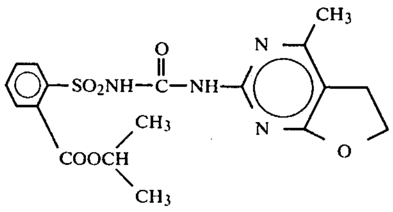 | 0.4 | 9G | 8G | 9G | 5G | 1C,5G | 2C,9H | 5G | 0 | 1C,6G | 2C | 1C,8H | 1C,9G |
| 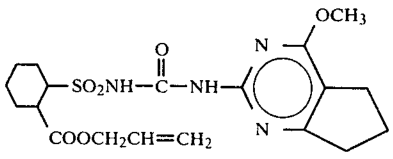 | 0.4 | 9G | 9H | 8G | 7G | 1C | 1C,5G | 3G | 0 | 1C,6G | 3G | 1C,6G | 1C,8G |
| 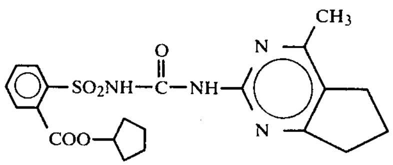 | 0.4 | 10E | 8G | 8G | 3G | 0 | 2C,8G | 2G | 2G | 2C,7G | 1C,2H | 9H | 1C,9G |
| 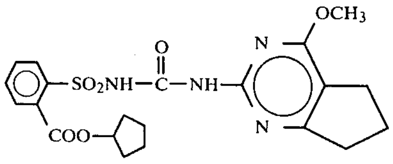 | 0.4 | 10E | 9G | 5G | 4G | 0 | 2C,5G | 0 | 3G | 1C,7G | 2C | 9H | 1C,9G |

TABLE A-continued
| | | | | | | | | | | | | | |
|---|---|---|---|---|---|---|---|---|---|---|---|---|---|
| 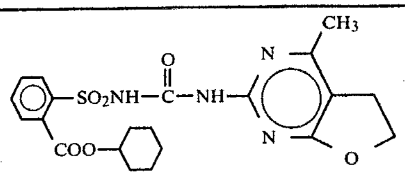 | 0.4 | 9G | 9H | 8G | 4G | 3G | 1C,9H | 1C,7G | 1C,8G | 1U,9G | 1C,1H | 9H | 9H |
| 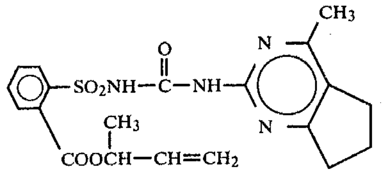 | 0.4 | 8G | 8H | 7G | 6G | 2G | 1C,6G | 3G | 3G | 1C,8G | 1H | 10E | 9H |
| 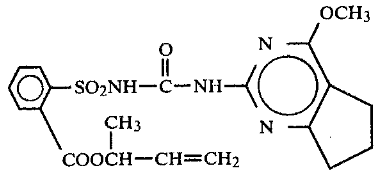 | 0.4 | 8G | 9H | 5G | 0 | 0 | 4G | 0 | 0 | 1C,3G | 2G | 9H | 1C,9G |

Test B

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pennsylvanicum*), pigweed (*Amaranthus retroflexus*), morningglory (*Ipomoea hederacea*), cassia (*Cassia tora*), teaweed (*Sida spinosa*), velvetlead (*Abutilon theophrasti*), and jimsonweed (*Datura stramonium*). A 12.5 cm diameter plastic pot was also filled with prepared soil and planted with rice and wheat. Another 12.5 cm pot was planted with sugarbeets. The above four containers were treated preemergence with several test compounds within the scope of the invention.

Twenty-eight days after treatment, the plants were evaluated and visually rated for response to the chemical treatments utilizing the rating system described previously for Test A. The data are summarized in Table B. Note that certain compounds are useful as preemergence treatments for weed control in crops such as soybeans and wheat.

PRE-EMERGENCE ON FALLSINGTON SILT LOAM

| | Rate kg/ha | Crab-grass | Barnyard-grass | Sorghum | Wild Oats | Johnson-grass | Dallisgrass | Giant foxtail | Ky. bluegrass | Cheatgrass | Sugarbeets | Corn | Mustard |
|---|---|---|---|---|---|---|---|---|---|---|---|---|---|
| 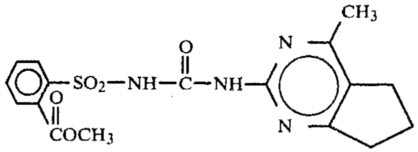 | 0.007 | 0 | 5G | 6G,3H | 2G | 4G | 5G | 3G | 5G | 7G | 4G | 5G,3H | 7G |
| " | 0.03 | 0 | 6G,3C | 9G,5H | 3G | 6G,5H | 5G | 4G,2C | 8G,4C | 8G,8C | 7G,4C | 7G,7H | 7G,3C |
| " | 0.06 | 4G | 8G,5H | 10E | 3G | 7G,5H | 6G | 8G,7C | 8G,8C | 8G,9C | 8G,8C | 8G,8H | 7G,5C |
| 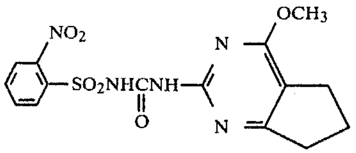 | 0.06 | 0 | 0 | 0 | 0 | 0 | 0 | 0 | 4G | 5G | 7G,5C | 0 | 6G |
| " | 0.25 | 4G | 4G | 4G | 0 | 3G | 5G | 3G | 8G | 8G,5H | 7G,8C | 0 | 7G |
| 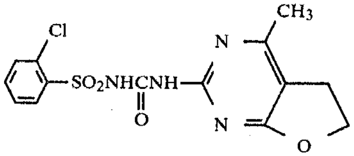 | 0.06 | 5G | 5G | 4G | 0 | 5G | 8G | 6G | 8G,5C | 10E | — | 5G | 8G |
| " | 0.25 | 9G,8C | 7G,5C | 8G,3H | 0 | 7G | 9G,8C | 8G,5H | 10C | 10E | — | 7G,5H | 10C |
| 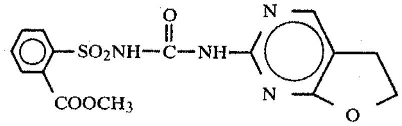 | 0.03 | 0 | 4G | 7G,5H | 0 | 7G | 5G | 5G | 6G,3C | 3C | 3G | 0 | 6G |
| " | 0.125 | 6G,2C | 8G,5C | 9G,9C | 4G | 8G,4C | 7G | 8G | 8G,7C | 9G,9C | 7G,6C | 0 | 8G,3C |
| 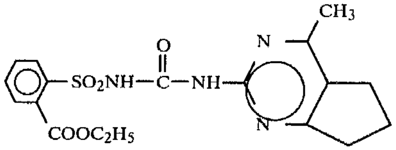 | 0.03 | 0 | 0 | 6G,3H | 0 | 5G,5H | 3G | 3G | 7G,3C | 8G,8C | 5G,3C | 5G,3H | 7G |

-continued
PRE-EMERGENCE ON FALLSINGTON SILT LOAM
| | | | | | | | | | | | | | | |
|---|---|---|---|---|---|---|---|---|---|---|---|---|---|---|
| " | 0.125 | 9G,8C | 9G,8C | 10C | 6G,4C | 8G,5H | 8G,5H | 9G,9C | 7G,5C | 10E | 7G,7C | 8G,5H | 8G,5C |
| 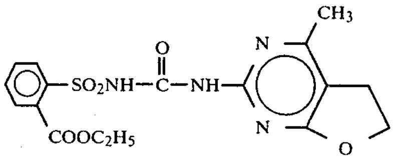 | 0.03 | 5G | 8G,5C | 10C | 6G,5C | 8G,3C | 8G,4C | 7G,3C | 7G,7C | 10E | 7G,7C | 7G,3H | 8G,3C |
| " | 0.125 | 7G,2C | 9G,9C | 10C | 7G,6C | 9G,9C | 9G,9C | 10C | 8G,9C | 10E | 7G,7C | 10C | 9G,5C |
| 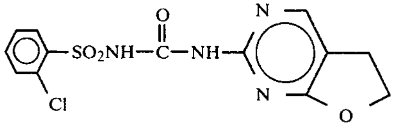 | 0.06 | 0 | 0 | 9 | 0 | 0 | 0 | 0 | 0 | 0 | 0 | 0 | 5G |
| " | 0.25 | 0 | 3G | 3G | 0 | 0 | 4G | 5G | 5G | 4G | 3G,4C | 0 | 6G |
| 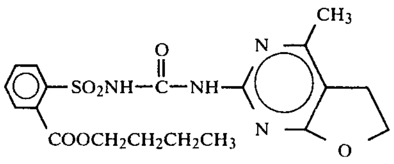 | 0.03 | 0 | 0 | 0 | 0 | 0 | 0 | 5G | 5G | 4G | 0 | 0 | 6G |
| " | 0.125 | 0 | 3G | 4G,2H | 2G | 3G | 3G | 8G | 7G | 8G,3C | 2G | 0 | 7G |
| 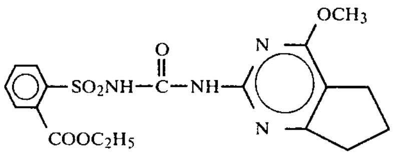 | 0.06 | 0 | 4G | 6G,3H | 0 | 0 | 3G | — | 5G | 6G | 5G | 0 | 6G |
| " | 0.25 | 0 | 4G,3C | 10C | 3G | 4G,3H | — | 9G | 6G,3H | 7G,4C | 7G,3C | 6G,5H | 7G |

-continued
PRE-EMERGENCE ON FALLSINGTON SILT LOAM
| | Rate kg/ha | Cocklebur | Pigweed | Nutsedge | Cotton | Morning-glory | Cassia | Teaweed | Velvet-leaf | Jimson-weed | Soybean | Rice | Wheat |
|---|---|---|---|---|---|---|---|---|---|---|---|---|---|
| 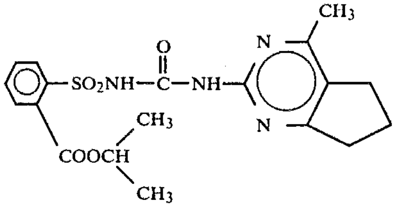 | 0.06 | 0 | 2G | 0 | 0 | 0 | — | 3G | 4G | 7G | 4G | 0 | 6G |
| " | 0.25 | 3G | 7G,3H | 6G,3H | 6G | 5G,3H | 6G | 10E | 6G,3C | 8G,8C | 6G,3H | 6G,3H | 6G |
| 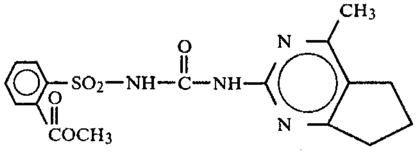 | 0.007 | 3G | 3G | 6G | 3G | 0 | 0 | 0 | 0 | 0 | 3G | 7G,7C | 3G |
| " | 0.03 | 7G | 10E | 8G | 5G,3H | 7G | 8G,8C | 10C | 4G | 3G | 0 | 10E | 5G |
| " | 0.06 | 7G | 10E | 9G | 6G,3H | 8G | 8G,8C | 10C | 6G,2C | 3G | 6G,5H | 10E | 6G,3C |
| 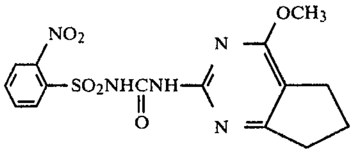 | 0.06 | 0 | 0 | 0 | 0 | 0 | 0 | 0 | 0 | 0 | 2G | 3G | 0 |
| " | 0.25 | 3G | 3G | 0 | 0 | 5G | 0 | 0 | 0 | 0 | 7G,5H | 6G,3H | 3G |
| 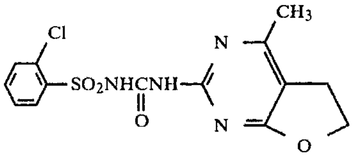 | 0.06 | 0 | — | 8G | 4G | 0 | 6G | 10C | 2G | 0 | 6G,3H | 7G,5C | 5G |
| " | 0.25 | 7G | — | 10E | 7G | 6G | 7G | 10C | 5G,3H | 5G | 7G,5H | 10E | 7G,4C |

-continued
PRE-EMERGENCE ON FALLSINGTON SILT LOAM
| | | | | | | | | | | | | | |
|---|---|---|---|---|---|---|---|---|---|---|---|---|---|
| 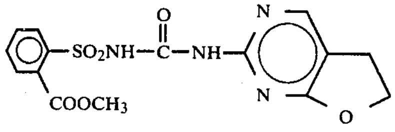 | 0.03 | 0 | — | 5G | 0 | 0 | 0 | 3G | 0 | 0 | 0 | 6G,6C | 2G |
| " | 0.125 | 0 | — | 9G | 7G | 4G | 6G,4C | 5G,5C | 0 | 4G | 2H | 10C | 5G |
| 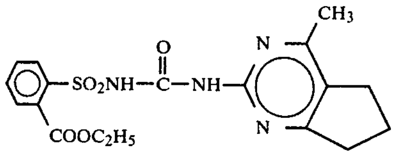 | 0.03 | 7G,5H | — | 7G | 5G | 0 | 6G | 5G | 0 | 4G | 0 | 6G,3H | 3G |
| " | 0.125 | 8G,8H | — | 9G | 6G | 7G | 7G,3C | 5G | 7G,8C | 5G | 3G | 10E | 4G |
| 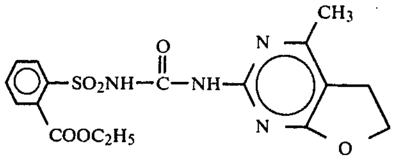 | 0.03 | 7G,5H | — | 10E | 6G | 3G | 6G | 5G | 0 | 3G | 0 | 10E | 7G,5C |
| " | 0.125 | 8G,8H | — | 10E | 8G | 8G | 7G,3C | 7G | 6G,5C | 7G,5C | 3G | 10E | 8G,7C |
| 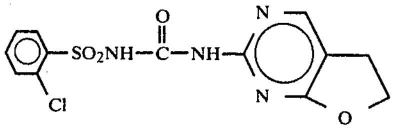 | 0.06 | 0 | — | 0 | 0 | 0 | 0 | — | 3G | 0 | 0 | 0 | 0 |
| " | 0.25 | — | — | 5G | 0 | 0 | 0 | 4G | 3G,3H | 0 | 2G | 0 | 0 |
| 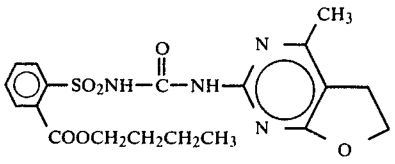 | 0.03 | 6G | — | 4G | 0 | 0 | 0 | 0 | 0 | 0 | 0 | 0 | 0 |
| " | 0.125 | 7G,3H | — | 3G | 0 | 0 | 4G | 5G | 0 | 0 | 0 | 2G | 0 |

-continued
| PRE-EMERGENCE ON FALLSINGTON SILT LOAM | | | | | | | | | | | | | |
|---|---|---|---|---|---|---|---|---|---|---|---|---|---|
| 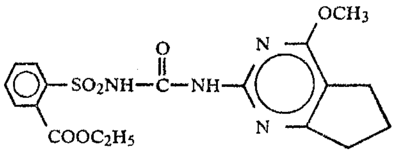 | 0.06 | — | — | 5G | 0 | 0 | 4G | 0 | 0 | 0 | 0 | 5G | 4G |
| " | 0.25 | 5G | — | 5G | 6G,3H | 6G | 6G | 0 | 0 | 0 | 0 | 7G,5C | 4G |
| 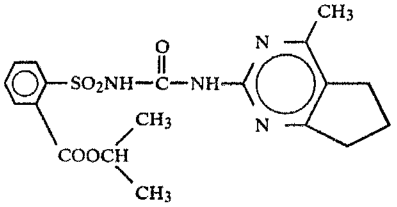 | 0.06 | 4G | — | 0 | 3G | 3G | 2G | 0 | 0 | 0 | 0 | 3G | 2G |
| " | 0.25 | 5G,3H | — | 6G | 6G,3H | 7G | 5G | 0 | 3G | 0 | 2H | 6G | 3G |

Test C

Twenty-five cm diameter plastic pots filled with Fallsington silt loam were planted to soybeans, cotton, alfalfa, corn, rice, wheat, sorghum, velvetleaf (*Abutilon theophrasti*), sesbania (*Sesbania exaltata*), Cassia (*Cassia tora*), morningglory (*Ipomoea hederacea*), jimsonweed (*Datura stramonium*), cocklebur (*Xanthium pennsylvanicum*), crabgrass (Digitaria spp.), nutsedge (*Cyperus rotundus*), barnyardgrass (*Echinochloa crusgalli*), giant foxtail (*Setaria faberii*) and wild oats (*Avena fatua*). Approximately 2½ weeks after planting, the young plants and the soil around them were sprayed overall with the test chemicals dissolved in a non-phytotoxic solvent. Fourteen days after treatment, all species were compared to untreated controls and visually rated for response to treatment. The rating system was as described previously for Test A. The data are presented in Table B. It is evident that the test compounds possess high postemergence activity.

TABLE C

OVER-THE-TOP-SOIL/FOLIAGE TREATMENT

| | 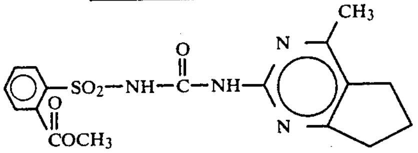 | | | 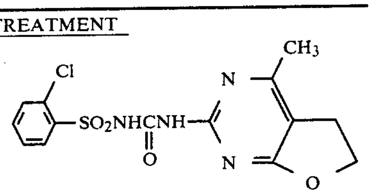 | |
|---|---|---|---|---|---|
| | Rate kg/ha | | | | |
| | 0.03 | 0.06 | 0.25 | 0.007 | 0.03 |
| Soybeans | 10G,9C | 10G,9C | 10G,9C | 10G,5C | 10G,7C |
| Velvetleaf | 5G | 10G,7C | 10C | 7G,3C | 10G,7C |
| Sesbania | 10G,7C | 10G,9C | 10C | — | 2C,3G |
| Cassia | 8G | 7G | 10G,4C | 5G,2C | 7G,3C |
| Cotton | 10G,6C | 10C | 10G,9C | 7G,1C | 8G,2C |
| Morningglory | 10G,6C | 10C | 10G,8C | 9G,1C | 9G,3C |
| Alfalfa | 10G,6C | 10G,6C | 10C | — | 7C |
| Jimsonweed | 8G | 9G,2C | 10G,7C | 0 | 0 |
| Cocklebur | 0 | 7G,3H | 10G,9C | 1G | 6G,2C |
| Corn | 9G,3U | 10G,6U | 10G,9C | 7G,5H | 7G,3C |
| Crabgrass | 0 | 4G | 9G | 1G | 2G |
| Rice | 10G,4C | 10G,6C | 10G,6C | 8G,1C | 8G,3C |
| Nutsedge | 7G | 10G,2C | 10G,8C | 5G | 8G |
| Barnyardgrass | 10G,5C | 10G,6C | 10G,9C | 7G,1C | 8G,3C |
| Wheat | 10G,2C | 10G,3C | 10G,3C | 2G | 4G,2C |
| Giant Foxtail | 10G,2C | 10G,3C | 10G,6C | 3G | 5G |
| Wild Oats | 10G,2C | 10G,2C | 10G,4C | 0 | 1G |
| Sorghum | 10G,3C | 10G,5C | 10C | 3G | 3G |

Test D

Purple nutsedge (*Cyperus rotundus*) tubers were planted about 2 cm deep in Fallsington silt loam soil contained in 10 cm diameter plastic pots. Five tubers were planted in each pot. Compounds of this invention were dissolved in an non-phytotoxic diluent and sprayed at 560 l/ha in four methods of application: soil surface, tuber/soil, soil incorporated, and postemergence. The soil surface spray consisted of spraying the comound on the surface of the firmed covering soil. The tuber/soil spray consisted of spraying the compound on exposed tubers and subtending soil before adding the untreated covering soil. Soil incorporated treatment consisted in mixing the compound with the covering soil before using it to cover the tubers. The postemergence treatment was sprayed on nutsedge foliage and the surrounding soil surface when nutsedge had emerged and grown to a height of about 12 cm. Pots receiving the postemergence treatments were placed directly in the greenhouse. Pots receiving the other treatments were misted with about 0.3 cm water before being transferred to the greenhouse. Response ratings assessed after four weeks are recorded in Table D based on the same rating system as described in Test A. The data indicate that the compounds tested are highly active for the control of nutsedge.

TABLE D

RESPONSE OF NUTSEDGE

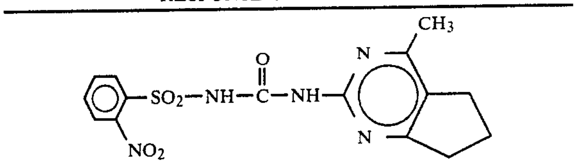

| | RESPONSE RATING AFTER 4 WEEKS | | | |
|---|---|---|---|---|
| Rate kg/ha | Pre-emerg. Surface | Tuber Spray | Soil Incorp. | Post-emerg. |
| 0.125 | 7G | 7G | 7G | 2G |
| 0.50 | 9G | 9G | 9G | 2G |

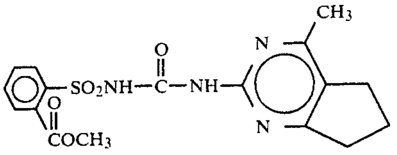

| | RESPONSE RATING AFTER 4 WEEKS | | | |
|---|---|---|---|---|
| Rate kg/ha | Pre-emerg. Surface | Tuber Spray | Soil Incorp. | Post-emerg. |
| 0.03 | 8G | 8E,9G | 6E,9G | 3C,5G |
| 0.125 | 10E | 10E | 10E | 2C,6G |

What is claimed is:

1. A compound selected from

R is 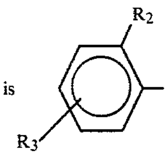 or 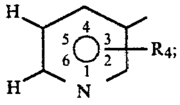

$R_1$ is 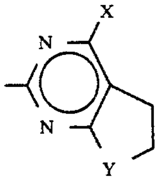 or 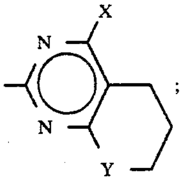;

$R_1'$ is 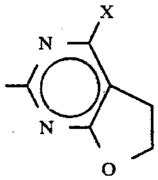 or 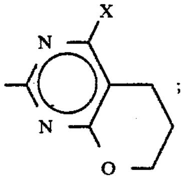;

$R_2$ is H, $CH_3$, $OCH_3$, F, Cl, Br, $NO_2$, $CF_3$, $COR_5$, $S(O)_mR_{10}$, $SO_2NR_{10}R_{11}$, $SO_2OCH_2CF_3$, $SO_2OCH_2CCl_3$ or $SO_2N(OCH_3)CH_3$;

$R_3$ is H, F, Cl, Br, alkyl $C_1$–$C_4$ or $CH_3O$;

$R_4$ is H, Cl, Br, F, alkyl $C_1$–$C_4$, alkoxy $C_1$–$C_4$, $NO_2$, $CO_2R_6$ or $R_{13}$—S—;

$R_5$ is alkoxy $C_1$–$C_6$; alkenyloxy $C_3$–$C_6$; haloalkoxy $C_2$–$C_6$ substituted with 1 to 3 halogens selected from Cl, F and Br; cycloalkoxy $C_5$–$C_6$; $O—CH_2CH_2O)_nR_7$; $OCH_2CH_2CH_2OR_7$; $NR_8R_9$; $N(OCH_3)CH_3$ or $C_1$–$C_4$ alkylthio;

$R_6$ is alkyl $C_1$–$C_6$;

$R_7$ is alkyl $C_1$–$C_2$;

$R_8$ and $R_9$ are independently H or alkyl $C_1$–$C_4$ or $R_8$ and $R_9$ may be taken together to be $(CH_2)_4$, $(CH_2)_5$ or $O(CH_2CH_2—)_2$; and $R_8$ can also be

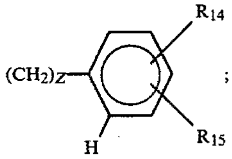;

$R_{10}$ and $R_{11}$ are independently $C_1$–$C_6$ alkyl or $C_3$–$C_4$ alkenyl or $R_{10}$ and $R_{11}$ can be taken together to be $(CH_2)_4$, $(CH_2)_5$ or $O(CH_2CH_2)_2$;

$R_{12}$ is $C_1$–$C_{12}$ alkyl; $CH_2CH_2OCH_3$; $CH_2CH_2OCH_2CH_3$; $CH_2CH_2CH_2OCH_3$;

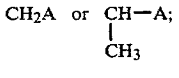

$R_{13}$ is $C_1$–$C_3$ alkyl;

$R_{14}$ is H, F, Cl, Br, $NO_2$, CN, $CF_3$, $C_1$–$C_3$ alkyl, $OCH_3$ or $CH_3S$;

$R_{15}$ is H, F, Cl, Br, $CH_3$ or $OCH_3$;

X is H, $CH_3$, $CH_3O$, Cl or $OCH_2CH_3$;

Y is $CH_2$ or O;

A is $CO_2H$, $CO_2B$, $CONH_2$, phenyl, CN, $C_2$–$C_4$ alkenyl, $C_2$–$C_4$ alkynyl, phenyl substituted with one or two methyl groups or with one or two chlorines;

B is $C_1$–$C_4$ alkyl;

m is 0, 1 or 2;

n is 1 or 2

Z is 0 or 1;

W is oxygen or sulfur; provided that (i) when $R_1$ is

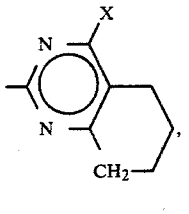, then $R_2$ is $NO_2$, $COR_5$, $SO_2NR_{10}R_{11}$, $SO_2N(CH_3)(OCH_3)$ or $SO_2R_{10}$;

$R_4$ is other than H; and

X is $CH_3$ or $OCH_3$;

(ii) when W is sulfur; when Y is oxygen and their agriculturally suitable salts.

2. A compound of claim 1 wherein W is oxygen.

3. A compound of claim 2 wherein R is

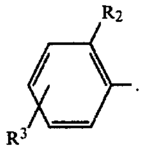.

4. A compound of claim 3 wherein $R_1$ is

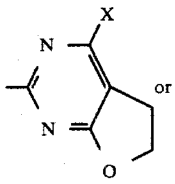 or 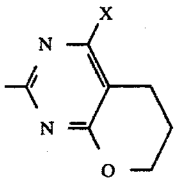

5. A compound of claim 4 wherein X is H, $CH_3$ or $OCH_3$.

6. A compound of claim 5 wherein $R_2$ is $NO_2$, $COR_5$, $SO_2NR_{10}R_{11}$ or $SO_2N(OCH_3)(CH_3)$ and where $R_{10}$ and $R_{11}$ are independently $CH_3$ or $CH_3CH_2$.

7. A compound of claim 6 wherein $R_3$ is H.

8. A compound of claim 7 wherein $R_5$ is $C_1$–$C_3$ alkoxy or allyloxy.

9. The compound of claim 1 which is N-[(6,7-dihydro-4-methyl-5H-cyclopentapyrimidin-2-yl)aminocarbonyl]-2-nitrobenzenesulfonamide.

10. The compound of claim 1 which is 2-[[(6,7-dihydro-4-methyl-5H-cyclopentapyrimidin-2-yl)aminocarbonyl]aminosulfonyl]benzoic acid, methyl ester.

11. The compound of claim 1 which is N-[(6,7-dihydro-4-methoxy-5H-cyclopentapyrimidin-2-yl)aminocarbonyl]-2-nitrobenzenesulfonamide.

12. The compound of claim 1 which is 2-chloro-N-[(5,6-dihydro-4-methylfuro[2,3-d]-pyrimidin-2-yl)aminocarbonyl]benzenesulfonamide.

13. The compound of claim 1 which is N-[(5,6-dihydro-4-methylfuro[2,3-d]pyrimidin-2-yl)-aminocarbonyl]-2-nitrobenzenesulfonamide.

14. The compound of claim 1 which is 2-{[(5,6-dihydro-4-methylfuro[2,3-d]pyrimidin-2-yl)-aminocarbonyl]aminosulfonyl}benzoic acid, methyl ester.

15. The compound of claim 1 which is N'-[(5,6-dihydro-4-methylfuro[2,3-d]pyrimidin-2-yl)aminocarbonyl]-N,N-dimethyl-1,2-benzenedisulfonamide.

16. The compound of claim 1 which is 2-{[(6,7-dihydro-4-methyl-5H-cyclopentapyrimidin-2-yl)aminocarbonyl]aminosulfonyl}benzoic acid, ethyl ester.

17. The compound of claim 1 which is 2-{[(5,6-dihydro-4-methylfuro[2,3-d]pyrimidin-2-yl)aminocarbonyl]aminosulfonyl}benzoic acid, ethyl ester.

18. The compound of claim 1 which is 2-{[(5,6-Dihydro-4-methoxyfuro[2,3-d]pyrimidin-2-yl)-aminocarbonyl]aminosulfonyl}benzoic acid, methyl ester.

19. The compound of claim 1 which is 2-[[(5,6-Dihydro-4-methoxyfuro[2,3-d]pyrimidin-2-yl)-aminocarbonyl]aminosulfonyl]benzenecarbothioic acid, methyl ester.

20. The compound of claim 1 which is 1-[2-[[(5,6-Dihydro-4-methoxyfuro[2,3-d]pyrimidin-2-yl)aminocarbonyl]aminosulfonyl]benzoyl]pyrrolidine.

21. The compound of claim 1 which is 2-[[(5,6-Dihydro-4-methylfuro[2,3-d]pyrimidin-2-yl)-aminocarbonyl]aminosulfonyl]-N,N-dimethylbenzamide.

22. The compound of claim 1 which is 2-{[(4-Chloro-5,6-dihydrofuro[2,3-d]pyrimidin-2-yl)-aminocarbonyl]aminosulfonyl}benzoic acid, methyl ester.

23. The compound of claim 1 which is 2-{[(6,7-Dihydro-4-methyl-5H-pyrano[2,3-d]pyrimidin-2-yl)aminocarbonyl]aminosulfonyl}benzoic acid, methyl ester.

24. The compound of claim 1 which is 2-{[(6,7-Dihydro-4-methoxy-5H-pyrano[2,3-d]pyrimidin-2-yl)aminocarbonyl]aminosulfonyl}benzoic acid, methyl ester.

25. A composition for the control of undesirable vegetation consisting essentially of an herbicidally effective amount of a compound of any of claims 1-24 and at least one of (a) a surface active agent, and (b) a solid or liquid diluent.

26. A method for the control of undesirable vegetation comprising applying to the locus of such undesirable vegetation an herbicidally effective amount of a compound of any of claims 1-24.

27. A method for the control of nutsedge comprising applying to the locus of such nutsedge an herbicidally effective amount of a compound of any of claims 1-24.

28. A compound selected from:

$RSO_2NHC(=S)—NH—R_1''$ and $RSO_2N=C(SR_{12})—NH—R_1''$ where

R is 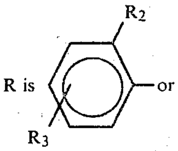 or 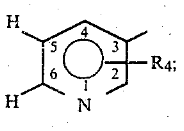;

-continued $R_1''$ is 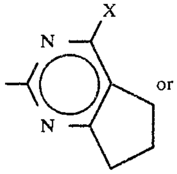 or 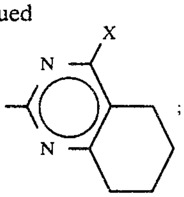;

$R_2$ is H, $CH_3$, $OCH_3$, F, Cl, Br, $NO_2$, $CF_3$, $COR_5$, $S(O)_mR_{10}$, $SO_2NR_{10}R_{11}$, $SO_2OCH_2CF_3$, $SO_2OCH_2CCl_3$ or $SO_2N(OCH_3)CH_3$;

$R_3$ is H, F, Cl, Br, alkyl $C_1$–$C_4$ or $CH_3O$;

$R_4$ is H, Cl, Br, F, alkyl $C_1$–$C_4$, alkoxy $C_1$–$C_4$, $NO_2$, $CO_2R_6$ or $R_{13}$—S—;

$R_5$ is alkoxy $C_1$–$C_6$; alkenyloxy $C_3$–$C_6$; haloalkoxy $C_2$–$C_6$ substituted with 1 to 3 halogens selected from Cl, F and Br; cycloalkoxy $C_5$–$C_6$; $O—CH_2CH_2O)_nR_7$; $OCH_2CH_2CH_2OR_7$; $NR_8R_9$; $N(OCH_3)CH_3$ or $C_1$–$C_4$ alkylthio;

$R_6$ is alkyl $C_1$–$C_6$;

$R_7$ is alkyl $C_1$–$C_2$;

$R_8$ and $R_9$ are independently H or alkyl $C_1$–$C_4$ or $R_8$ and $R_9$ may be taken together to be $(CH_2)_4$, $(CH_2)_5$ or $O(CH_2CH_2—)_2$; and $R_8$ can also be

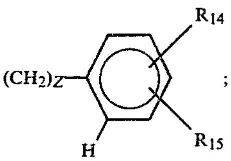;

$R_{10}$ and $R_{11}$ are independently $C_1$–$C_6$ alkyl or $C_3$–$C_4$ alkenyl or $R_{10}$ and $R_{11}$ can be taken together to be $(CH_2)_4$, $(CH_2)_5$ or $O(CH_2CH_2)_2$;

$R_{12}$ is $C_1$–$C_{12}$ alkyl; $CH_2CH_2OCH_3$; $CH_2CH_2OCH_2CH_3$; $CH_2CH_2CH_2OCH_3$;

$CH_2A$ or $CH(CH_3)—A$;

$R_{13}$ is $C_1$–$C_3$ alkyl;

$R_{14}$ is H, F, Cl, Br, $NO_2$, CN, $CF_3$, $C_1$–$C_3$ alkyl, $OCH_3$ or $CH_3S$;

$R_{15}$ is H, F, Cl, Br, $CH_3$ or $OCH_3$;

X is H, $CH_3$, $CH_3O$, Cl or $OCH_2CH_3$;

A is $CO_2H$, $CO_2B$, $CONH_2$, phenyl, CN, $C_2$–$C_4$ alkenyl, $C_2$–$C_4$ alkynyl, phenyl substituted with one or two methyl grohups or with one or two chlorines;

B is $C_1$–$C_4$ alkyl;

m is 0, 1 or 2;

n is 1 or 2; and

Z is 0 or 1; provided that (i) when $R_1''$ is

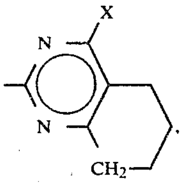

then $R_2$ is $NO_2$, $COR_5$, $SO_2NR_{10}R_{11}$, $SO_2N(CH_3)(OCH_3)$ or $SO_2R_{10}$;

$R_4$ is other than H; and

X is $CH_3$ or $OCH_3$.

* * * * *

UNITED STATES PATENT OFFICE
CERTIFICATE OF CORRECTION

PATENT NO. : 4,339,267

DATED : July 13, 1982

INVENTOR(S) : GEORGE LEVITT

It is certified that error appears in the above-identified patent and that said Letters Patent are hereby corrected as shown below:

Claim 1, column 128, after line 68, insert $$-- \ RSO_2NH\overset{W}{\overset{\|}{C}}NHR_1 \quad \text{or} \quad RSO_2N{=}\overset{SR_{12}}{\overset{|}{C}}{-}NHR_1' \ -- .$$

Claim 1, column 129, line 32, delete "$O-CH_2C-$" and insert therefor -- $O\{CH_2C-$ --.

Claim 28, column 132, line 17, delete "$O-CH_2C-$" and insert therefor -- $O\{CH_2C-$ --.

Signed and Sealed this

*Twenty-sixth* Day of *October 1982*

[SEAL]

*Attest:*

GERALD J. MOSSINGHOFF

*Attesting Officer* *Commissioner of Patents and Trademarks*